US009697582B2

(12) United States Patent
Grunkin et al.

(10) Patent No.: US 9,697,582 B2
(45) Date of Patent: *Jul. 4, 2017

(54) METHODS FOR OBTAINING AND ANALYZING IMAGES

(71) Applicant: Visiopharm A/S, Horsholm (DK)

(72) Inventors: Michael Grunkin, Skodsborg (DK); Steen T. Rasmussen, Vaerlose (DK); Kim A. Bjerrum, Copenhagen Nv (DK); Johan Dore Hansen, Naerum (DK)

(73) Assignee: Visiopharm A/S, Horsholm (DK)

( * ) Notice: Subject to any disclaimer, the term of this patent is extended or adjusted under 35 U.S.C. 154(b) by 413 days.

This patent is subject to a terminal disclaimer.

(21) Appl. No.: 14/223,371

(22) Filed: Mar. 24, 2014

(65) Prior Publication Data
US 2014/0348410 A1   Nov. 27, 2014

Related U.S. Application Data

(60) Continuation-in-part of application No. 13/529,440, filed on Jun. 21, 2012, now Pat. No. 8,682,050, which
(Continued)

(30) Foreign Application Priority Data

Nov. 16, 2006 (DK) .................................. 2006 01507
Aug. 15, 2008 (DK) .................................. 2008 01107

(51) Int. Cl.
*G06K 9/00* (2006.01)
*G06T 3/00* (2006.01)
(Continued)

(52) U.S. Cl.
CPC ..... *G06T 3/0081* (2013.01); *G01N 33/57415* (2013.01); *G06F 19/321* (2013.01);
(Continued)

(58) Field of Classification Search
CPC ....................................................... G06K 9/00
(Continued)

(56) References Cited

U.S. PATENT DOCUMENTS 4,932,044 A   6/1990   Williams et al.
4,982,162 A   1/1991   Zakhor et al.
(Continued)

FOREIGN PATENT DOCUMENTS

WO      0151928 A1    7/2001
WO      03060653 A2   7/2003
(Continued)

OTHER PUBLICATIONS

Fiala, J. et al., Extending Unbiased Stereology of the Brain Ultrastructure to Three-Dimensional Volumes, Journal of the American Medical Informatics Association, 8(1): 1-16, Jan./Feb. 2001.
(Continued)

*Primary Examiner* — Joseph Chang
(74) *Attorney, Agent, or Firm* — Dinsmore & Shohl LLP

(57) ABSTRACT

Disclosed is a method and a system for obtaining and analyzing image pairs, obtained as sections of specimen. The invention facilitates registration of two corresponding images, one from each section of the specimen. The invention includes performing a registration process of the two images thereby obtaining a mathematical transformation rule and afterwards using said transformation rule for each image field identified in one image allowing that the corresponding image field in the other image may be identified as well. After the corresponding image pairs have been obtained using the method of the present invention, the sections can be assessed, such as by identifying the counting
(Continued)

Example of a workflow for a Manual Physical disector events for at least one type of object on the image fields within at least one corresponding image pair, optionally using automatic means.

33 Claims, 35 Drawing Sheets

Related U.S. Application Data is a division of application No. 12/514,918, filed as application No. PCT/DK2007/050171 on Jul. 10, 2008, now Pat. No. 8,229,194, application No. 14/223,371, which is a continuation-in-part of application No. 13/058,385, filed as application No. PCT/DK2009/050202 on Aug. 14, 2009, now Pat. No. 8,731,845.

(60) Provisional application No. 60/878,082, filed on Jan. 3, 2007.

(51) Int. Cl.
| | |
|---|---|
| G01N 33/574 | (2006.01) |
| G06F 19/00 | (2011.01) |
| G06T 7/00 | (2017.01) |
| G06T 7/33 | (2017.01) |

(52) U.S. Cl.
CPC .......... *G06K 9/0014* (2013.01); *G06T 3/0068* (2013.01); *G06T 7/0012* (2013.01); *G06T 7/33* (2017.01); *G06T 2207/10056* (2013.01); *G06T 2207/30004* (2013.01); *G06T 2207/30024* (2013.01)

(58) Field of Classification Search
USPC ................................................. 382/128, 133
See application file for complete search history.

(56) References Cited

U.S. PATENT DOCUMENTS

| | | | |
|---|---|---|---|
| 5,281,517 | A | 1/1994 | Bacus et al. |
| 5,548,661 | A | 8/1996 | Price et al. |
| 5,939,281 | A | 8/1999 | Lehmann et al. |
| 6,466,690 | B2 | 10/2002 | Bacus et al. |
| 6,962,789 | B2 | 11/2005 | Bacus |
| 7,079,675 | B2 | 7/2006 | Hamer et al. |
| 7,085,426 | B2 | 8/2006 | August |
| 7,130,484 | B2 | 10/2006 | August |
| 7,200,252 | B2 | 4/2007 | Douglass |
| 7,219,016 | B2 | 5/2007 | Rimm et al. |
| 7,266,249 | B2 | 9/2007 | Ghosh et al. |
| 7,684,596 | B2 | 3/2010 | Watson et al. |
| 8,229,194 | B2 * | 7/2012 | Grunkin et al. ............. 382/128 |

| | | |
|---|---|---|
| 2003/0185450 A1 | 10/2003 | Garakani et al. |
| 2004/0029213 A1 | 2/2004 | Callahan et al. |
| 2007/0047838 A1 | 3/2007 | Milanfar et al. |
| 2008/0031521 A1 | 2/2008 | Can et al. |
| 2009/0304244 A1 | 12/2009 | Kolatt et al. |
| 2010/0142794 A1 | 6/2010 | Gardi et al. |

FOREIGN PATENT DOCUMENTS

| | | |
|---|---|---|
| WO | 2005024651 A2 | 3/2005 |
| WO | 2007081966 A2 | 7/2007 |
| WO | 2007084363 A2 | 7/2007 |
| WO | 2007089777 A2 | 8/2007 |
| WO | 2007095644 A2 | 8/2007 |
| WO | 2008080403 A1 | 7/2008 |

OTHER PUBLICATIONS

Peterson, D., Quantitative Histology Using Confocal Microsocpy: Implementation of Unbiased Stereology Procedures, Methods, 18:493-507, 1999.

Zarow, C. et al., A Standardized Method for Brain-Cutting Suitable for Both Stereology and MRI-Brain Co-Registration, Journal of Neuroscience Methods, 139(2): 209-215, Oct. 30, 2004.

Grunkin et al., "Practical Considerations of Image Analysis and Quantification of Signal Transduction IHC Staining," Signal Transduction Immunohistochemistry, Methods in Molecular Biology, vol. 717, part 3, pp. 143-154, 2011.

Laurinaviciene et al., "Membrane Connectivity Estimated by Digital Image Analysis of HER2 Immunohistochemistry is Concordant with Visual Scoring and Fluoroscence in situ Hybridization Results: Algorithm Evaluation on Breast Cancer Tissue Microarrays," Diagnostis Pathology, 6, 87, pp. 1-10, 2011.

Skaland, "Proliferation of Breast Cancer. Immunohistochemistry and Digital Image Analysis," Ph.D.-thesis at University of Bergen, Sep. 2009.

Brugmann et al., Digital Image Analysis of Membrane Connectivity Is a Robust Measure of HER2 Immunostains, Breast Cancer Res Treat, Springer+Business Media, 2011.

Gustafsdottir et al., Proximity Ligation Assays for Sensitive and Specific Protein Analyses, Anal Biochem. 345, 1, pp. 2-9, 2005.

Perko et al., Efficient Implementation of Higher Order Image Interpolation, WSCG Short, 2004.

Ronneberger et al., Spatial Quantitative Analysis of Fluorescently Labeled Nuclear Structures: Problems, Methods, Pitfalls, Chromosome Research, Kluwer Academic Publishers, DO, vol. 16, No. 3, May 8, 2008, pp. 523-562.

Sato, Hessian-Based Multiscale Enhancement, Description, and Quantification of Second-Order 3-D Local Structures From Medical Volume Data, In: Handbook of Medical Image Analysis, vol. II: Segmentation Models Part B, 2005, Kluwer Academic, pp. 531-589.

Takeda et al., Kernel Regression for Image Processing and Reconstruction, IEEE Transactions on Image Processing, vol. 16, No. 2, 2007, pp. 349-366.

\* cited by examiner

Figure 2: Adjacent sections are cut from the tissue, and corresponding positions in the two sections are examined to count events from first to second and from second to first section.

Fig 3: Examples of workflows for slide preparation and image registration
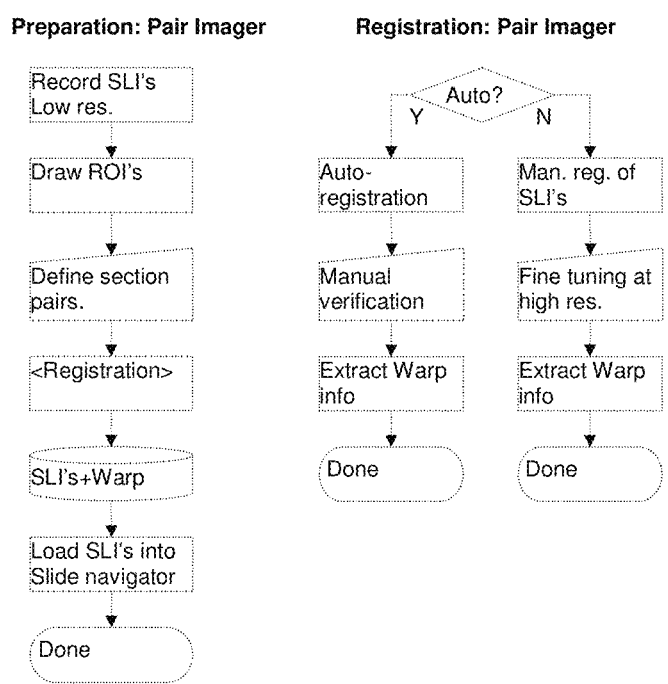

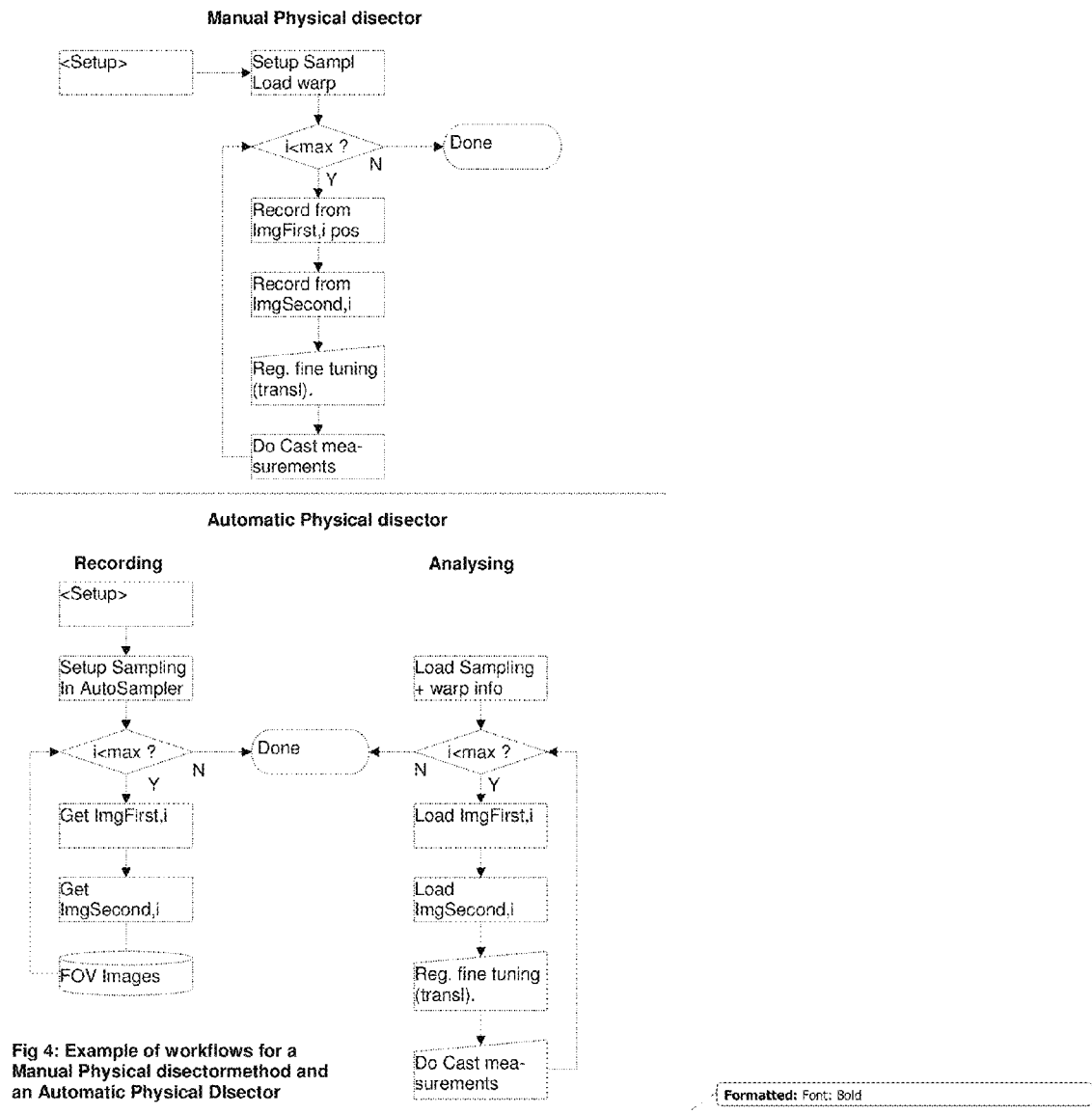
Fig 4: Example of workflows for a Manual Physical disectormethod and an Automatic Physical Disector Fig 5: Example of a workflow for creating sample pairs using an automatic physical disector
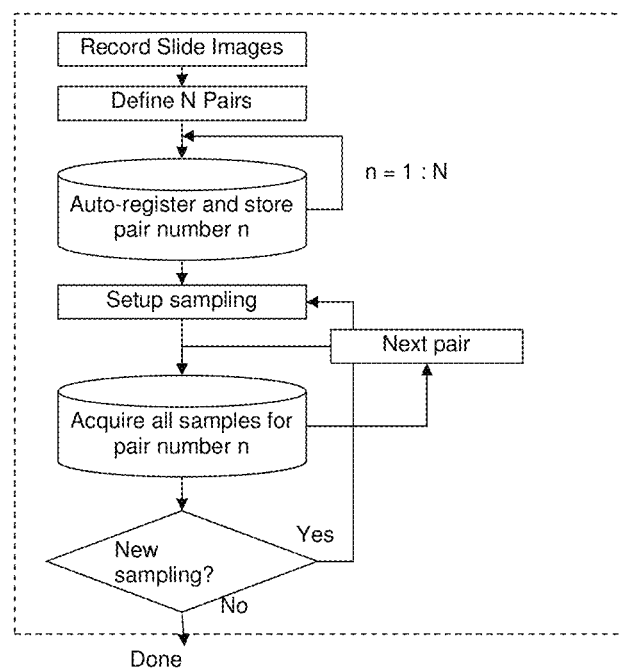

Fig 6: Example of a workflow for quantification of counting events using the Automatic Physical disector
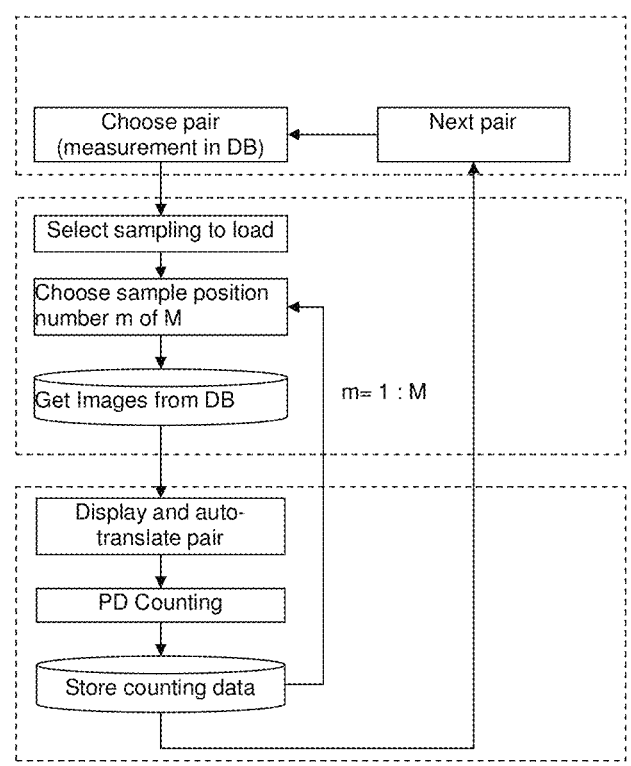
PD= Physical disector

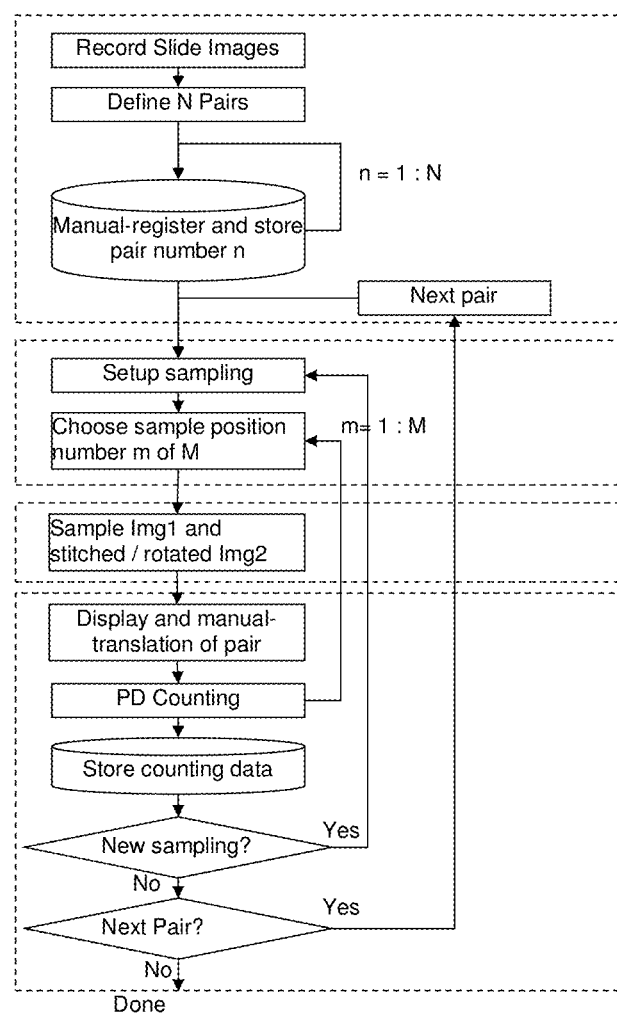
Fig 7: Example of a workflow for a Manual Physical disector

*Examples of Screen Dumps when using pairimager software*
*Figure 8a Super Image Acquisition*
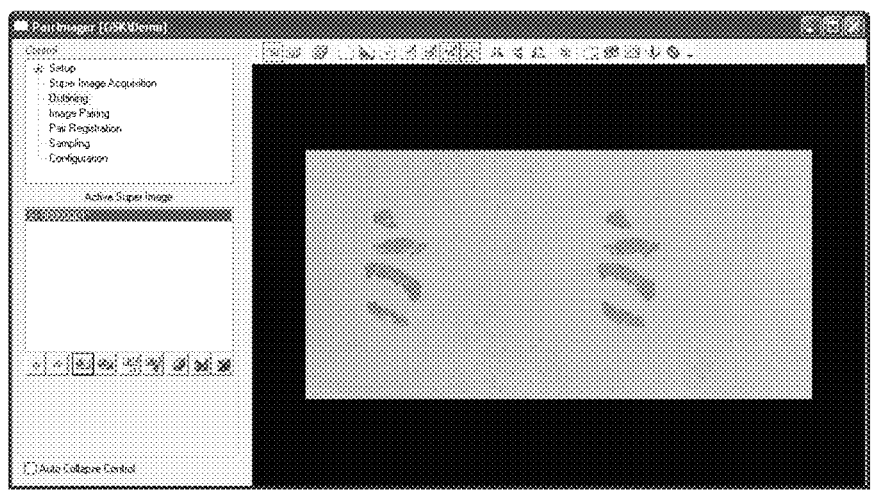
*Figure 8b Section detection*
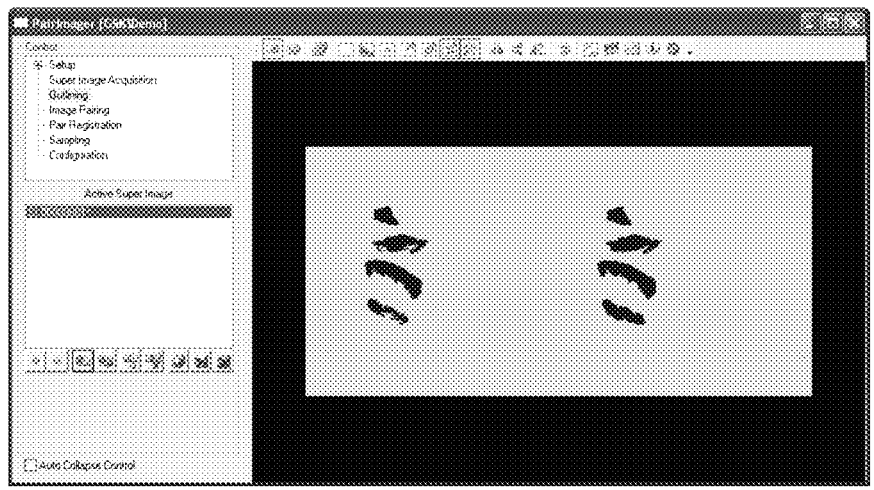

*Figure 8c Section pairing*
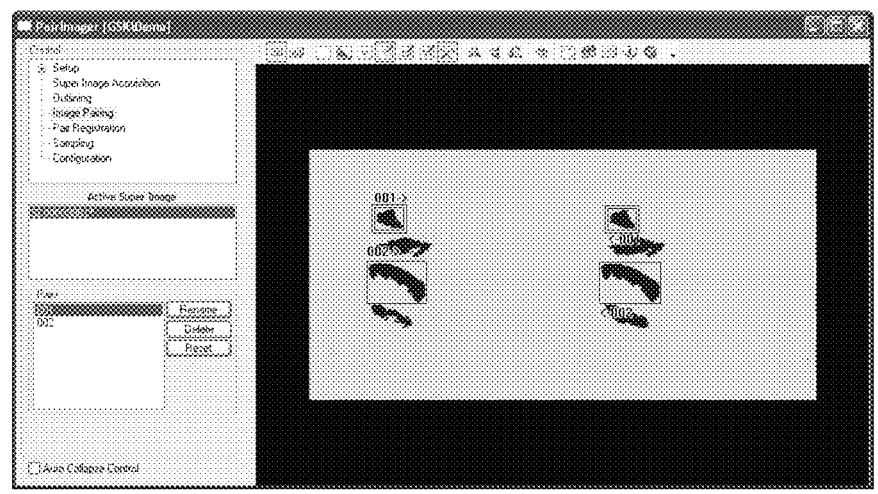
*Figure 9a Section registration*
Pair 1
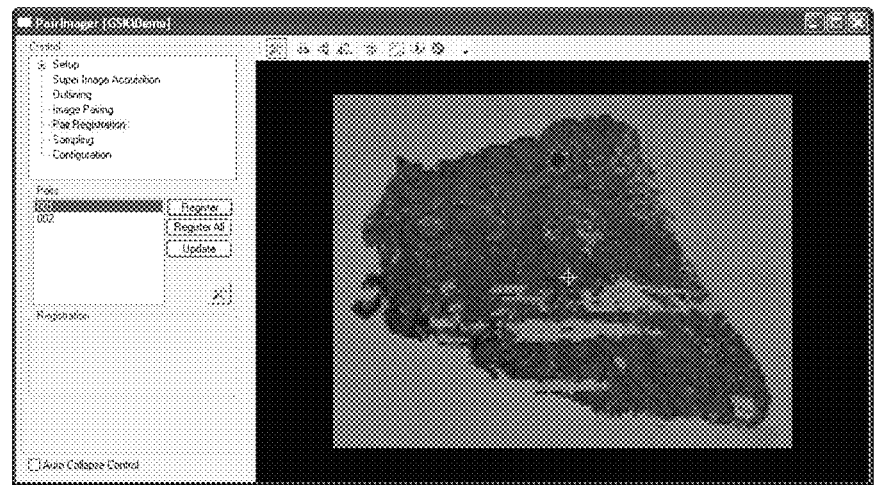
Pair 1, Section 1 before registration Pair 1, Section 2 before registration Pair 1, Section 1 and 2 overlay before registration

Figure 9d
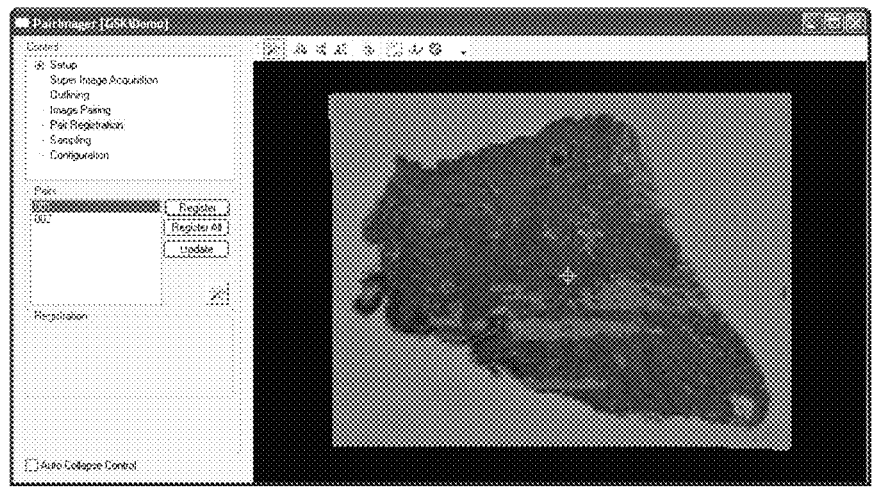
Pair 1, Section 1 and 2 overlay after registration
Figure 10a Pair 2
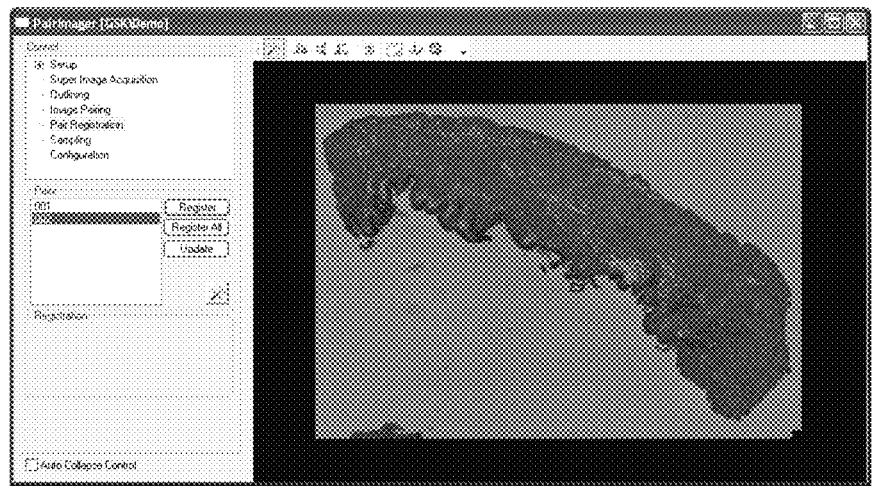
Pair 2, Section 1 before registration Pair 2, Section 2 before registration Pair 2, Section 1 and 2 overlay before registration Pair 21, Section 1 and 2 overlay after registration

METHODS FOR OBTAINING AND ANALYZING IMAGES

CROSS-REFERENCE TO RELATED APPLICATIONS

This Application is a Continuation-in-part of application Ser. No. 13/529,440 filed on Jun. 21, 2012 (now U.S. Pat. No. 8,682,050), which is a Division of application Ser. No. 12/514,918 filed on Jun. 3, 2009 (now U.S. Pat. No. 8,229,194), which is a 371 filing of PCT/DK2007/050171 filed on Nov. 16, 2007, which claims priority of U.S. Provisional Application 60/878,082 filed on Jan. 3, 2007 and Danish Patent Application PA 2006 01507 filed on Nov. 16, 2006. This Application is also a Continuation-in-part of application Ser. No. 13/058,385 filed on Jun. 20, 2011 (now U.S. Pat. No. 8,731,845), which is a 371 filing of PCT/DK2009/050202 filed on Aug. 14, 2009, which claims priority of Danish Patent Application PA 2008 01107 filed on Aug. 15, 2008.

All patent and non-patent references cited in the present application, are also hereby incorporated by reference in their entirety.

FIELD OF INVENTION

The present invention relates to methods for obtaining and analysing images, such as images obtained of a biological specimen.

BACKGROUND OF INVENTION

Quantitative Microscopy and Stereology

The ability to provide quantitative statements about micro-structural tissue properties is becoming increasingly important in biopharmaceutical research and development in diverse applications related to both safety- and efficacy pharmacology.

Typically it is of interest to make quantitative statements about number, length, surface area, and volume of structural features reflecting the condition of an organ. It may even be of interest to investigate second-order properties based on the (number- or volume weighted) distribution of structural features.

There are real challenges and problems associated with the correct quantification of 3-D structural properties of tissues, of which some are related to expensive and labor intensive procedures, others to common misconceptions about the ability to infer 3-D information from 2-D histological sections.

Here, it is important to realize that objects (e.g. cells) in 3-D space that are cut by a 2-D section, as with a histological section, will be seen as profiles. Such 3-D objects will be hit by the 2-D section with a probability in proportion to their size, specifically their height normal to the section. Therefore, the objects of interest do not have the same probability of being counted, which is also the reason that e.g. counting of profiles is a significantly biased measure of the number of objects in 3-D space.

Therefore it is important to use methods that allow for making inference from 2-D sections to 3-D objects. This can be done using certain geometrical probes and estimators. The combination of sampling and the application of a set of unbiased geometrical probes in 3-D are collectively referred to as design-based stereology.

The stereological methods typically applied rely on simple counting of the number of times a feature is intersected by a suitable geometrical probe. To ensure that the intersections are zero-dimensional, i.e. a point that can be counted, the dimension of the probe and the feature under investigation must always sum to three:

Points probe volume
Lines probe surface
Planes probe length
Volumes probe number
(see FIG. 1)

The disector principle is very useful for estimating the number of discrete objects as e.g. cells within a well defined reference space. This principle is widely used, and is perhaps the one area in which design-based stereology has had its largest impact to date. The principle also represents some special challenges seen from an automation point of view.

The major breakthrough in assumption-free, unbiased (stereological) counting was provided by the publication of the Physical Disector paper [Howard & Reed]. The disector consists of a pair of serial sections a known distance apart. The method relies upon the principle that if a particles transect (profile) is seen in one section and not the next, it is counted (this is a counting event).

The physical disector principle is used in a number of frequently occurring situations, for example when the structures of interest are very large, if the tissue is not sufficiently transparent to allow for the use of an optical disector, or when the staining, whatever reason, cannot penetrate sufficiently deep into the tissue under investigation.

The physical disector uses, as the name suggests, at least two adjacent or serial physical sections from the tissue under investigation.

FIG. 2 illustrates two corresponding fields of view sampled from two registered sections of tissue. Using the upper image as reference and the lower image as look-up counting events are identified.

In practice, it is found that most of the time spent in applying a physical disector is dedicated to registering the two sections. Therefore, in order to increase the overall efficiently, counting is done both ways—i.e. by reversing reference and look-up.

Image registration of sections required for the physical disector method rely on spatial mapping and based on both structural/textural and intensity differences between two images. Many types of distortions can be present between images of the two sections to be registered. The task of registration is to select the transformation method, which will remove only the spatial distortions between the images due to difference in acquisition and not due to differences in scene characteristics. With the help of geometric transformations, the spatial relationships between pixels in the images can be modified. A geometric transformation consists of two basic operations: a spatial transformation and a gray-level interpolation. The spatial transformation defines the mapping of the new pixel locations in the output image according to the pixel locations in the input image. There are several methods that can be used for gray level interpolation. For example the nearest neighbor approach, cubic convolution interpolation and bilinear interpolation. For Gray level interpolation, the new pixel coordinates (x1,y1) are calculated by means of the spatial transformation. Digital images are used, therefore the original coordinates have integer values. Depending on the values of the parameters, the new coordinates, (x',y') can become noninteger values. Since the distorted image i2 is digital, its pixel values can only be defined at integer coordinates. Thus using noninteger values for x' and y' causes a mapping into locations of i2 for which no gray levels are defined. The gray level values of these noninteger points should be based on the integer point locations around the noninteger points.

An Unbiased counting frame comprising an area of an image field is preferably used in the process of enumeration counting events in a given disector pair. The unbiased counting frame has an acceptance boundary and a "forbidden" boundary, as shown in FIG. 11. Any particles intersecting the "forbidden" line may not be counted. Particles which are situated inside the counting frame or those that intersect with the acceptance line but not the "forbidden" line may be counted. In FIG. 1, the counting is carried out according to these simple rules.

In the context of the physical disector, counting events are included according to these rules. Thus a cell nucleus is only counted if it is a counting event and fall inside the counting frame as described above. It is only a counting event if it is found in the reference image, but not in the look-up image.

The total amount micro-structure in a volume, such as e.g. number of cells, is based on estimation principles. An estimator is a tool that, given data, is capable of providing an estimate. Typically, the estimators used in stereology provide estimates of the amount of a feature per unit reference volume. Typically the following ratio quantities, generally known as densities, are used:

Volume density: $V_v$, The volume proportion of one phase within a reference volume Surface density: $S_v$, The area of an interface within a unit reference volume Length density: $L_v$, The length of a linear feature within a unit of reference volume Numerical density: $N_v$, The number of discrete objects in a unit reference volume In biological systems, the definition of the reference space is crucial. The fundamental sampling unit (FSU) is related to the organism/organ of interest. It is only in the knowledge of the size of the reference space that the nature of any variation or lack thereof can be fully understood.

In many situations this can be accomplished using advanced image segmentation techniques, that allows for simple test of whether or not a geometrical probe intersects with a given (segmented) structure in field-of-view.

Stereology software is commercially available. The most widespread packages are probably the StereoInvestigator by MicroBrightfield and the CAST system by Visiopharm (taken over by Visiopharm A/S from Olympus Denmark NS).

Even with careful planning and using the physical disector principle, the procedure of obtaining quantification based on design based stereology is still time consuming and labor intensive and certainly not ideally suited for screening purposes or even moderate-volume routine purposes.

Human operators are required for accessing the physical slide and mounting it on a stage under the microscope. Even with software controlling the systematic random sampling, it is necessary to wait while the stage is moving to the next sampling position. Significant time is used for focusing and other adjustments before counting can commence.

Thus, a major obstacle so far has been the inability to deal with microscope slides in the digital domain.

SUMMARY OF INVENTION

The present invention relates to a method and a system for obtaining and analysing image pairs, obtained as sections of specimen. The invention facilitates registration of two corresponding images, one from each section of the specimen.

In one aspect of the present invention is provided a method for obtaining at least one corresponding image pair from at least two adjacent sections A and B of a specimen. Said method comprises the steps of:— a) obtaining a superimage of at least part of section A and a superimage of at least part of section B, b) carrying out an image registration process on the two superimages by establishing correspondence between features of the two related superimages, in order to obtain a mathematical transformation rule, c) identifying an image field within section A, d) using said mathematical transformation rule to identify a corresponding area within section B, said area comprising an image field within section B corresponding to said image field within section A, e) acquiring an image of said image field within section A identified in step c) and acquiring an image of said image field within section B identified in step d) to obtain a corresponding image pair, f) optionally repeating steps c)-e) one or more times to obtain one or more different corresponding image pair(s) of one or more different image fields in the two sections A and B, g) storing a digitized version of said corresponding image pair(s) in a computer-readable storage means.

Optionally, the method can comprise the additional step of carrying out a second registration process on the two images obtained in step e) to obtain a registered corresponding image pair. Furthermore, step f) of the method can optionally be repeated to obtain at least two image pairs, such as at least three, for example at least four, such as at least five, for example at least six, such as at least seven, for example at least eight, such as at least nine, for example at least ten, such as at least 15, for example at least 20, such as at least 25, for example at least 50.

The specimen is preferably a biological sample, such as a tissue section.

After the corresponding image pairs have been obtained using the method of the present invention, the sections can be assessed, such as by identifying the counting events for at least one type of object on the image fields within at least one corresponding image pair, optionally using automatic means. The counting events are preferably quantified, such as by adding the number of counting events and/or objects per volume of tissue, such as obtaining an estimate of the number, such as the total number, of objects or structures in the reference volume together with other relevant statistics, including e.g. a confidence interval for the estimate.

In another aspect, the present invention relates to a computer readable medium comprising instructions for carrying out at least one of the methods according to the present invention.

In another aspect, the present invention relates to an automated system suitable for carrying out the method according to the present invention, preferably comprising, in combination:

a database capable of including (storing and retrieving) a plurality of digital images of a plurality of biological specimens;

a software module for analyzing a plurality of pixels from a digital image of a biological specimen;

a control module comprising instructions for carrying out the method.

The physical disector previously described requires perfect registration between two adjacent sections. This is currently one of the most time-consuming aspects of using the physical disector. The present invention provides many improvements over the prior art physical disectors, not least in the improved registration methods and the fact that counting can occur "offline".

Furthermore, the present invention relates to a new image analysis method for use in diagnosis, prognosis and/or treatment prediction, wherein the new method is capable of enhancing and detecting stained markers manifesting themselves either as "blobs" in a tissue or cell, or arranged along particular linear tissue structures, or the cell membrane or nuclear membrane. The present method provides a tool for enhancing and detecting (identifying, segmenting) the stained parts in the representation of a tissue sample or cell sample, thereby facilitating subsequent processing of the representation and quantification of the staining.

Accordingly, in a first aspect the invention relates to a method for identifying stained targets in a sample, said method comprising
providing at least one digital representation of the sample wherein the sample has been stained with a stain staining a target, and
a) filtering the digital representation with at least three filters, each of said filters comprising filter constant(s), applying said filter constant(s) to each pixels in at least a subset of the digital representation and determining an eigensolution based on the filter output for each pixel in the subset, wherein said filters are capable of enhancing the stained targets obtaining a filtered representation,
b) optionally normalizing the filtered representation,
c) segmenting the digital representation based on information from the optionally normalized filtered representation into stained targets and background, optionally combining with the digital representation, thereby obtaining a segmented representation, wherein said segmented representation discriminates between stained targets and other structures in the digital representation, and
d) from said segmented representation identifying the stained cell targets in the biological cell sample.

In another aspect the invention relates to the use of the filtering method in a method for quantifying the stained target(s), said method comprising providing at least one digital representation of the sample wherein the sample has been stained with a stain staining a target,
performing steps a)-c) as defined above obtaining a segmented representation,
from said segmented representation identifying the stained targets in the sample, and quantifying the staining target(s) in the digital representation.

In a third aspect the invention relates to a method for determining the staining intensity of stained targets, said method comprising
providing at least one digital representation of the sample wherein the sample has been stained with a stain staining a target
performing steps a)-c) as defined in above obtaining a segmented representation,
from said segmented representation identifying the stained targets in the sample, and calculating the staining intensity in the digital representation.

The methods of the invention may also be used for determining the expression level of a target in a cell sample, and accordingly, in a fourth aspect the invention relates to a method for determining an expression level of a target in a biological sample, said method comprising
providing at least one digital representation of the biological sample wherein the cell sample has been stained with a stain staining a target,
performing steps a)-c) as defined above obtaining a segmented representation,
from said segmented representation identifying the stained targets in the biological sample, and calculating the staining intensity in the segmented representation, thereby determining the expression level of the target.

The present invention may also be used in methods for calibrating the equipment used in the imaging processes. Accordingly, in a fifth aspect the invention relates to a method for providing a calibration curve of staining intensity for stained samples, said method comprising
providing a plurality of digital representations of known samples wherein each sample has been stained with a known amount of stain, wherein the sample has been stained with a stain staining a target,
performing steps a)-c) as defined above obtaining a segmented representation,
from said segmented representation identifying the stained targets in the sample, and calculating the staining intensity in the segmented representation for each digital representation, thereby obtaining a calibration curve for the staining intensity.

And also, in a sixth aspect to a method for calibrating a digital imaging apparatus, comprising
providing a plurality of digital representations of known samples wherein each sample has been stained with a known amount of stain, wherein the sample has been stained with a stain staining a target,
performing steps a)-c) as defined above obtaining a segmented representation,
from said segmented representation identifying the stained targets in the, and calculating the staining intensity in the segmented representation for each digital representation,
comparing the calculated staining intensity with a calibration curve as defined above, thereby obtaining a calibration measure, and
calibrating the digital imaging apparatus based on said calibration measure.

In order to obtain valid results from any staining method the staining quality of the stained targets are important, such as for example the dilution of the stains as well as the time spent for processing the stain. The present invention relates in a seventh aspect to a method for evaluating the staining quality of stained targets, said method comprising
providing at least one digital representation of the sample wherein the sample has been stained with a stain staining a target,
performing steps a)-c) as defined above obtaining a segmented representation,
calculating the staining intensity in the segmented representation for each digital representation,
comparing the calculated staining intensity with a calibration curve as defined above, and
evaluating the staining quality of the stained targets.

The invention further relates to a method for classifying a sample, said method comprising
identifying stained targets in said sample by a method as defined above,
based on the identified stained targets classifying the sample in relation to two or more groups of samples.

The invention relates in further aspects to a computer readable medium comprising instructions for carrying out the methods as defined above.

Furthermore, the present invention relates to an automated system suitable for carrying out the method described above, comprising, in combination:

a database capable of including a plurality of digital representations of a plurality of biological specimens;
a software module for analyzing a plurality of pixels from a digital representation of a biological specimen; and
a control module comprising instructions for carrying out any of the method defined above.

DRAWINGS

FIG. 3 shows examples of workflows for slide preparation and image registration.

FIG. 4 shows examples of workflow for manual and automatic physical disector.

FIG. 5 shows an example of a workflow for creating sample pairs using an automatic physical disector.

FIG. 6 shows an example of a workflow for quantification of counting events using the automatic physical disector.

FIG. 7 shows an example of a workflow for a manual physical disector.

FIGS. 8a-8c show examples of screen dumps when using a pair imager software, wherein 8a is super image acquisition, 8b is section detection, and 8c is section pairing.

FIGS. 9a-9d shows screen dumps for section pairing and section registration of pair 1 in FIGS. 8a-8c, wherein 9a shows before registration, and 9b overlay before registration, and 9c the two sections after registration, and 9d the overlay after registration.

FIGS. 10a-10d shows examples of screen dumps for registration of pair 2 in FIGS. 8a-8c, wherein 10a shows before registration, and 10b overlay before registration, and 10c the two sections after registration, and 10d the overlay after registration.

Figure 11:
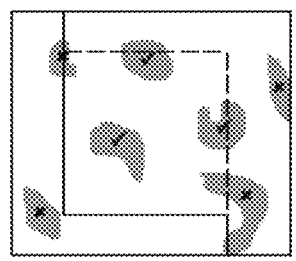

FIG. 11 shows an unbiased counting frame. An unbiased counting frame in a 2D field containing several particles. The ticked particles can be counted and the crossed particle can not.

Figure 12:
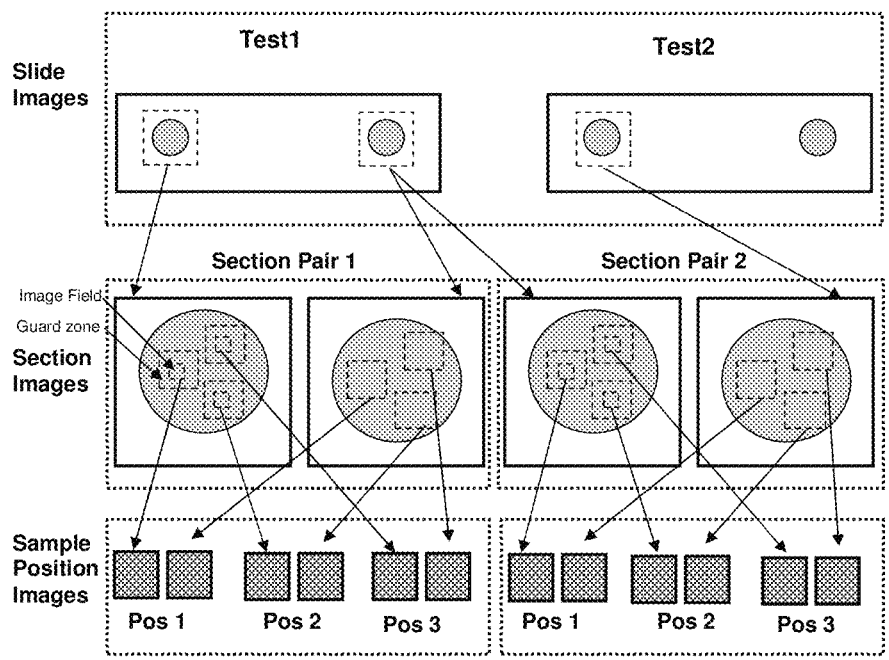

FIG. 12 shows sampling of sections on two slides discussed further in Naming Example below.

FIGS. 13a-d show a digital representation of a stained tissue sample (a) as well as three different results of filtering the digital representation using either the filter according to the invention (b) or Laplacian (c) or gradient (d).

FIGS. 14a-d show the method of the invention from digital representation to segmented representation.

Figure 15A:
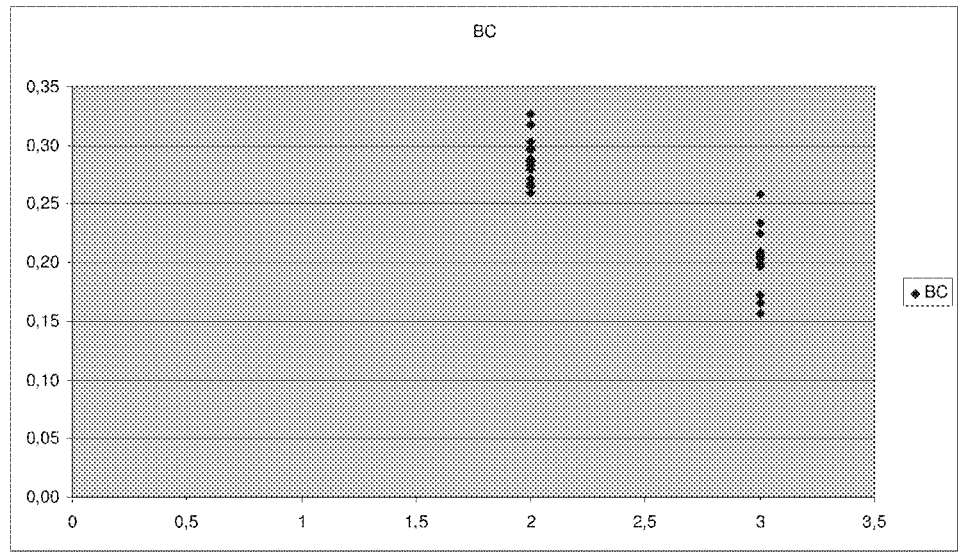
Figure 15B:
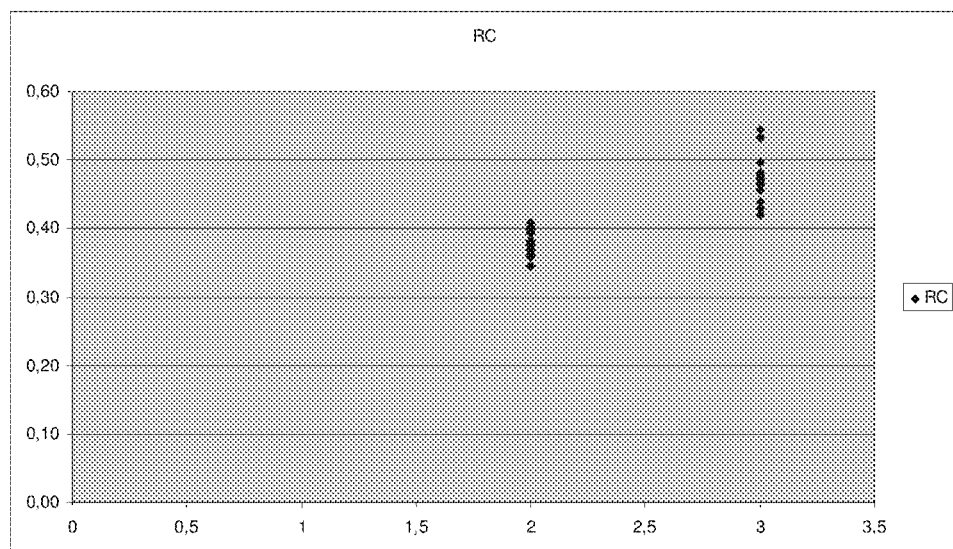
Figure 15C:
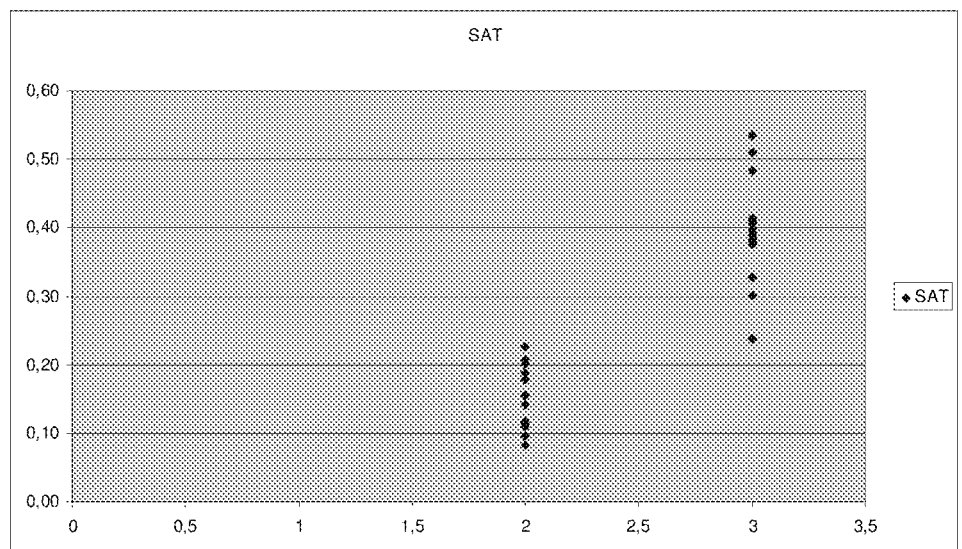

FIGS. 15a-c show the results of grading 30 tissue samples from breast cancer using the method according to the invention by scoring either blue chromaticity (a), red chromaticity (b) or saturation (c)]

Figure 16:
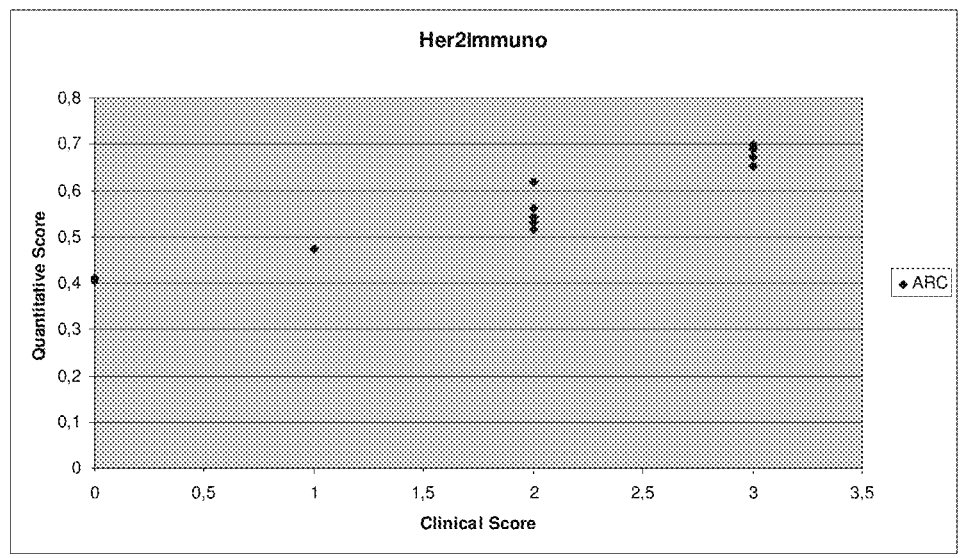

FIG. 16 shows the result of grading another set of tissue samples from breast cancer using the method according to the invention.

Figure 17A:
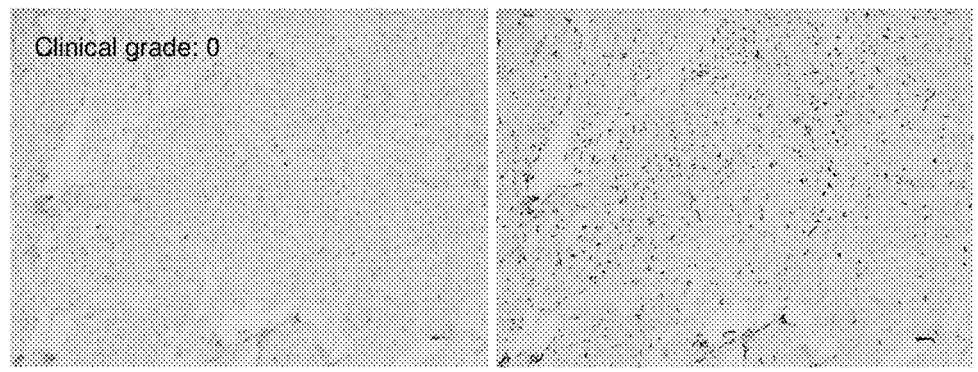
Figure 17B:
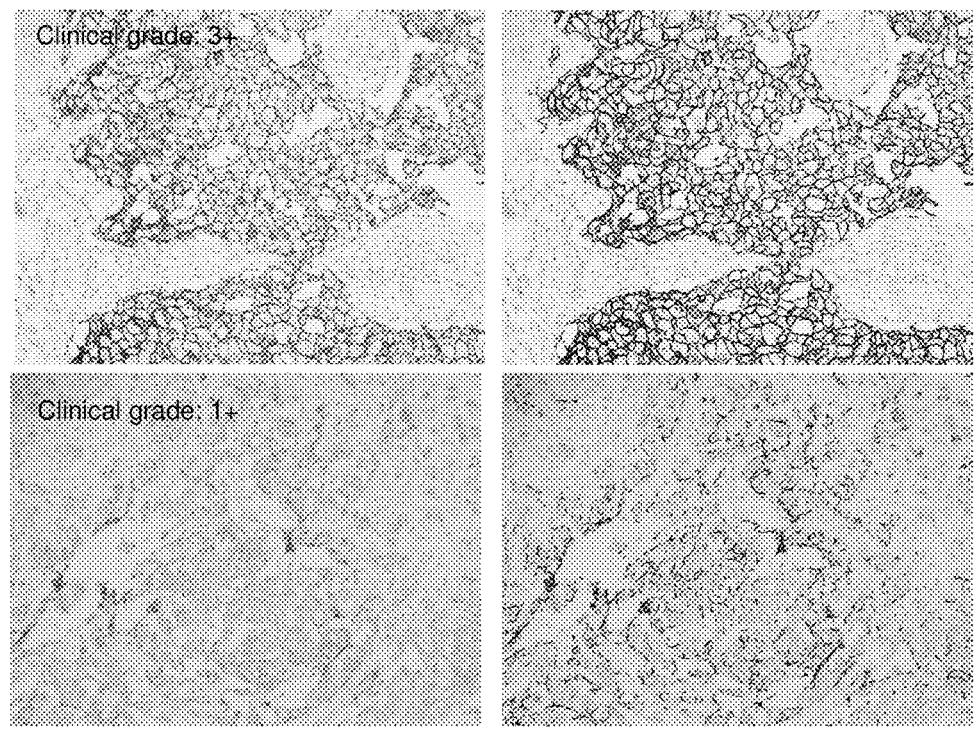

FIG. 17a-b show digital representations and segmented representations of tissue samples representing clinical grade 0, 1+ and 3+, wherein the digital representation is the left-hand representation.

FIGS. 18a-18k shows the use of the methods according to the invention for identifying blob-shaped stained targets in a tissue sample.

Figure 19A:
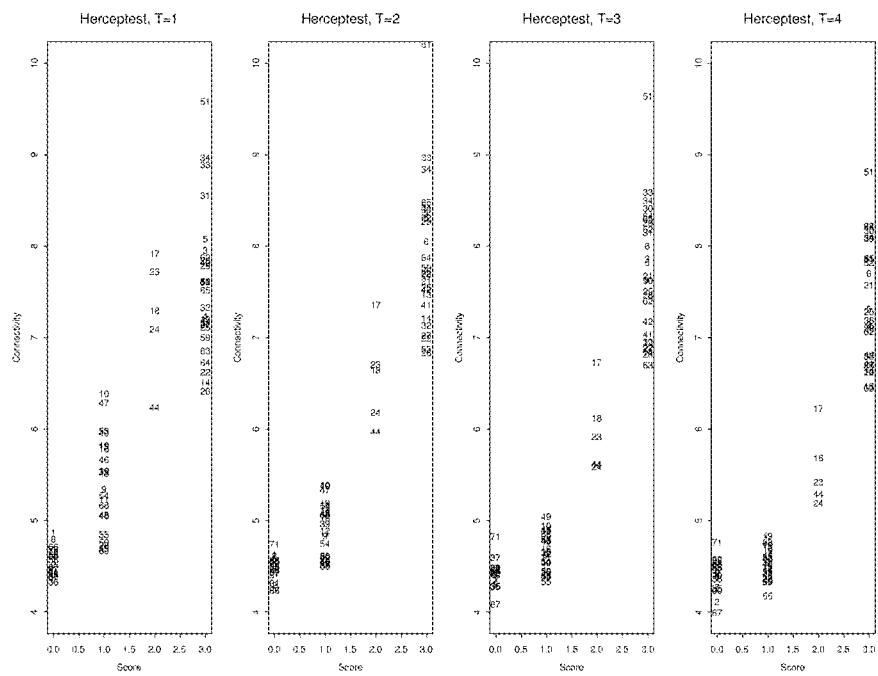
Figure 19B:
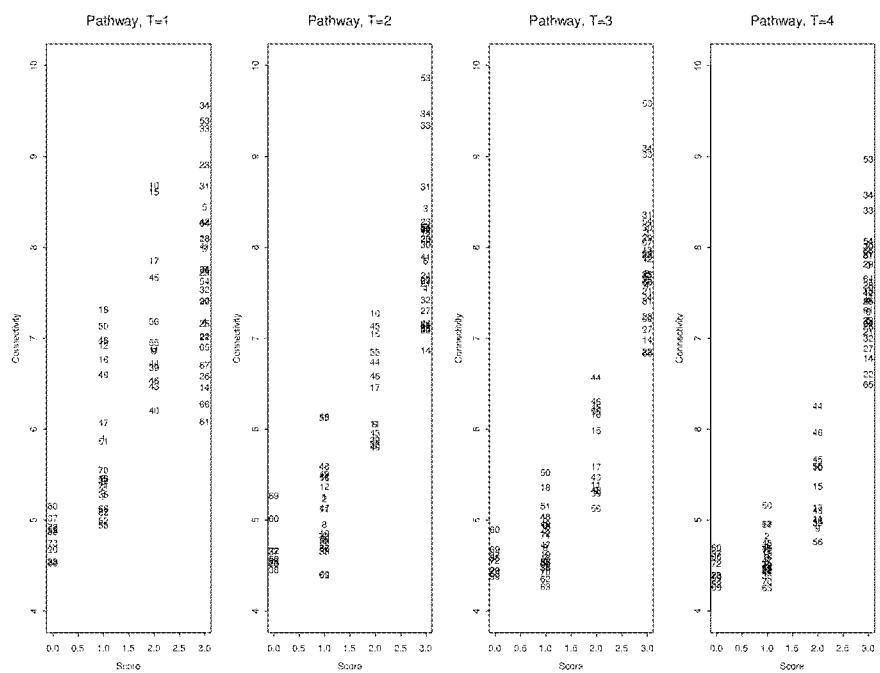

FIGS. 19a-19b show the use of the method of the present invention in analyzing known breast cancer samples stained with Herceptest and Pathway where connectivity is plotted versus clinical score for each threshold level.

Figure 19C:
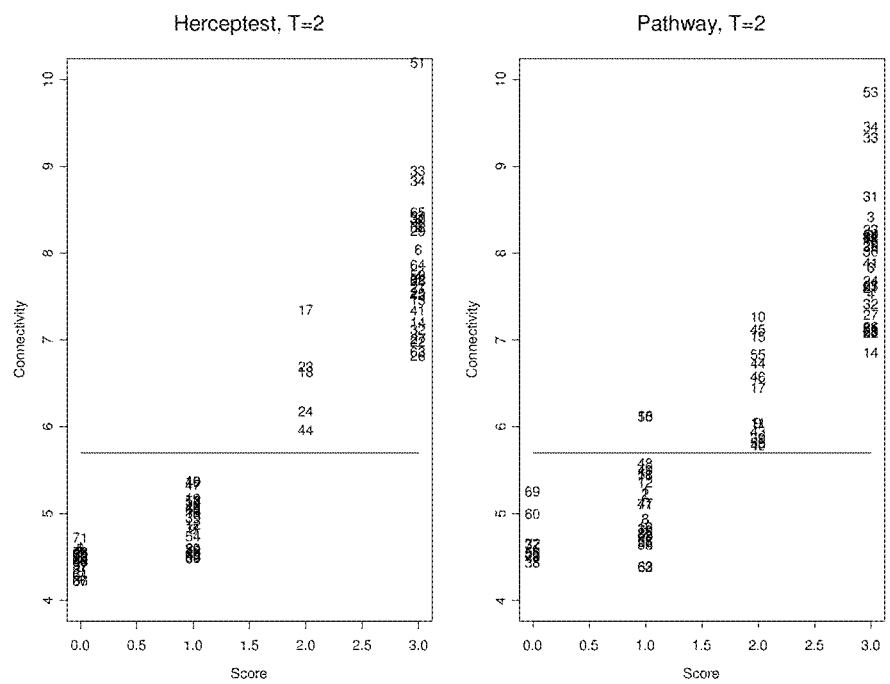

FIG. 19c shows a comparison of the results per the Herceptest and Pathway stains showing the ideal cut-offs for each period.

FIGS. 20a-20d show an experimental series wherein the Median Red Chromaticity (MRC) is plotted for the Herceptest and Pathway data.

Figure 21A:
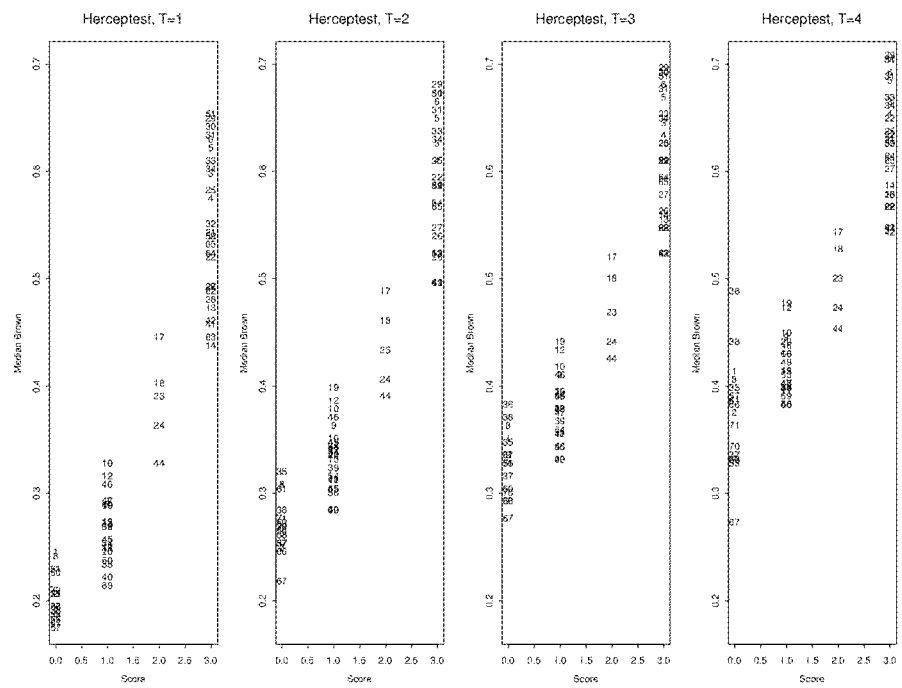
Figure 21B:
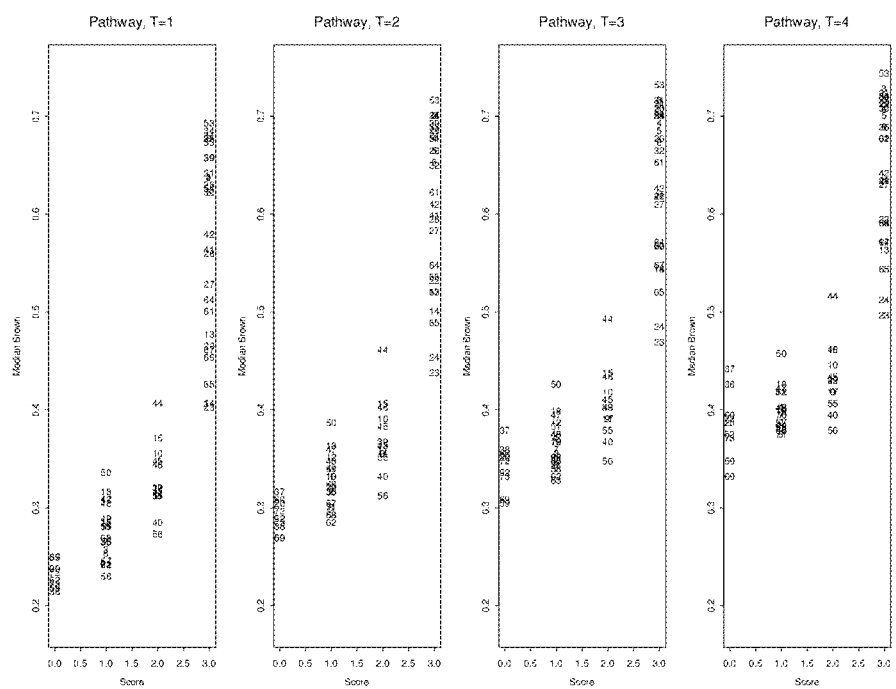

FIGS. 21a and 21b show the plot of the Median Normalized Brown (MBrown) for the Herceptest and the Pathway data.

DETAILED DESCRIPTION OF THE INVENTION

Definitions

Image registration: Image Registration is the process of transforming two digital images into one coordinate system. Registration is necessary in order to be able to compare the structures seen in the two images of a disector pair. One frequently used approach to image registration is to identify the transform (typically translation and rotation) that maximizes cross-correlation or cross-covariance between the two images.

Superimage: An image obtained at low magnification (e.g. ×2), preferably covering the entire slide and/or comprising all the image fields to be sampled. The image is typically formed by systematically acquiring semi-overlapping Fields Of View (FOV) covering the entire specimen and stitching these images together.

Object type: The type of object quantified, such as one or more type of cells, as well as other structures in the image, such as vessels.

Mask: A mask defines an area or Region Of Interest (ROI) in an image. For each image several such masks may be defined. In VIS, masks have unique numbers.

Field Of View (FOV): The part of a given section seen through the microscope.

Adjacent: Adjacent sections may or may not imply contact between sections, but always implies that it is the shortest distance allowing for a meaningful recognition of the structures through which the sections are obtained. As a rule of thumb, the distance between two adjacent sections should be small compared to the size of the objects/structures of interest.

Section: A section is a slice of the specimen to be analysed, in a preferred embodiment a section is a histological section, wherein histological sections are thin slices of tissue applied to a microscopic slide, for example around 5 to 10 micrometers thick, which are viewed under a microscope.

Look-up image/reference image: a corresponding image pair, one is called the reference image and the other the look-up image depending on which image is designated to be the reference image.

Corresponding image pair: This term is used for describing images, either two or more individual fields of view or a number of fields of views that are stitched together, in the reference- and lookup sections that are depicting essentially the same structures, although in different sections. The corresponding image pair may or may not be perfectly registered, but it is a requirement that all structures visible in the reference image are essentially covered in the lookup image.

Counting event: All objects/structures that are visible in the reference image but not in the corresponding lookup image are considered counting events.

Image field: An "image field" is any arbitrary informative region across which an informative quantitative analysis can be carried out. In some instances, an image field is a microscopic field of view at low magnification (e. g. 1.25×-2×). An entire microscope field of view can then be used for the image capturing and analysis at 40×-100× magnification for analysis. Another example of an image field is an area which is selected for a specific analysis.

Guard zone: A zone around the image field in section A or B, that ensures that the correct corresponding image field to the image field in section A is fully contained in the image region acquired in section B.

Offline: The present invention allows for offline quantification of the objects in the image, wherein offline means that the quantification process is conducted on images saved on a memory medium, such as a hard disk, and not during acquisition of the image.

Method for Obtaining at Least One Corresponding Image Pair

In a first aspect, the present invention relates to a method for obtaining at least one corresponding image pair from at least two adjacent sections A and B of a specimen, said method comprising the steps of:— a) obtaining a superimage of at least part of section A and a superimage of at least part of section B, b) carrying out an image registration process on the two superimages by establishing correspondence between features of the two related superimages, in order to obtain a mathematical transformation rule, c) identifying an image field within section A, d) using said mathematical transformation rule to identify an area within section B, said area comprising an image field within section B corresponding to said image field within section A, e) obtaining an image of said image field within section A identified in step c) and obtaining an image of said image field within section B identified in step d) to obtain a corresponding image pair, f) optionally repeating steps c)-e) one or more times to obtain one or more different corresponding image pair(s) of one or more different image fields in the two sections A and B, g) storing a digitized version of said corresponding image pair(s) in a computer-readable storage means.

Obtaining the Sections and Images

As is known by one skilled in the art, general sampling for microscopy of biological sections is hierarchical. Blocks are taken from main specimen, sections are cut from blocks, fields are examined on sections and measurements are made on fields. For the physical disector it is preferred that the distance between adjacent sections is known. These adjacent section pairs can then be marked to indicate that they are a pair. Preferably, the distance between the sections may not be longer than 30% of the size of the particles to be counted. Preferred section thicknesses are less that 4-5 µm.

The sections can for example be viewed using Brightfield microscopy, fluorescence microscopy or confocal microscopy. The images of the sections can be obtained using any suitable system known to one skilled in the art. Preferably a digital camera is used. The system used to obtain the image can optionally also use auto-focus (either software- or hardware-implemented).

For example, the microscope can include motorized stage, an automated apparatus for focussing, for changing lens objectives between high and low magnification, and for adjustment of the light incident of the slide, as well as circuitry for controlling the movement of the motorized stage, typically in response to a command from the processing system. The microscope may also include an automated slide transport system for moving the slides containing the specimen to be classified on to and off of the motorized stage, and a bar code reader for reading encoded information from the slide. An example of a microscope performing at least some of these functions is manufactured by Carl Zeiss, Inc. of Germany, Leica Microsystems, Nikon, or Olympus.

Preferably, the images obtained are monochrome images, color images, or multi-frame (e.g. multispectral) images. Images are preferably stored as TIFF images, or as JPEG or other standard formats.

In another embodiment the superimage and/or the image fields may be acquired from a virtual slide obtained by means of a virtual microscope imaging the sections in question. In this embodiment, the entire tissue area has been scanned at high magnification in e.g. a virtual slide scanner, and the resulting image is already stored on the harddisk. The system now handles this large image as if it was controlling a microscope, stage, camera etc. Thus, the user can use the exact same interface to work with virtual microscope images as when working with an actual microscope. With this approach it is possible to further automate the use of unbiased methods by, potentially, scan sections from an entire study (or several studies), and perform all subsequent operations off-line.

Specimen

Any suitable specimen can be used in the methods of the present invention. Preferably, said specimen is a biological specimen. Thus, said specimen can be a tissue sample. The specimen can also be labelled with at least one chemical marker, such as at least one fluorescent marker. In another embodiment, said specimen can have optical properties. It is preferred that the specimen is illuminated while the images are obtained, such as by using UV or illumination visible to the human eye. In one preferred embodiment, the specimen includes a plurality of cells, such as human cells, such as a plurality of human cells potentially including one or more human cancer cells, such as breast cancer cells.

Superimage

In one embodiment of the method of the present invention, the superimages are obtained using a lower resolution than the resolution used to obtain the images of step e). In another embodiment, the superimages are obtained using a magnification of ×2.5, ×4, ×5 or ×10.

It is to be understood by one skilled in the art that by the references to "two superimages" herein is also intended embodiments in which the two superimages can be comprised in one single larger superimage.

The two images may for example be acquired from conventional microscope slides or from virtual slides.

Registration

Step b) of the method concerns carrying out an image registration process on the two superimages by establishing correspondence between features of the two related superimages, in order to obtain a mathematical transformation rule.

The feature(s) used in the registration process can be any suitable feature recognised by one skilled in the art as useful in the registration process. The feature can for example be an anatomical structure, such as, but not restricted to, an anatomical structure selected from the group consisting of: the outer shape or outline of the section or specimen, vascular structure(s), nerve structure(s), muscle structure(s), cell membrane(s), space(s) in the section, cell(s), an alveolus, particle(s) or a nucleus.

The registration process itself can be carried out using any process known to one skilled in the art. For example, registration can be carried out using a method disclosed in Mainz et. al 1998 or one can use one or more of: Correlation and Sequential methods, Fourier methods or Point mapping methods. Thus, image registration of sections can for example be carried out using one or more of: spatial mapping, a geometric transformation, a combination of a spatial transformation and a gray-level interpolation. Preferred methods for gray level interpolation include for example the nearest neighbor approach, cubic convolution interpolation and bilinear interpolation.

In one preferred embodiment of the present invention, image registration comprises or consists of one or more (preferably all three) of the following:
 1. Detection of tissue area in the two images belonging to the pair
 2. Rigid warp of one image to fit approximately on the other.
 3. Non-rigid warp based on the approximate fit, to fit the images more correctly.

For tissue detection, any method can be used. One preferred embodiment uses the VisioMorph segmentation tool, available commercially from Visiopharm A/S.

The transformation rule obtained by the registration process preferably includes a rotation rule and/or a translation rule and/or a warp rule, which is carried out on at least part of the section.

Identifying an Image Field within Section A

Step c) of the method of the present invention comprises the step of identifying an image field within section A. An image field is chosen e.g. at a random location, a systematic uniformly random location, or at a user defined location.

In one embodiment of the present invention, the locations (defined e.g. as upper left corner) of the considered image field(s) represent a random sample, such as a systemic uniform random sample, based on the reference section and the corresponding locations in the lookup section. In another embodiment of the present invention, the considered image field(s) represent semi-random sample. In another embodiment of the present invention, the first image field is identified at random and the subsequent image fields are identified using a pre-defined function. In another embodiment of the present invention, one or more of the considered image field(s) can be selected in the specimen by a human operator, such as by using a computer mouse. Sampling principles are described in e.g. [Howard & Reed].

When sampling, every part of the original specimen should have the same chance of becoming part of the final sample on which measurements are to be made. Thus, it can in one embodiment be advantageous to apply systematic uniform random sampling at every level of the sampling hierarchy.

Identifying an Image Field within Section B

Step d) of the method of the present invention comprises the step of using said mathematical transformation rule to identify an area within section B, said area comprising an image field within section B corresponding to said image field within section A. It is preferred that the image field within section B comprises an area corresponding to the image field within section A together with a guard zone around said area in section B. The presence of this guard zone has been found by the inventors of the present invention be preferred for realizing the invention. Preferably, the minimum guard zone added to each border of said area in step d) is calculated using the following formula:

$$\frac{(\text{working magnification of said area in step } d)}{(\text{superimage } B \text{ magnification})} \times$$

$$(\text{margin of registration error of superimage } B \text{ in pixels})$$

For example, the area of said area in step d) can be at least 1.1 times the area of said image field within section A, such as at least 1.2 times the area of said image field within section A, for example at least 1.3 times the area of said image field within section A, such as at least 1.4 times the area of said image field within section A, for example at least 1.5 times the area of said image field within section A, such as at least 1.6 times the area of said image field within section A, for example at least 1.7 times the area of said image field within section A, such as at least 1.8 times the area of said image field within section A, such as at least 1.9 times the area of said image field within section A, such as at least 2.0 times the area of said image field within section A, such as at least 2.5 times the area of said image field within section A, such as at least 3.0 times the area of said image field within section A, such as at least 3.5 times the area of said image field within section A, such as at least 4.0 times the area of said image field within section A, such as at least 4.5 times the area of said image field within section A, such as at least 5.0 times the area of said image field within section A, such as at least 6.0 times the area of said image field within section A, such as at least 7.0 times the area of said image field within section A, such as at least 8.0 times the area of said image field within section A, such as at least 9.0 times the area of said image field within section A, such as at least 10 times the area of said image field within section A.

In another embodiment a guard zone is also selected for the image field in section A. Thereby larger image areas may be compared when performing a second registration process, than if only the image fields are compared, thereby increasing the robustness of the second registration.

Area of Image Pairs Taken

For the methods according to the present invention, it is preferred that the total area for all the image pairs taken is at least 0.5% of the area of the section analysed, such as at least 1%, for example at least 2%, such as at least 5%, for example at least 8%, such as at least 10%, for example at least 15%, such as at least 20%, for example at least 25%, such as at least 30%, for example at least 35%, such as at least 40%, for example at least 50%.

Further Optional Method Steps

The methods of the present invention further optionally comprise step f), which relates to repeating steps c)-e) one or more times to obtain one or more different corresponding image pair(s) of one or more different image fields in the two sections A and B, Step f) can be repeated to obtain at least two image pairs, such as at least three, for example at least four, such as at least five, for example at least six, such as at least seven, for example at least eight, such as at least nine, for example at least ten, such as at least 15, for example at least 20, such as at least 25, for example at least 50.

After the images are obtained using the method of the present invention, it is preferred that they are stored in a digitized version of said corresponding image pair(s) in a computer-readable storage means.

Another optional step in the methods of the present invention comprises carrying out the additional step of carrying out a second registration process on the two images obtained in step e) to obtain a registered corresponding image pair. This allows optimal registration and may be carried out using any registration process, such as any of the registration process described herein. Preferably, said registration process is as described in A Survey of Medical Image Registration (9).

The method of the present invention can also comprise the additional step of automatically determining a conclusion from the results of the method, such as a pharmacological conclusion. One preferred conclusion can for example be a conclusion relating to the proliferative index of an organ or tumor, such as a number representing an estimate of the relative number of proliferating cells, optionally with a value indicating the statistical accuracy of said number.

The method of the present invention may be carried out for any type of specimen, such as a histological section of a variety of organs, such as kidneys, lungs, liver, muscle, uterus, bone, heart, fat tissue, and gastrointestinal tissue.

In a preferred embodiment of the present invention, the method further comprises the additional step of automatically presenting a report, and optionally one or more digital image(s), on a graphical user interface.

The methods of the present invention are preferably automated or semi-automated. In the following table the steps that may be carried out automated (AUTO) or optionally automated (OPTIONALLY AUTO) are listed:
Step
AUTO: Creation of superimages by stitching
OPTIONALLY AUTO: Segmentation of tissue sections
OPTIONALLY AUTO: Registration of super images
AUTO: Sampling of image pairs at working resolution (employing auto-focus, auto white balance, auto exposure)
OPTIONALLY AUTO: Fine-registration of corresponding image pairs
AUTO: Recording of user-demarcated counting events In one embodiment of the present invention, any of the methods described herein can be carried out for at least one, two or three different object types, such as for different cell or tissue types and/or different cell structures.

The methods according to the present invention can further comprise the aspect of using a computer readable medium having stored therein instructions for causing one or more processors to execute the steps of the method.

Method for Assessing at Least Two Adjacent Sections of a Specimen

In another aspect, the present invention provides a method for assessing at least two adjacent sections of a specimen. Said method comprises the steps of:—
i) providing at least one corresponding image pair according to any of the methods disclosed above,
ii) identifying the counting events for at least one type of object on said image fields within at least one corresponding image pair, optionally using automatic means.

Said method for assessing at least two adjacent sections can also comprise the additional step of:
quantifying the amount or number of said counting events on the images of said image field(s) within section A and said image field(s) within section B. Said quantification can include e.g. calculating the number of counting events and/or objects per volume of tissue, such as calculating an estimate of the number of counting events and/or objects in the total specimen volume together with a confidence interval. Said quantification can also optionally include the use of an unbiased counting frame. In one embodiment of the present invention, the quantification entails that at least one human operator marks the specific counting events, preferably on a computer interface, such as using a computer mouse. Preferably, the quantification is carried out using an estimator, such as e.g Cavalieris Unbiased Estimator of Volume. Preferably, the quantification process occurs offline.

In another embodiment the quantification step may be assisted by having the system present to the human operator suggested counting events, by for example applying a mark or a label to each suggested counting event in the image. In order to automatically identify suggested counting events in the image, image analysis may be performed of the analyzed image field pairs.

The method according to the present invention for assessing at least two adjacent sections can be carried out for at least two different image fields within the sections, such as for at least three different image fields within the sections, for example for at least four different image fields within the sections, such as for at least five different image fields within the sections, for example for at least six different image fields within the sections, such as for at least seven different image fields within the sections, for example for at least eight different image fields within the sections, such as for at least nine different image fields within the sections, for example for at least ten different image fields within the sections, such as for at least twenty different image fields within the sections; and preferably furthermore wherein the amount or quantity of all the counting events from all the image fields analysed is obtained.

Preferred Embodiments

Preferably, one or more of the following is used in the methods of the present invention:
(i) Automated Sampling
Having identified one or more tissue regions on the slide, preferably using the superimage(s), a further step in the method of the present invention is sampling in order to generate images of one or more image field(s) within sections A and B, and optionally further image pairs. This can be done in several ways, depending upon the application:
1. Exhaustive imaging of each identified image field within the slide, with one or more images per image field. In the latter case, the total image may be produced by stitching of image tiles. Due to lack of perfect alignment (and precision) of standard motorized stages, a cross-correlation based image alignment will often be required as a post-processing step. The images of each image field are stored in the database under a study name, study unit, and measurement as defined by the bar-code on the slide. The applications of this range from Tissue Micro Arrays to exhaustive scanning of entire slides (for subsequent viewing and qualitative/quantitative assessment and interpretation).
2. Sampling of two regions: This is a special, but frequently occurring situation, when using the physical disector. Here, the two sections are outlined, and image analysis is used to automatically obtain a perfect registration of the two sections. Subsequently, two image stacks (reference and look-up) are obtained using systematic random sampling of image fields in the two aligned sections.
3. Sampling over several sections is useful when e.g. a smooth fractionator has been used to obtain several tissue sections that are placed together in some embedding material and the entire volume is subsequently sectioned. Here, the system should be able to determine a sampling region that encompasses all image fields simultaneously. If image fields are sampled between tissue sections, it should be simple (using image analysis) to recognize this fact, and omit storage of images related to this field.

The imaging carried out during the sampling is preferably automated, such as comprising one or more of the following: Auto-focus, Auto-exposure and Auto-white balance (ii) Image Segmentation:

Image segmentation is the process of splitting an image into spatially well-defined regions or objects belonging to tissue or object classes of relevance to a specific application. Based on the segmented image, information such as number of objects, area, circumference etc can be measured. Thus, image segmentation is useful for the subsequent extraction of information from the image. Preferred methods for image segmentation include, but are not restricted to Thresholding, Bayesian Classification and K-Means clustering.

(iii) Disector Configuration

Various disector configurations known to one skilled in the art can be used. Parameters will depend upon the specific application, and can in one embodiment be stored in a configuration which can for example only be set up and modified by an administrator. Such parameters can e.g. include, but are not limited to, the following:

Objective for acquiring Superimages
Objective for acquiring intermediate resolution images
Objective for working resolution
Settings for condenser, filters etc for each of the objectives
Application specific metric for "goodness-of-registration"
Size of counting frame (iv) Quantifying Counting Events Objects, represented by counting events, are preferably quantified using an unbiased counting frame (see above).

To get the estimation of the total number of objects in the whole specimen, the fractionator principle can be used (see e.g. Howard & Reed). The principle of the fractionator is to take a known fraction, 1/x, of the whole specimen and count all objects, n, in that fraction, preferably using an unbiased counting frame. The unbiased estimate of the total number of particles in the whole object is then given by n times x.

Although a human operator can in one embodiment act to quantify the counting events—either partially by clicking on the events using a mouse or by manually counting the events, another embodiment of the present invention enables counting events to be counted using a signal counting device, such as e.g. VisioMorph.

Furthermore, assisted counting wherein suggested counting events are presented to the operator as described above, is also envisaged.

Computer Readable Medium

In another aspect, the present invention further encompasses a computer readable medium comprising instructions for carrying out one or more of the methods disclosed herein. Suitable computer-readable media can for example be a hard disk to provide storage of data, data structures, computer-executable instructions, and the like. Other types of media which are readable by a computer, such as removable magnetic disks, CDs, magnetic cassettes, flash memory cards, digital video disks, and the like, may also be used.

Automated System

In another aspect, the present invention further encompasses an automated or semi-automated system suitable for carrying out one or more of the methods disclosed herein, said automated or semi-automated system comprising, in combination:

a database capable of including a plurality of digital images of a plurality of biological specimens;
a software module for analyzing a plurality of pixels from a digital image of a biological specimen;
a control module comprising instructions for carrying out said method(s).

Said automated or semi-automated system can also further comprise one or more of: a slide loader, a barcode reader, a microscope (preferably motorized), and a stage (preferably motorized).

Several automated slide loaders are commercially available today, allowing for the automated loading of slides onto a motorized stage mounted on a microscope. Suitable systems are e.g. supplied by Olympus or TrestleCorp. Such loaders can be integrated to standard Windows based computers, have the ability to hold 100+ slides, and read a range of bar-code symbologies.

Integrating such a loader with the system allows unattended, high-volume sampling and digitization of microscopy slides, and with the application of bar-codes data management at a very high level can be fully integrated into the work process.

Often one slide may contain several tissue sections. The methods of the present invention can thus be used as a type of physical dissector, where e.g. at least two adjacent sections from the specimen are placed side by side on the slide.

The system according to the present invention may also include a linear encoder for z-axis control.

Using a fully automated microscope, it is possible to let the system switch between low and high magnification. By using low magnification, it is possible to obtain a "superlens" image providing an overview of the entire slide, and let the system automatically identify regions on the slide containing tissue, using image analysis.

The system may include an image processor and digitizer, and a general processor with peripherals for printing, storage, etc. The general processor can be an INTEL PENTIUM microprocessor or similar microprocessor based microcomputer, although it may be another computer-type device suitable for efficient execution of the functions described herein. The general processor can for example control the functioning and the flow of data between components of the device, may cause execution of additional primary feature signal counting algorithms, and handles the storage of image and classification information. The general processor can additionally control peripheral devices such as a printer, a storage device, such as an optical or magnetic hard disk, a tape drive, etc., as well as other devices including a bar code reader, a slide marker, autofocus circuitry, a robotic slide handler, the stage, and a mouse.

The image processor and digitizer preferably act to digitize images from the digital camera and can optionally performs a primary algorithmic classification on the images to filter out unwanted information. The image processor and the general computer may each access read-only and/or random access memory, as would be readily apparent to one skilled in the art, for the storage and execution of software necessary to perform the functions described relative to that processing component. Further, each component and includes circuitry, integrated circuit chips, etc. for the control of communication or data transfer over the data bus, as well as other functions typical of similar processors.

The system can additionally provide an opportunity for a user to provide guidance during the entity quantification process. For example, the user can specify a particular area of interest by selecting it on the screen. Typically, the super image is presented, and the user may select an area or areas via a pointing device (e. g., a mouse). Counting is then limited to only the selected area or areas. Such a feature can be particularly useful when the user recognizes that a certain area of the image relates to an image field of interest.

The system can also provide a way to eliminate a specified area or areas selected via a pointing device (e. g., a mouse).

Portions of the image within the specified area or areas (sometimes called "gated areas") is ignored when spots are counted.

Applications

The methods according to the present invention can be used in a number of applications. In a preferred embodiment the methods are used in histology, such as histology used in both discovery and safety pharmacology. For example, one can use the methods of the present invention to accurately estimate the mass, volume and number of Beta-cells in a biological specimen. In another embodiment, one can use the methods of the present invention to accurately estimate the number, volume, and size distribution of alveoli in a biological specimen. In another embodiment, one can use the methods of the present invention to accurately estimate cell proliferations and apoptosis in a biological specimen. Tissues that can be investigated using the methods of the present invention include, but are not restricted to, liver, lung, lymph (for e.g. immuno toxicity assays), or thyroid glands. The methods can also be used in analyses of reproductive toxicology.

In another embodiment of the present invention, the methods of the present invention can be used in developmental neurotoxicity studies. The developing brain can be affected by neurotoxic agents either as a primary target or indirectly. Developmental injuries often manifest themselves as subtle quantitative changes in cell numbers.

Unbiased stereological determination of a neuron using the methods of the present invention can assist in the elucidation of potential effects of developmental neurotoxicants: one can thus study the numbers of neurons as a potential new end-point in regulatory developing neurotoxicity testing, using the methods of the present invention.

DEFINITIONS

Biological sample derived from a biological organism, such as a tissue sample or a body liquid sample. In most embodiments the biological sample is a biological cell sample.

Marker is used in its normal meaning, i.e. the part of the sample that may be used to identify whether the sample represents a particular condition, normally a disease or a disorder. Markers may be located in or on cells in the sample, or may be located extracellularly, such as targets lining specific structures in the sample. The term marker is used interchangeably with the term target.

Sample is any type of sample, preferably the sample is a biological sample.

Staining is used in its normal meaning, i.e. an aid to visualize the targets. The staining stains the targets, either directly or indirectly, but preferably does not stain any other parts of the sample, thereby enhancing the visibility of the targets.

Target is used in its normal meaning, i.e. the part of the sample that may be used to identify whether the sample represents a particular condition, normally a disease or a disorder. As described below targets may be located in or on cells in the sample, or may be located extracellularly, such as targets lining specific structures in the sample. The term target is used interchangeably with the term marker.

Classify or classification is used in its normal meaning, ie. determining whether a specific sample belongs to one of two or more classes or groups. An example of classification is shown in the Examples wherein the severity of a breast cancer sample is found by classifying the sample in one of the four classes: 0, 1+, 2+, 3+. In one embodiment the classification is based on determination of intensity and/or connectivity as discussed herein.

A cancer diagnosis, both an initial diagnosis of disease and subsequent monitoring of the disease course (before, during, or after treatment) is conventionally confirmed through histological examination of cell or tissue samples removed from a patient. Clinical pathologists need to be able to accurately determine whether the sample representing the tumor is benign or malignant and to classify the aggressiveness of tumor if deemed to be malignant, because these determinations often form the basis for selecting a suitable course of patient treatment. Similarly, the pathologist needs to be able to detect the extent to which a cancer has grown or gone into remission, particularly as a result of or consequent to treatment, most particularly treatment with chemotherapeutic or biological agents.

Histological examination traditionally entails tissue-staining procedures that permit morphological features of a sample to be readily observed under a microscope. A pathologist, after examining the stained sample, typically makes a qualitative or semi-quantitative determination of whether the tumor sample is malignant. Sometimes also a quantification is performed, this is however conducted manually. It is difficult, however, to ascertain a tumors aggressive potential merely through histological examination of the sample, because a tumor's aggressive potential is often a result of the biochemistry of the cells within the tumor, such as protein expression or suppression and protein phosphorylation, which may or may not be reflected by the morphology of the sample. Therefore, it is important to be able to assess the biochemistry of the cells within a tumor sample. Cancer therapy can be based on molecular profiling of tumors rather than simply their histology or site of the disease.

Thus, not only the mere identification of stained targets but also the quantification of stained targets in a sample is relevant for providing a diagnosis, such as a cancer diagnosis.

The present invention provides methods for identifying, enhancing, and quantifying stained targets based on inventive filtering methods. The filtering methods are applied to digital representations of cell samples stained with a staining selective for the target to be visualised. Stained targets may be classified as blobs or lines.

Blobs means that the target appear in areas (often rounded) in the cells or outside the cells. Blobs may also be called spots. Blobs may represent anything from a single molecule to a group of molecules or even entire structures, such as nucleoli, nuclei or cells. Examples of targets presenting themselves as blobs are single or grouped proteins or peptides, such as lysozymes or a single receptor or groups of receptors.

Lines mean that the targets are arranged so that they appear as lines in the digital representation. Examples of targets appearing as lines are proteins or peptides, such as receptors, attached to the cell membrane essentially along the whole cell membrane. Lines may also be targets aligned along a structure or an organ in a tissue.

In the present context the term "representation" is used to describe a representation of the region to be examined, i.e. the term representation includes 1-dimensional representations, 2-dimensional representations, 3-dimensionals representations as well as n-dimensional representatives. Thus, the term representation includes a representation of the region, a volume of the region, a matrix of the region as well as an array of information of the region.

In the present context the term "background" is used to describe any other structure in the representation not representing the targets to be identified.

The present inventors have identified new filters suitable for enhancing blob-shaped and linear structures, respectively. The filtering method comprises applying filter constant(s) to the pixels in at least a subset of the digital representation of the sample. As described below, the filter constants may be determined so as to provide the polynomial coefficients of a spatial polynomial determined within a local window within the digital representation as a least squares fit to the intensity values within the said window. Preferably the polynomial is a second order polynomial, a fourth order polynomial, or a sixth order polynomial. Increasing orders of the polynomial will make the filters still more responsive to high-frequency content in the representation, and thereby also to noise. On the other hand, the local representation properties are also modeled far better by a higher-order polynomial. The choice of the polynomial order is therefore a trade-off, and may be chosen according to the specific application.

The number of filters may be selected depending on the specific application, however for most purposes it is preferred that at least three filter constants are applied to the pixels in the subset. The number of filter constants depends entirely upon the size of the window—i.e. the filter support.

The window size for the polynomial is preferably fitted to be greater than the size of the subset at the specific magnification used for obtaining the digital representation, and may be fitted for each representation, or more preferably a general fitted window size may be used for all representations in a series of representations having corresponding subset size, also called a universal window size.

The subset may correspond to any suitable portion of the digital representation, and the entire digital representation may be filtered in one embodiment.

When applying each of the filters in a sliding window across the digital representation or a subset of the digital representation, filtering process continues by determining an Eigensolution for each window location, thereby obtaining a filtered representation. By the term Eigensolution is understood Eigenvalue and/or Eigenvector.

In a preferred embodiment the Eigensolution is determined from a Hessian matrix wherein said Hessian matrix is generated from the Polynomial filters, as discussed below in greater detail. In particular the present inventor has found that the first Eigenvalue is suitable for enhancing locally linear structures, and the second Eigenvalue is suitable for enhancing blob-shaped structures.

Combining the filtered representation, optionally with the original spectral representation, the representation is then segmented into stained targets and background in order to obtain a segmented representation. The segmentation may be a simple thresholding process whereby the segmented representation shows the enhanced stained targets and has eliminated or substantially eliminated the background. In other embodiments, the segmentation may comprise a multivariate Bayes classifier, or a multivariate (fuzzy) K-means clustering. Based on the segmented representation the stained targets may be e further analysed, such as by quantifying characteristics associated with the stained targets.

The filtered representation may be normalized, such as normalized with the intensity representation, before any segmentation is initiated.

During the segmentation process the filtered representation may be combined with the digital representation in order to supply information from the digital representation to the segmented representation. This is particularly relevant when the digital representation contains information regarding for example colour of the staining.

The segmented representation may be post-processed before identifying the stained targets. In one embodiment the post-processing relates to elimination of stained cell membranes or stained cell blobs having an area below a predefined area whereby only the stained targets likely to be the relevant stained targets are identified.

In one embodiment the filter constants are estimated as described in the following.

The digital representation $g(x,y)$ has been sampled with sampling densities $\Delta_x$ and $\Delta_y$ respectively. The sampled signal is then approximated with a smooth function in a window that, for the sake of simplicity, is assumed to be square. For the particular application considered here, however, the special case of a P'th order spatial polynomial defined as below is considered:

$$f(x, y) = \sum_{k=0}^{P} \sum_{l=0}^{P-k} \theta_{k,l} x^k y^l = \Theta^T Z(x, y)^T \quad (0.1)$$

Where the vector notation is employed:

$$\underline{\Theta}^T = [\theta_{k,l}, k=0, \ldots, P\ l=0, \ldots, P-k] \quad (0.2)$$

and $$\underline{Z}(x,y)^T = [x^k, y^l, k=0, \ldots, P\ l=0, \ldots, P-k] \quad (0.3)$$

The coefficients of the polynomial may be determined using any suitable estimator, such as a Least-Squares estimator or a weighted Least-Squares estimator. The structure of a Least-Squares estimator is found as:

$$\hat{\underline{\Theta}} = \left( \sum_{i=-K}^{k} \sum_{j=-K}^{K} Z(i \cdot \Delta_x, j \cdot \Delta_y) Z(i \cdot \Delta_x, j \cdot \Delta_y)^T \right)^{-1} \quad (0.4)$$

$$\left( \sum_{i=-K}^{K} g(i \cdot \Delta_x, j \cdot \Delta_y) \underline{Z}(i \cdot \Delta_x, j \cdot \Delta_y) \right)$$

And the inverse coefficient matrix is:

$$\underline{B} = \left( \sum_{i=-K}^{k} Z(i \cdot \Delta_x, j \cdot \Delta_y) Z(i \cdot \Delta_x, j \cdot \Delta_y)^T \right)^{-1} \quad (0.5)$$

$$= \begin{pmatrix} b_{00} & b_{01} & \ldots & b_{0P} \\ b_{10} & b_{11} & \ldots & b_{1P} \\ \vdots & \vdots & \ddots & \vdots \\ b_{P1} & b_{P2} & \ldots & b_{PP} \end{pmatrix}$$

The coefficients can also be interpreted as a filter or convolution mask (used synonymously in the literature) with support on $[-K;K] \times [-K;K]$, where the filter has the form given below $$\Phi = \begin{pmatrix} \phi_{-K,-K} & \phi_{-K,-K+1} & \ldots & \phi_{-K,K} \\ \phi_{-K+1,-K} & \phi_{-K+1,-K+1} & \ldots & \phi_{-K+1,K} \\ \vdots & \vdots & \ddots & \vdots \\ \phi_{K,-K} & \phi_{K,-K+1} & \ldots & \phi_{K,K} \end{pmatrix} \quad (0.6)$$

And the filtered value is computed as $$G_\Phi(x, y) = \Phi \otimes g(x, y) \quad (0.7)$$

$$= \sum_{i=-K}^{K} \sum_{j=-K}^{K} g(x + i \cdot \Delta_x, y + j \cdot \Delta_y) \cdot \phi_{i,j}$$

Each coefficient in the approximating polynomial can be interpreted as a filter or convolution mask. The individual filter weights may be computed as $$\Theta_{m,n}(k,l) = \left(\frac{1}{\Delta_x}\right)^m \left(\frac{1}{\Delta_y}\right)^n \sum_{i=0}^{P} \sum_{j=0}^{P-i} \underline{B}_{\frac{(2P+3-m)m+2n}{2}, \frac{(2P+3-i)l+2j}{2}} (k)^i (l)^j \quad (0.8)$$

$$= \left(\frac{1}{\Delta_x}\right)^m \left(\frac{1}{\Delta_y}\right)^n \underline{B}_{\frac{(2P+3-m)m+2n}{2}, \square} Z(k,l)$$

Where the indices are running over $m=0, \ldots, P \quad k=-K, \ldots, K$ $n=0, \ldots, P-m \quad l=-K, \ldots, K$ (0.9)

The value of a given coefficient, ie. a filter constant, is now computed as $$\theta_{ij}(x,y) = \Theta_{ij} \otimes g(x,y) \quad (0.10)$$

$$= \sum_{k=-K}^{K} \sum_{l=-K}^{K} \Theta_{ij}(k,l) \cdot g(x-k, y-l)$$

For most practical applications it is suitable to use a second-order polynomial, as discussed in the following:

A spatial second-order polynomial defined on $(x,y) \in [-K; K] \times [-K;K]$ with $\Delta_x = \Delta_y = 1$, is defined as (Equation 0.1):

$$f(x,y) = \theta_{00} + \theta_{01}y + \theta_{02}y^2 + \theta_{10}x + \theta_{11}xy + \theta_{20}x^2 = \underline{\Theta}^T \underline{Z}(x,y)$$

with $\underline{\Theta}^T = [\theta_{00}, \theta_{01}, \theta_{02}, \theta_{10}, \theta_{11}, \theta_{02}]$ and $\underline{Z}(x,y)^T = [1, y, y^2, x, xy, x^2]$ The coefficient matrix is calculated as described in Equation 0.5, as shown below:

$$\sum_{x=-K}^{K} \sum_{y=-K}^{K} Z(x,y) Z(x,y)^T = \sum_{x=-K}^{K} \sum_{y=-K}^{K} \begin{pmatrix} 1 & y & y^2 & x & xy & x^2 \\ y & y^2 & y^3 & xy & xy^2 & x^2 y \\ y^2 & y^3 & y^4 & xy^2 & xy^3 & x^2 y^2 \\ x & xy & xy^2 & x^2 & x^2 y & x^3 \\ xy & xy^2 & xy^3 & x^2 y & x^2 y^2 & x^3 y \\ x^2 & x^2 y & x^2 y^2 & x^3 & x^3 y & x^4 \end{pmatrix} =$$

$$\frac{1}{3}(2K+1)^2(K+1)K \begin{pmatrix} \frac{3}{K(K+1)} & 0 & 1 & 0 & 0 & 1 \\ 0 & 1 & 0 & 0 & 0 & 0 \\ 1 & 0 & \frac{1}{5}(3K^2+3K-1) & 0 & 0 & \frac{1}{3}K(K+1) \\ 0 & 0 & 0 & 1 & 0 & 0 \\ 0 & 0 & 0 & 0 & \frac{1}{3}K(K+1) & 0 \\ 1 & 0 & \frac{1}{3}K(K+1) & 0 & 0 & \frac{1}{5}(3K^2+3K-1) \end{pmatrix}$$

The inverse coefficient matrix is obtained as:

$$\underline{B} = \frac{3}{(2K+1)^2 (2K+3)(2K-1)} \cdot \begin{pmatrix} \frac{1}{3}\left(\begin{array}{c}14K^2+\\14K-3\end{array}\right) & 0 & -5 & 0 & 0 & -5 \\ 0 & \frac{(2K+3)(2K-1)}{K(K+1)} & 0 & 0 & 0 & 0 \\ -5 & 0 & \frac{15}{K(K+1)} & 0 & 0 & 0 \\ 0 & 0 & 0 & \frac{(2K+3)(2K-1)}{K(K+1)} & 0 & 0 \\ 0 & 0 & 0 & 0 & \frac{3(2K+3)(2K-1)}{(K+1)^2 K^2} & 0 \\ -5 & 0 & 0 & 0 & 0 & \frac{15}{K(K+1)} \end{pmatrix}$$

Using this expression and Equation 0.8, the convolution masks corresponding to each of the coefficients in the polynomial are readily obtained.

$$\Theta_{00}(k, l) = \underline{B}_{00} \underline{Z}(k, l) =$$
$$\frac{1}{(2K+1)^2(2K+1)(2K-1)}((14K^2 + 14K - 3) - 15l^2 - 15k^2)$$

$$\Theta_{01}(k, l) = \underline{B}_{10} \underline{Z}(k, l) = \frac{3}{(2K+1)^2 K(K+1)} l$$

$$\Theta_{02}(k, l) = \underline{B}_{20} \underline{Z}(k, l) = \frac{15}{(2K+1)^2(2K+3)(2K-1)}\left(-1 + \frac{3l^2}{K(K+1)}\right)$$

$$\Theta_{10}(k, l) = \underline{B}_{10} \underline{Z}(k, l) = \frac{3}{(2K+1)^2 K(K+1)} k$$

$$\Theta_{11}(k, l) = \underline{B}_{10} \underline{Z}(k, l) = \frac{9}{(2K+1)^2 K^2 (K+1)^2} k \cdot l$$

$$\Theta_{20}(k, l) = \underline{B}_{20} \underline{Z}(k, l) = \frac{15}{(2K+1)^2(2K+3)(2K-1)}\left(-1 + \frac{3k^2}{K(K+1)}\right)$$

This local representation approximation may be used for extracting information about the local representation properties. The i,j'th order derivative is obtained using $$\frac{\partial^{ij}}{\partial^i x \partial^j y} f(x, y) = w(i) \cdot w(j) \theta_{ij}(x, y) \quad (0.11)$$

$$w(i) = \begin{cases} 1, & i > 0 \\ i, & i = 0 \end{cases}$$

In a preferred embodiment, after having applied the estimated filter constants to the representation, then the Hessian matrix may be established:

$$\underline{H}(x, y) = \begin{pmatrix} \theta_{20}(x, y) & \theta_{11}(x, y) \\ \theta_{11}(x, y) & \theta_{02}(x, y) \end{pmatrix} \quad (0.12)$$

And based on the Hessian matrix, the Eigen values may be computed as $$\begin{pmatrix} \lambda_1(x, y) \\ \lambda_2(x, y) \end{pmatrix} = \quad (0.13)$$

$$\frac{1}{2} \begin{pmatrix} \theta_{20}(x, y) + \theta_{02}(x, y) + \sqrt{(\theta_{20}(x, y) - \theta_{02}(x, y))^2 + 4\theta_{11}(x, y)^2} \\ \theta_{20}(x, y) + \theta_{02}(x, y) - \sqrt{(\theta_{20}(x, y) - \theta_{02}(x, y))^2 + 4\theta_{11}(x, y)^2} \end{pmatrix}$$

It is noted that $\lambda_1(x,y) + \lambda_2(x,y) = \theta_{20}(x,y) + \theta_{02}(x,y)$ may be recognized as the Laplacian. These new filters represent a non-linear combination of the directional derivatives. A simple interpretation of the first eigenvalue is that it is related to the maximum local curvature (more accurately the generalized variance), whereas the second eigenvalue is the curvature in a direction perpendicular to the first eigenvalue.

Accordingly, the first eigen filter enhances linear structures, such as cell membranes, whereas the second eigen filter has a tendency towards enhancing blob-shaped structures, such as grouped stained markers.

FIGS. 13a-13d show the advantages of using the filters of the present invention for enhancing stained targets associated with cell membranes, as compared to filters using Laplacian and a gradient.

Figure 13A:
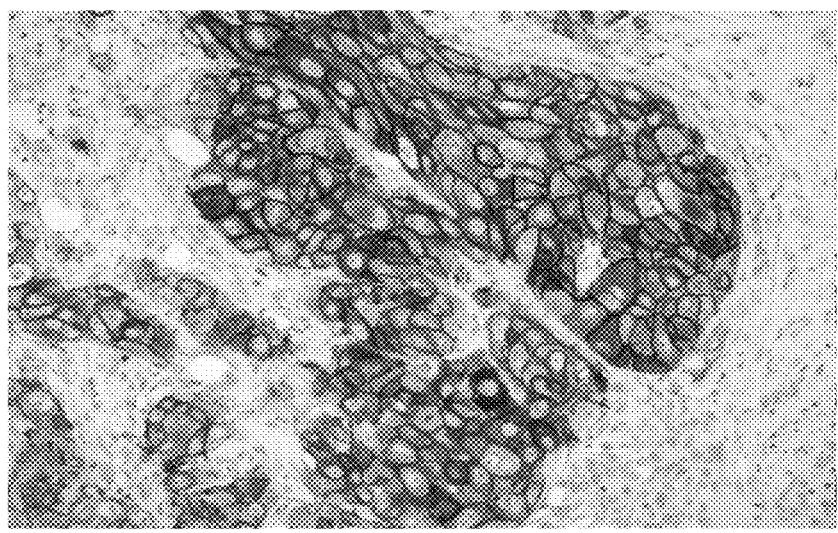
Figure 13B:
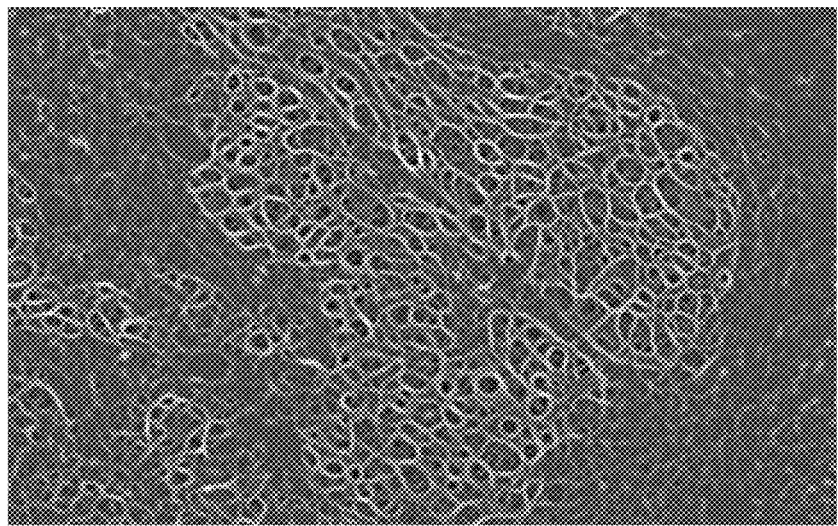

FIG. 13a shows the representation of a tissue sample, wherein a target associated with the cell membrane is stained. FIG. 13b shows the filtered representation, wherein a filter according to the invention relevant for cell membranes is used, ie. a filter using the first Eigenvalue of a Hessian matrix from a second order derivative. The stained cell membranes are clearly enhanced from the background.

Figure 13C:
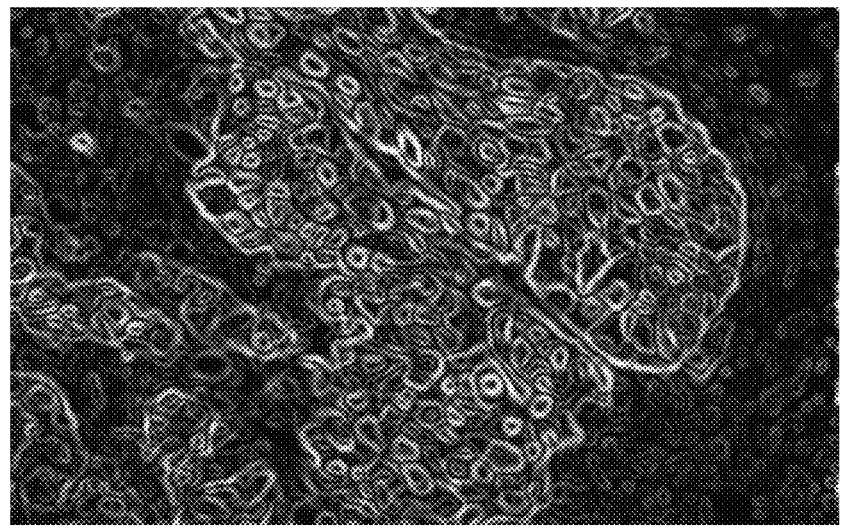
Figure 13D:
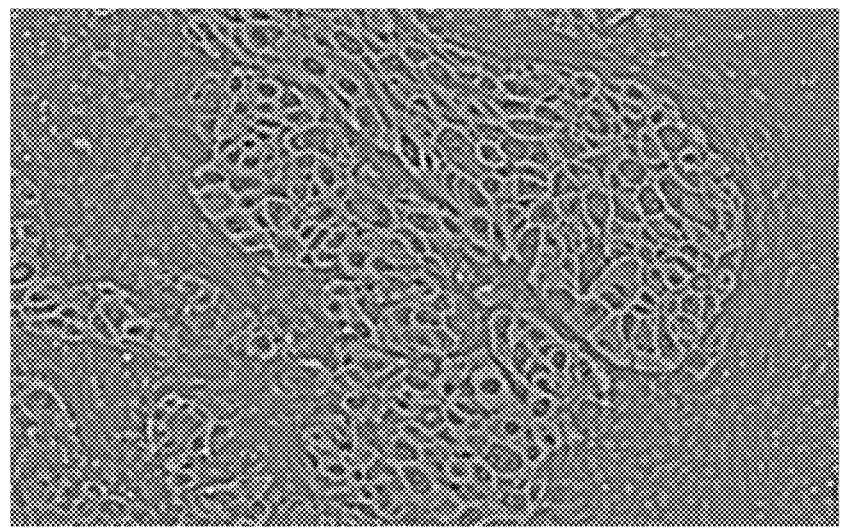

FIGS. 13c and 13d show the result of filtering with another filter, wherein FIG. 13c filters using a gradient (first order derivative)—note the "double lines" in relation to the cell membranes. In FIG. 13d a Laplacian filter is used, and it is clear from the figure that the result is a blurred representation as compared to the cell membranes in FIG. 13b.

FIGS. 14a-14d show an embodiment of the present invention. FIG. 14a shows a digital representation of a cell sample. FIG. 14b shows a filtered representation, being filtered with a method according to the invention using a second-order polynomial. FIG. 14c shows a segmented representation, and FIG. 14d shows the segmented representation after post-processing whereby stain areas having a size too small for being relevant cell membranes are removed. The stained targets may be identified from the segmented, post-processed representation of FIG. 14d and may furthermore be quantified.

Figure 14:
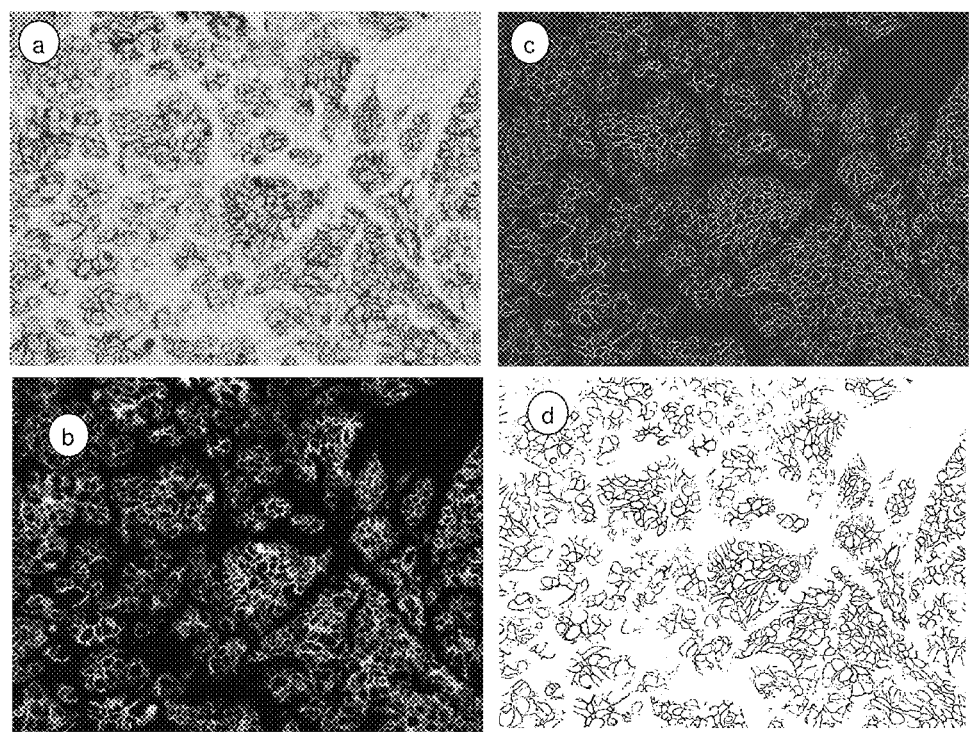

As shown in FIGS. 13 and 14 the present invention provides a method for enhancing stained targets, thereby facilitating identification of stained targets.

Apart from mere identification of stained targets in the digital representation the present invention is also useful for quantification of the stained targets in the digital representation, thereby providing the opportunity of classifying or grading the various cell or tissue samples based in the amount of stained target. For example in cancer diagnostics the amount of stained target may provide an important diagnostic tool informing of the severity of the disease. An example hereof is in the breast cancer diagnostics, wherein the quantification of stained Her-2 leads to a grading of the cell sample, and based on such a grading the physician is capable of determining the relevant treatment with a higher chance of success. For many purposes one type of targets are stained, such as one specific receptor. However, in some embodiments it is found advantageous to stain two different targets, such as two different receptors, normally by two different stains, each stain exclusively staining one target only. Thereby the methods according to the invention may identify the two different stained targets, normally in two different identification procedures, and subsequently quantification, classification etc may be conducted on the basis of the total information of the two targets.

The amount of stained target may be quantified by measuring the intensity of stained targets, such as the average staining intensity. The amount of stained target may also be determined by determining the diameter of each blob or the area of each blob, as well as determining the length of each line or the area of each line. The length of a cell membrane may for example be quantified by counting neighbouring pixels (measuring the skeleton of the cell membrane) not taking into account the thickness of the membrane.

In one embodiment chromaticity is used as a measure of the staining intensity. When studying cell membranes being stained it has been found that the red or blue chromaticity value is especially useful, more preferably red chromaticity value.

In another embodiment, the normalized so-called brown feature (defined below) is used as a measure of staining intensity.

The brown feature may be computed using simple manipulation of color contrasts as described below:

$F1$=Abs(Red-Blue)(The absolute value of the Red intensity minus the Blue intensity calculated pixel by pixel)

Normalized Brown=(255−(Blue+$F1$))/255

A different measure expressing staining intensity may be computed as follows: The staining intensity is divided into groups, such as three groups representing the strong intensity, the medium intensity as well as the weak intensity. By computing the area under curve for each group, getting for example $$A_{total}=A_{strong}+A_{medium}+A_{weak}$$

Different cut-offs in intensity may be defined for these.

Then relative values, such as $A_{strong}/A_{total}$ may be used as an alternative staining intensity measure.

It may also be possible to use Atotal=Astrong+Aother, where different cut-offs (thresholds) may be used to discriminate between Strong and Other depending on reagents, imaging, and other. As above, relative measures may be used.

The advantage of the approach outlined above is that it has the potential to decrease the need for having different diagnostic decision thresholds for different reagents (e.g. Dako, Ventana, Novocastra) when intensity measures are employed for diagnostic decision making.

In particularly when studying objects being defined by a line, such as cells being defined by the cell membrane, it may be advantageous to supplement with a measure for connectivity. Connectivity is used as a measure for defined objects wherein the lines defining the objects appears continuous in the image, such as for example when the cell membrane is stained in its whole circumference without any defects.

Connectivity may be measured as the area of lines continuously defining the objects divided by the number of connected cell membranes in the image: In other words the average size of connected positive stained membrane objects detected in the image see also Example 3 showing an embodiment of this. In particularly in cancer diagnostics wherein the amount of stained receptors or proteins on a cell membrane may be taken as a measure of severity of the disease, connectivity may add important information to the diagnostic.

In one embodiment the quantification is used for determining the expression level of a target in a biological cell sample, whereby the expression level is determined by either staining the mRNA or staining the resulting polypeptide and quantifying the stained targets, for example by determining the staining intensity. The staining intensity may thereby be a measure for the expression level of the target.

In another embodiment the methods according to the invention may be used to determine the presence of homodimers or heterodimers of receptors. In the tumor diagnostic HER2 is often used, and HER2 is in the family of VEGFR, namely HER1, HER2, HER3, HER4, each of which may form homodimers and heterodimers. In order to determine whether homodimers or heterodimers are formed, each receptor is stained with a different colour. It is then possible by the methods of the invention to determine the stained receptors and subsequently determine the colour of each staining, thereby determining whether the two receptors in the dimer are identical or different due to the colouring of the blobs representing the receptors.

Also there are recent methods, which only allow a staining to take place if two different targets are sufficiently close to each other. The Proximity Ligation Assay (PLA) (Proximity ligation assays for sensitive and specific protein analyses. Gustafsdottir S M, Schallmeiner E, Fredriksson S, Gullberg M, Söderberg O, Jarvius M, Jarvius J, Howell M, Landegren U. Anal Biochem. 2005 345(1):2-9.) for example can be made selective for heterodimers of HER-receptors if including two antibodies recognizing proximal epitopes on two different HER monomers. Only if the antibodies are bound simultaneously to their respective target, and are sufficiently close typically due to the heterodimerization of their targets, a staining reaction will be possible. In another embodiment the methods according to the present invention will, when applied to tissue samples stained by PLA or similar histochemical techniques, be of importance for the specific identification and quantification of only biologically active targets such as receptor heterodimers, phosphorylated receptors, ligand-binding receptors, and transcription factors bound to their corresponding DNA sequences.

In another embodiment the methods according to the invention allow for detection of amplification or deletion of a gene. This may be accomplished by staining a marker for the target gene and staining a marker for a reference gene typically but not necessarily located on the same chromosome as the target gene. Every gene copy will be represented by a specifically stained blob. If the ratio of target gene blobs to reference gene blobs is substantially higher than 1 it strongly indicates an amplification of that target gene. If the ratio of target gene blobs to reference gene blobs is substantially lower than 1 it strongly indicates a deletion of that target gene. Such detection of amplification or deletion may for example be relevant in the diagnosis of solid tumors, such as breast cancer, where for example HER-2 gene amplification has prognostic as well as Herceptin predictive consequences.

In yet another embodiment the methods according to the invention allow for detection of translocation of a gene. This may be accomplished by staining a marker for the gene and staining a marker being located next to the gene in the normal population. If the two markers are close, ie. seen as two markers next to each other then no translocation has happened, whereas if the two markers are found spaced apart from each other then it is likely that a translocation has happened. Such detection of translocation may for example be relevant in the diagnosis of lymphoma. The two markers may have the same staining or differently-coloured staining.

The present invention may also be used for determining co-localisation, ie. whether two stained markers are present in the same cell nucleus or in the cell nuclei of two neighbouring cells. This may for example be determined by determining the distance between the two stained markers.

The present invention may be applied to any cell sample. By the term "cell sample" is meant biological samples comprising cells, most preferably tumor cells, that are isolated from body samples, such as, but not limited to, smears, sputum, biopsies, secretions, cerebrospinal fluid, bile, blood, lymph fluid, urine and feces, or tissue which has been removed from organs, such as breast, lung, intestine, skin, cervix, prostate, and stomach. For example, a tissue sample can comprise a region of functionally related cells or adjacent cells. In one preferred embodiment, the specimen includes a plurality of cells, such as human cells, such as a plurality of human cells potentially including one or more human cancer cells, such as breast cancer cells.

In order to aid identify cells being relevant for the condition or disease being examined a staining specific for target(s) indicative for said condition or disease is applied to the sample before the digital representation is acquired.

The targets may be polypeptides, such as receptors, associated with the condition or disease capable of being visualised and optionally quantified by image analysis using a suitable and specific binding between the target and a molecule carrying the staining substance.

Examples of targets typically associated with the cell membrane are: the HER-family, ie. HER1, HER2, HER3, and HER4; cytokeratines; CD-antigens.

Examples of targets typically within the cell nucleus are: Estrogen receptor (ER), progesterone receptor (PR), androgen receptor (AR), Ki-67, and p53 as well as a high number of different gene targets involved in chromosomal aberrations (eg. Topoisomerase II alpha (TOP2A)).

Examples of targets typically found within the cytoplasm are: AKT, Mitogen-Activated Protein Kinase ("MAP kinase" or MAPK), PI-3 kinase, catenins, and MMPs.

Examples of targets typically also found extracellularly are: VEGFR, and TIMP-1.

Specific examples of targets include but are not limited to tumor antigens such as CA15-3 (breast cancer), CA19-9 (gastrointestinal and pancreatic cancer), CA125 (ovarian cancer), CA242 (gastrointestinal cancer), p53 (colorectal cancer), prostate-specific acid phosphatase (prostate cancer), prostate-specific antigen (PSA) (prostate cancer), Rb (retinoblastoma), CD56 (small cell lung cancer), prostate-specific antigen (prostate cancer), carcinoembryonic antigen (CEA) (colon cancer), melanoma antigen and melanoma-associated antigens (melanoma), mucin-1 (carcinoma), HER2 (breast cancer), HER2/neu (breast cancer) EGFR (breast and ovarian cancer), CA27-29 (breast cancer), nuclear matrix protein 22 (NMP22) (bladder cancer), bladder tumor-associated antigen (BTA) (bladder cancer), KIT (gastroinstestinal cancer), α-fetoprotein (αFP) (nonseminoma testicular cancer), n-human chorionic gonadotropin (βHCG) (testicular cancer), thyroglobulin (thyroid cancer) and fibrin/fibrin degradation protein (FDP) (bladder cancer).

The targets may also be gene products capable of providing a specific expression profile. For example in relation to metastasis phase of a tumor it is known that a specific gene expression profile may be found. By the present method it is possible to identify a gene expression profile and thereby determine the metastatic properties of a tumor or a metastasis found in a lymph node.

The targets may be detected directly, for example by using a primary antibody, or secondary by using an appropriate secondary antibody (such as rabbit anti-mouse IgG when using mouse primary antibodies) and/or a tertiary avidin (or Strepavidin) biotin complex ("ABC").

Examples of staining substances (also termed stains) include various enzymes, prosthetic groups, fluorescent materials, luminescent materials, bioluminescent materials, radioactive materials, positron emitting metals using various positron emission tomographies, and non-radioactive paramagnetic metal ions. The staining substance may be coupled or conjugated either directly to an antibody (or fragment thereof) or indirectly, through an intermediate (such as, for example, a linker known in the art) using techniques known in the art. Examples of labels that can be used include but are not limited to radiolabels such as $^3$H, $^{14}$C, $^{32}$P, $^{125}$I, $^{131}$I, $^{111}$In or $^{99}$Tc; fluorescent labels such as fluorescein and its derivatives, rhodamine and its derivatives, dansyl and umbelliferone; chemiluminescers such as luciferase and 2,3-dihydro-phthalazinediones; and enzymes such as horseradish peroxidase, alkaline phosphatase, lysozyme, glucose-6-phosphate dehydrogenase, and acetylcholinesterase. Antibodies can be tagged with such stains by known methods. For example, coupling agents such as aldehydes, carbodiimides, dimaleimide, imidates, succinimides, bisdiazotized benzadine and the like may be used to tag the antibodies with fluorescent, chemiluminescent or enzyme labels. The general methods involved are well known in the art. Specific examples of staining substances are e.g. antibodies against HER2/neu such as e.g the Herceptest from Dako, Pathway from Ventana and Novocastra from Novocastra Laboratories Ltd. Other example of staining substance is Vysis® LSI® TOP2A SpectrumOrange/HER-2 SpectrumGreen/CEP® 17 SpectrumAqua™ Probe from Abbott.

In another embodiment the targets may be nucleotides, such as detection of mutations in genes, for example point mutations. A specific binding between the target and the stain may be provided by a nucleotide probe being complementary to the nucleotide sequence to be detected. A staining molecule as discussed above may be coupled to the nucleotide probe by means as described above.

It is preferred that the sample is illuminated during acquisition of the digital representations, such as by using UV or illumination visible to the human eye.

Targets Associated with Cell Membranes

Figures 1, 2:
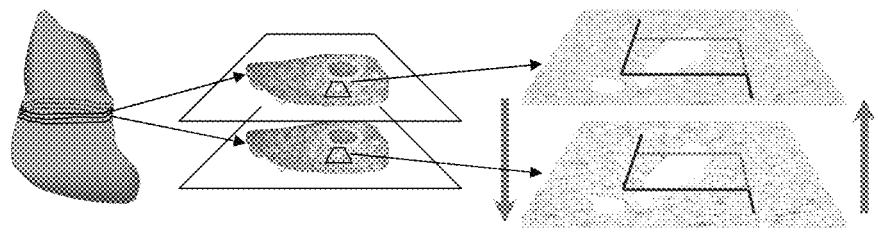
FIG. 1 shows that the sum of dimensions for probe and measured feature is always 3. E.g. with a line probe (1 dimension), it is possible to measure surface areas (2 dimensions).
FIG. 2 shows Adjacent sections are cut from the tissue, and corresponding positions in the two sections are examined to count events from first to second and from second to first section.
Figure 9B:
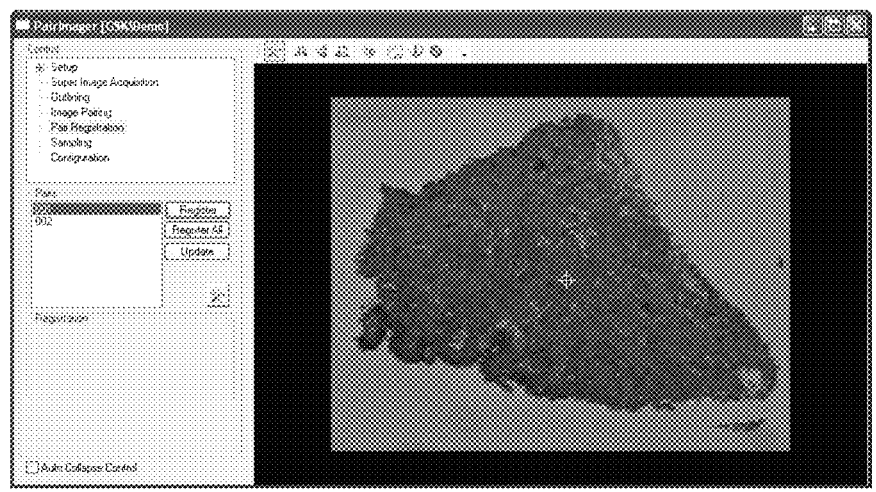
Figure 9C:
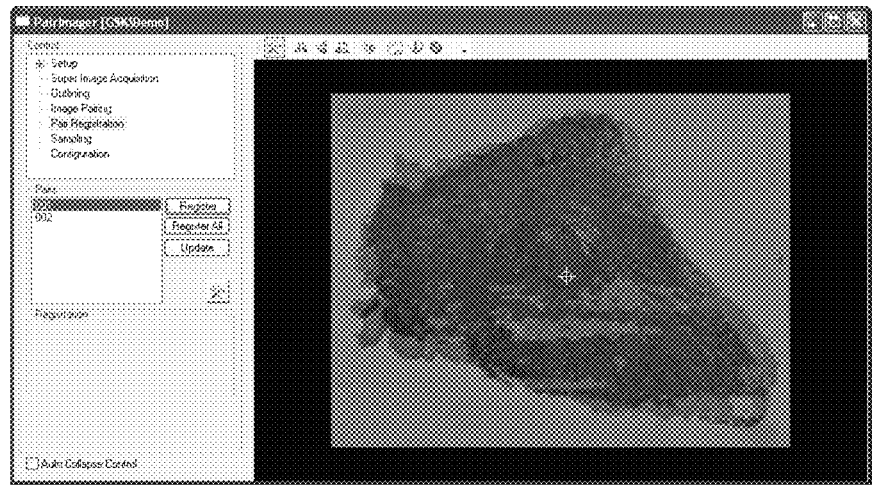
Figure 10B:
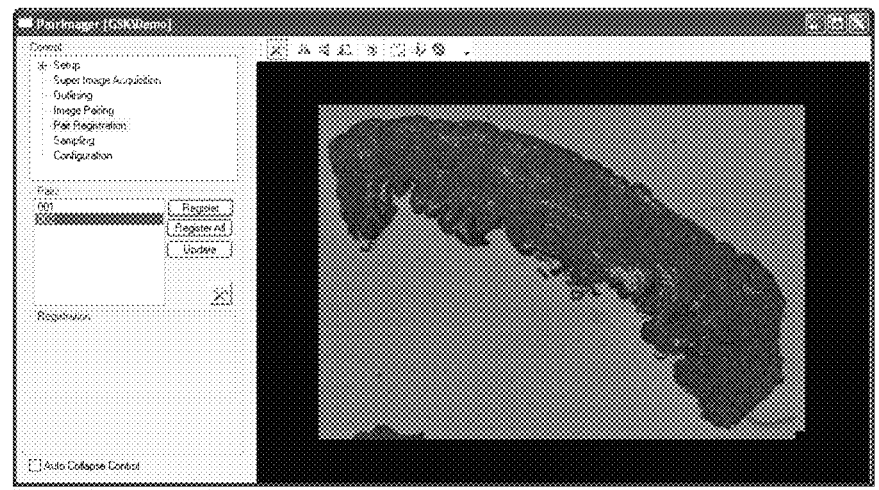
Figure 10C:
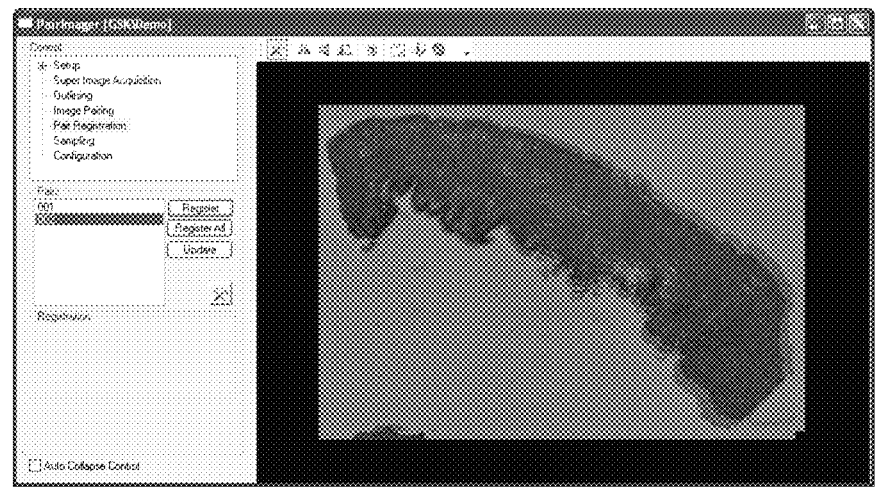
Figure 10D:
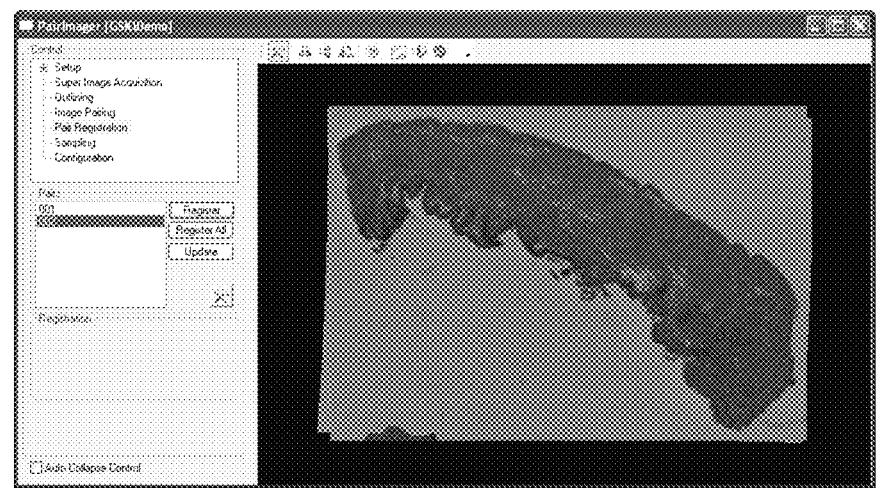

In one embodiment of the present invention the targets are associated with the cell membranes, such as receptors attached to the cell membrane. When the targets are stained the staining will appear as lines defining the cell membranes, see for example FIG. 1a. Any target associated with a cell membrane and capable of being stained may be identified using the present invention. Furthermore, the targets may also be quantified for example by determining the staining intensity, as described above, such as for example determination of chromaticity value, such as the red chromaticity and/or normalized brown, see above. Thus, the present invention allows for grading of the cell sample, wherein the grading may relate to the amount of targets present in the sample.

Example 1 shows an example of identifying stained targets associated with cell membranes, determination of the staining intensity and subsequent grading of the cell samples.

As discussed above, connectivity is also a measure that has proved to contribute (statistically) independent information about the patients disease status. Connectivity is relates to the area of membranes divided with the number of connected membranes, it membranes exhibiting a continuity in the image.

Furthermore, the various measures may be combined, such as a combination of chromaticity value and connectivity.

Targets Associated with Extracellular Linear Structures

In one embodiment of the present invention the targets are associated with linear structures outside the cell, such as receptors lining vessels or bronchi. When the targets are stained the staining will appear as lines defining the structures. Any target associated with a linear structure and capable of being stained may be identified using the present invention. Furthermore, the targets may also be quantified for example by determining the staining intensity, as described above. Thus, the present invention allows for grading of the cell sample, wherein the grading may relate to the amount of targets present in the sample.

Blob-Shaped Targets

Blob-shaped targets are targets being concentrated as a blob, for example targets being concentrated in small areas of the cell, such as in lyzosomes or the like, or such as detection of mutations in a gene, for example wherein only one target may be present per cell.

Blob-shaped targets may range from a single molecule corresponding to only a few pixels in the digital representation, to larger blobs giving rise to signals on several or many pixels, such as high locally arranged molecule concentrations, cell nuclei, whole cells, organelles or blob-shaped tissue structures.

Example 2 shows an example of identifying stained blob-shaped targets.

Diseases

The present invention may be applied to cell samples relating to a variety of diseases wherein a marker present in or on a cell is identifiable. Accordingly, the cell sample may originate from body fluids or tissue samples relating to for example the following diseases:

Breast cancer, gastrointestinal cancer, ovarian cancer, colorectal cancer, prostate cancer, retinoblastoma, lung cancer such as small cell lung cancer, skin tumors such as melanoma, nasopharyngeal tumors, bladder cancer, pancreatic cancer, testis cancer, nonseminoma testicular cancer, thyroid cancer, lymphoma, carcinoma in general.

In one embodiment the methods according to the invention may also be used for identifying whether a lymph node comprises metastatic tissue from a tumor, for example the first lymph node downstream from the tumor.

In one aspect the invention further relates to a method of classifying the sample based on the information obtained in the identification method discussed above. Accordingly, once stained targets in the sample has been identified the sample may be classified, for example classified as belonging to one of several classes as is the case in relation to cancer diagnostics, wherein the sample as discussed in the examples is allocated to one group or another depending on for example intensity and/or connectivity. Classification may be carried out using any suitable statistical means.

In one embodiment a general method of grouping the samples is based on classical multivariate discriminant analysis, such as a linear or quadratic Bayesian classifier, and regularized discriminant analysis, and in particular linear discriminant analysis, and quadratic discriminant analysis. By using such classifiers outliers are easily identified as having a low probability of belonging to any of the identified groups. Sometimes, this is referred to as a "reject class" in the literature. The method may also include an "outlier warning", ie. a warning that the sample seems to fit in neither of the defined groups, wherein the user of the system is warned that the sample represents problems, such as not comprising relevant tissue or the like. In one embodiment, only two features are used: Connectivity and staining intensity.

Classical discriminant analysis is described in e.g. "En introduction til Statistic, vol 2B, Knut Contadsen, IMM".

In another embodiment of classifying a sample is based on Classification and Regression Trees, as described in "Classification And Regression Trees, Breiman, Friedman, Ohlsen, Stone, Chapman & Hall, 1993". The basic underlying principle is a binary split on the features extracted from the image. In one embodiment, a first split is made on the connectivity feature thus splitting samples in "Positive" and "Negative". These two groups are then further split into classical diagnostic scores based on their intensity.

The digital representation may be acquired by any suitable method and system. In preferred embodiments, target staining is detected, measured and quantified using image analysis equipment, defined herein as for example comprising a light or fluorescence microscope, image-transmitting camera, or a virtual microscope (slide scanner) and a view screen, most preferably also comprising a computer that can be used to direct the operation of the device and also store and manipulate the information collected, most preferably in the form of optical density of certain regions of a stained tissue preparation. Image analysis devices useful in the practice of this invention include but are not limited to the system described in PCT/DK2007/050171.

In another aspect, the present invention further encompasses an automated or semi-automated system suitable for carrying out one or more of the methods disclosed herein, said automated or semi-automated system comprising, in combination:

a database capable of including a plurality of digital representations of a plurality of biological specimens;

a software module for analyzing a plurality of pixels from a digital representation of a biological specimen;

a control module comprising instructions for carrying out said method(s).

Said automated or semi-automated system can also further comprise one or more of: a slide loader, a barcode reader, a microscope (preferably motorized), and a stage (preferably motorized).

For example, the microscope can include motorized stage, an automated apparatus for focusing, for changing lens objectives between high and low magnification, and for adjustment of the light incident of the slide, as well as circuitry for controlling the movement of the motorized stage, typically in response to a command from the processing system. The microscope may also include an automated slide transport system for moving the slides containing the specimen to be classified on to and off of the motorized stage, and a bar code reader for reading encoded information from the slide. An example of a microscope performing at least some of these functions is manufactured by Carl Zeiss, Inc. of Germany, Leica Microsystems, Nikon, or Olympus. Several automated slide loaders are commercially available today, allowing for the automated loading of slides onto a motorized stage mounted on a microscope. Suitable systems are e.g. supplied by Ludl or Prior. Such loaders can be controlled by standard Windows based computers, and fitted to most standard research microscopes. They generally have the ability to hold 50+ slides, and some of them are fitted to read a range of bar-code symbologies.

Integrating such a loader with the system allows unattended, high-volume sampling and digitization of microscopy slides, and with the application of bar-codes data management at a very high level can be fully integrated into the work process.

Using a fully automated microscope, it is possible to let the system switch between low and high magnification. By using low magnification, it is possible to obtain a "superlens" representation providing an overview of the entire slide, and let the system automatically identify regions on the slide containing tissue, using image analysis.

The system may further include a general processor and peripherals for printing, storage, etc. The general processor can be a microprocessor based microcomputer, although it may be another computer-type device suitable for efficient execution of the functions described herein. The general processor can for example control the functioning and the flow of data between components of the device, and handles the storage of representation and classification information. The general processor can additionally control peripheral devices such as a printer, a storage device, such as an optical or magnetic hard disk, a tape drive, etc., as well as other devices including a bar code reader, a slide marker, autofocus circuitry, a robotic slide handler, the stage, and a mouse.

Preferably, the representations obtained are monochrome representations, color representations, or multi-frame (e.g. multispectral) representations. Representations are preferably stored as TIFF representations, or as JPEG or other standard formats.

In another embodiment the digital representation may be acquired from a virtual slide obtained by means of a virtual microscope imaging the cell sample in question. In this embodiment, the entire tissue area has been scanned at high magnification in e.g. a virtual slide scanner, and the resulting representation is already stored, for example on the harddisk. The system now handles this large representation as if it was controlling a microscope, stage, camera etc. Thus, the user can use the exact same interface to work with virtual microscope representations as when working with an actual microscope.

In another aspect the present invention relates to a method for providing a calibration curve. This is most generally accomplished by using cells, most preferably cultured cell lines, producing a consistent amount of the target that can be determined with high degrees of accuracy and precision. In preferred embodiments, a plurality of cell populations are assessed each expressing different amounts of the target. Such cell populations are used to determine the amount of target staining associated with varying amounts of target in the different cell populations. In the practice of the invention, the correlation between target staining and the amount of target expressed in a cell is expressed as a calibration curve relating the amount of target to a physical parameter, most preferably optical density, associated with target staining. The calibration curves produced according to and used with the methods of the invention are also advantageously expressed as an algorithm, most preferably in the form of a linear or logarithmic equation.

In yet another aspect the present invention provides a method for calibrating a system for identifying stained targets. For many applications both the identification of cells as well as the quantification of stained targets depends on a variety of parameters, such as the optics of the system, the light setting, the amount of staining used, the quality of staining used etc. Accordingly, in order to provide reliable results of the analysis of the cell sample it is of importance to evaluate and optionally calibrate systems regularly. In one aspect the calibration is carried out by performing the methods according to this invention using a standardized set of digital representations, in particular for evaluating the hardware settings of the system. The system is evaluated with respect to its ability of reproducing the correct results for identifying the stained targets and optionally also quantifying the stained targets.

In another aspect the parameters used, such as type and amount of staining, may be evaluated by staining either a standardized set of biological cell samples and performing the methods of identification and optionally quantification, or by staining a random set of biological cell samples and performing the methods of identification and optionally quantification on both the system to be evaluated and on a standardized system. Thereby it is possible to evaluate for example whether the correct amount of staining has been applied to the cell sample and the correct time for allowing the staining reactions to be performed. It is clear that too little staining or too much staining may lead to an incorrect identification as well as incorrect quantification of stained targets, thereby leading to an incorrect classification of the cell samples.

In the scenarios discussed above the calibration curve according to this invention may be used for evaluating the parameters and settings of the method and system.

Computer Readable Medium

In another aspect, the present invention further encompasses a computer readable medium comprising instructions for carrying out one or more of the methods disclosed herein. Suitable computer-readable media can for example be a hard disk to provide storage of data, data structures, computer-executable instructions, and the like. Other types of media which are readable by a computer, such as removable magnetic disks, CDs, magnetic cassettes, flash memory cards, digital video disks, and the like, may also be used.

REFERENCES

References disclosing aspects suitable for use in the methods of the present invention are as follows:—
[1] G. H Granlund, H. Knutsson (1995), Signal processing for computer vision, Dordrecht, Kluwer Academic Publishers. ISBN 0-7923-9530-1.
[2] C. V. Howard, M. G. Reed (1998), Unbiased Stereology Three dimensional measurements in microscopy, Oxford, BIOS Scientific Publishers. ISBN 1 85996 071 5
[3] B. Srinivasa Reddy, B. N. Chatterji (1996), An FFT-based technique for translation, rotation and scale invariant image registration. IEEE Transactions on Image Processing, 5(8) 1266-1271.
[4] P. R. Mouton (2002), Principles and Practices of Unbiased Stereology: An Introduction for Bioscientists. Baltimore, Md., USA: The Johns Hopkins University Press, p 9.
[5] B. Zitov a, J. Flusser (2003), Image registration methods: a survey. Image and Vision Computing, 21 977-1000.
[6] L. Gottesfield Brown (1992), A survey of image registration techniques. ACM Computing Surveys, 24(4) 325-376.
[7] I. Pitas (2000), Digital image processing algorithms and applications, John Wiley & Sons, Inc. ISBN 0 471 37739 2
[8] R. C. Gonzalez, R. E. Woods, Digital Image Processing, Upper Saddle River, N.J., Prentice Hall, Inc. ISBN 0-201-18075-8
[9] J. B: Antoine Mainz and Max A. Viergever, A Survey of Medical Image Registration, Medical Image Analysis (1998), Volume 2, pp 1-37.

EXAMPLES

Example 1: Image Acquisition

In one embodiment of the present invention, in order to make acquisition of disector pairs happen in an automated way, the system can run in two modes: the Preparation Mode and the Image Sampling mode. Examples of these modes are described below.

1. Preparation Mode

| Req. | Description |
|---|---|
| 1.1 | The operator loads the appropriate Disector confiquration |
| 1.2 | The operator is loading the specimen holder with up to eight (8) slides. The system requires operator-input regarding: STUDY ID Number of loaded slides in the specimen holder |

-continued

| Req. | Description |
|---|---|
| 1.4 | The system acquires Superimages for all loaded slides, according to the loaded disector configuration. Note: The system is equipped with auto white balance and auto-exposure in order to ensure optimal image quality |
| 1.5 | For each of the acquired superimages, the operator outlines the individual sections using masks. For each superimage, the user-defined masks have unique identifiers (e.g. a number). |
| 1.6 | When this process is completed, the system performs a first registration of all defined disector pairs based on pertinent the superimages. This will create a first rough registration that will be an important basis for a far more accurate registration at a higher resolution at a later stage in the process. Through the development process, the quality of this first crude registration will become known. Typically an accuracy of 1-2 pixels can be achieved. Note that this will translate into a larger, but known, error in a larger magnification. Hence, the process following from this point will be concerned with incremental improvements of the registration. |
| 1.7 | The operator has to approve the initial crude registration of all disector pairs. This initial registration can be modified manually by the operator, in order to assure that the basis for the subsequent high-level registration and image sampling is correct. |
| 1.8 | When all disector pairs has been registered in the superimage resolution, the system is ready for sampling mode. |

2. Image Sampling and Registration Mode

The steps described in the following are all running unattended.

2.1 Automated Refinement of Registration

It may turn out that this step can be omitted from some practical user applications.

| Req. | Description |
|---|---|
| 2.1.1 | The system automatically defines the outline (or meander) of each reference section for every disector pair. |
| 2.1.2 | Based on the information in the Disector configuration, the system automatically changes the objective to medium magnification (e.g. xIO magnification). |
| 2.1.3 | Fields Of View are sampled arbitrarily from the Reference section (R-FOV) for each given disector pair at medium resolution. Corresponding fields are found in the lookup section (L-FOV). For each corresponding R-FOV and L-. FOV a registration is carried out. |
| 2.1.4 | Based on the registration information obtained from the medium resolution images, the initial registration is further refined and updated. The resulting registration is used in the high resolution sampling described below. |

2.2 High-Resolution Sampling and Registration

| Req. | Description |
|---|---|
| 2.2.1 | The system automatically selects the objective corresponding to the (high) working resolution. |
| 2.2.2 | Using the Systematic random Sampling principle, the meander detected for each reference section, and the improved registration, the system now automatically identifies matching R-FOV and L-FOV images at full resolution. Based on the estimated image registration accuracy, the L-FOV is deliberately made sufficiently large (expanded) for ensuring that the R-FOV is fully matched/registered within this image. |
| 2.2.3 | Both R-FOV and L-FOV images are acquired and the final registration is computed. |

3. Data Management

| Req. | Description |
|---|---|
| 3.1 | All registered disector pairs L-FOV and R-FOV, acquired as described under section 2.2, are automatically stored in the database under the appropriate study and study unit as an integrated part of the image acquisition and registration process. |
| 3.2 | The Superimage related to a given disector pair is stored in the VIS database under the relevant study and study unit ID. |
| 3.3 | Offline, after image acquisition has been completed, the operator can locate and bring up any given disector pair for analysis and quantification. |

Example 2: Example of Image Quantification

Quantification can be carried out manually based on stereological principles, and can e.g. be carried out using a variety of software, such as newCAST. (Visiopharm A/S).

| Req. | Description |
|---|---|
| 1.1 | Starting in quantification mode, the system will automatically take the operator though the entire study going through slide-by-slide and FOV-by-FOV. |
| 1.2 | Disector pairs are presented to the operator with the counting frame overlaid the registered images. |
| 1.3 | The quality of the registration can be inspected in viewing mode, allowing the operator to overlay the two images in a separate window. The transparency of the top image can be altered. The overlay viewing capability should aid the user in identifying counting event. The R-FOV may be translated and/or rotated to further improve registration if required. |
| 1.4 | Counted events are stored and treated as usual in the newCAST system. |

Example 3: Example of General System Specification

Motorized microscope: Nikon 90i Objectives: ×2, ×IO (dry), ×20 (dry+oil), and ×40 (dry+oil) Camera outlet: c-mount Digital camera: Olympus DP70 Motorized stage: Prior H138 Specimen holder: 8-slides The system is capable of handling multiple sections per slide.

The system includes motorized stage with a specimen holder capable of holding up to eight slides. The Physical Disector modules are implemented and integrated on the VIS/newCAST platform, available commercially from Visiopharm A/S.

Example 4: Example of an Image Acquisition, Registration and Sampling

The image acquisition, registration and sampling may be carried out as described by the below work flow.

I: Start Visiopharm Integrator System (VIS)
1) Launch VIS (from the VIS icon on the desktop or Start menu | Programs | Visiopharm | VIS).

II: Recording Sample Images
1) Launch VIS (from the VIS icon on the desktop or Start menu | Programs | Visiopharm | VIS)
2) Open the Acquisition module.
3) Above the Launch button, Select AutomatedPhysicalDisector in the list.
4) Press the Launch button to open the automated physical disector dialog.
5) Select the Configurations page.
  a) Select the correct configuration.
  b) Press load button to load the configuration.

6) Select the 'Super Image' page.
   a) Under Super Images to capture, choose how many slides should be imaged.
7) Press the Start button. This starts the live view in the VIS window, and launches the ROI capture wizard dialog. Step through the wizard as described below.
   a) Check the Apply flat field correction box.
   b) Press Next>>.
   c) Ensure that the live image is in focus and correctly illuminated.
   d) Press Next>>.
   e) Use the joystick to move to a position on the slide where no tissue is seen, and where excess staining and other background variation is kept to a minimum.
   f) Press Next>>.
   g) The super Images are acquired automatically. Wait until acquisition has finished.
8) Select the Outlining page.
   a) Press classify button to launch the classification dialog.
   b) Ensure that the correct classification is selected.
   c) Press classify button again to segment the visible super image into tissue and background.
   d) Or press classify button to segment all super images in the list.
9) Select the Image Pairing page. Tissue sections are now displayed with boxes around them.
   a) Left click on the first section in a pair.
   b) Left click on the second section in a pair.
   c) The pair is added to the list.
   d) Repeat above for all section pairs.
   e) Select a pair in the list and press Rename to change the pair name.
   f) Select a pair in the list and press Delete to delete the selected pair.
   g) If all pairs should be redefined, press Reset to delete all pairs and replace the section boxes.
10) Select the Pair Registration page.
    a) Select a pair in the list.
    b) Press Register to match the two sections in the pair.
    c) Or press Register All to match all sections pairs in the list.
11) Select the Sampling page.
    a) Select a pair in the list.
    b) Press sample button to do a sampling in the selected pair.
    c) Or press sample all button to do a sampling in all pairs in the list.
12) The Specify Sampling Name dialog is shown.
    a) Write an ID name for the current sampling. Several samplings can be done on the same pair as long as they have different sampling IDs.
    b) Press OK.
13) The Automated Save dialog is shown.
    a) Specify where to store the sample images in the database. Only the two upper layers can be specified by the user, the third level will be automatically chosen based on the pair name and sampling ID.
    b) Press Enable.
14) The ROI capture wizard dialog is launched. Step through the wizard as described below.
    a) Check the Apply flat field correction box.
    b) Press Next>>.
    c) Ensure that the live image is in focus and correctly illuminated.
    d) Press Next>>.
    e) Use the joystick to move to a position on the slide where no tissue is seen, and where excess staining and other background variation is kept to a minimum.
    f) Press Next>>.
    g) The sample images are acquired automatically. Wait until acquisition has finished.
15) Select the Image approval page.
    a) Select the first image in the list. Verify that the image quality is ok.
    b) If the image quality is not ok, press Retake. This launches the ROI capture wizard and allows a retake of the current image.
    c) Use the Down arrow key to step through the list of images and ensure that all images are ok.
16) If all sampling has finished, close down the physical dissector.

III: Counting Sampled Images

1) In VIS open the newCAST module.
2) In the database, choose the measurement (third level) where the sampled images have been stored.
3) Press offline counting button to start a counting on the sampled images. This launches the Offline sampling setup dialog.
   a) Choose the sampling which should be counted.
4) The paired samples are shown side by side in a split screen view.
5) Press basic view button to select Basic imaging view mode that allows you to move the right image around.
6) If counting frames are used, click and hold left mouse button in the right image and drag the right image around until corresponding areas are seen inside the two counting frames.
7) Press count button to select the Count Tool mode that allows you to add count marks on the images.
8) Count the relevant events in the paired samples. Counts can be done in either of the two windows.
9) Press next button to go to the next sampling position.
10) Press prev button to go to the previous sampling position.
11) If the last sample has already been reached, pressing next button will launch the Meander sampling box.
    a) Press Finish to end the counting.
    b) Or press Repeat to start counting again from the first sample. Old counts will not be deleted.
12) Press measurement view button to open Data: View measurement Data. Select the different headings to the left to show corresponding data. The Quantities heading will show the counts made during sampling.
13) Press study view button to open Data: View study data. Select the first measurement in the study unit (level 2) of the database to show the total of all saved measurements.
14) When leaving the module or selecting a new measurement in the database a save dialog might appear depending on the settings of Data saving automation in the File/Preferences menu.

Example 5: Example Illustrating how Images can be Saved in a Database

Slide Image Naming

The image naming convention should preferably ensure that an alphabetic listing of the images shows pairs and paired sample positions consecutively. For each image acquisition session, a number of slides are imaged. These are stored in the database as measurements with the name: "Slide_ID"

ID. A user defined name describing the slide.

Paired Section Image Naming

On each slide a number of tissue sections are seen. These sections are paired and the pairs may be placed on the same slide or on different slides. The paired section images are registered and stored in the database as measurements with the names:

"PairN_1_ID"
"PairN_2_ID"

N. The number of the current section pair. This number is unique under the current study unit.

1 and 2. The number describing if it is the first or second image of the pair.

ID. A user defined name describing the slide.

Paired Sample Position Name

For each section, a number of corresponding positions in are imaged for each section pair. The paired sample position images are registered and stored in the database as measurements with the names:

"PairN_PosM_1_ID"
"PairN_PosM_2_ID"

N. The number of the current section pair. This number is specific under the current study unit.

M. The number of the current sample position in section pair N. This number is specific under the current section pair.

1 and 2. The number describing if it is the first or second image of the pair.

ID. A user defined name describing the slide.

Naming Example

The following example shows sampling of sections on two slides with reference to FIG. 12.

The slides area named "Test1" and "Test2" by the user. Two section pairs are found in the slides. One is on the same slide and one is on different slides. In each section pair, three positions are sampled. Due to registration uncertainty, a larger area is imaged for the second image of each pair.

In the database, the corresponding measurement names will be:

Slide Images:
  Slide Test1
  Slide Test2
Section Images:
  Pair1_1_Test1
  Pair1_2_Test1
  Pair2_1_Test1
  Pair2_2_Test2
Sample Position Images:
  Pair1_Pos1_1_Test1
  Pair1_Pos1_2_Test1
  Pair1_Pos2_1_Test1
  Pair1_Pos2_2_Test1
  Pair1_Pos3_1_Test1
  Pair1_Pos3_2_Test1
  Pair2_Pos1_1_Test1
  Pair2_Pos1_2_Test2
  Pair2_Pos2_1_Test1
  Pair2_Pos2_2_Test2
  Pair2_Pos3_1_Test1
  Pair2_Pos3_2_Test2

Example 6: Example of a Two-Step Registration Process

1) Registration with Rigid Warp.

Represent tissue sections as two binary images (pixel values 0 for background, 1 for object).

Calculate center of mass (CoM) of the two binary objects.

$$\text{Spatial moment } m_{pq} = \sum_i \sum_j i^p j^q f(i, j)$$

$$x_c = \frac{m_{01}}{m_{00}}, y_c = \frac{m_{10}}{m_{00}}$$

$$CoM = (x_c, y_c)$$

Calculate translation as difference in CoM.

Measure distance to object border from CoM as a function of sample angle for both objects. Sample at equidistant angles to create two digital signals Calculate displacement of one signal which minimizes the sum of squared differences (SSD) between the signals s1 and s2.

For displacement d:

$$SSD_d = \sum_n (s_1(n) - s_2(n))^2$$

Use the calculated displacement to calculate the rotation between images.

Translate and rotate image 2 using an image transformation matrix to fit the tissue sections on top of each other. For rotation S and translation (Tx, Ty), the transformation matrix for each image pixel is:

$$[x' \ y' \ 1] = \begin{bmatrix} \cos(\theta) & -\sin(\theta) & 0 \\ \sin(\theta) & \cos(\theta) & 0 \\ T_x & T_y & 1 \end{bmatrix} \begin{bmatrix} x \\ y \\ 1 \end{bmatrix}$$

2) Registration with Non-Rigid Warp

Use the images which have already been registered with rigid warp.

Define equidistantly spaced search areas inside tissue section in Image 1.

Inside each search area, detect the position of maximum pixel intensity variance.

Compare small area around this position with Image 2 to find areas of maximum covariance. Collect matching positions from the search areas in a list of match points.

From the N match points, create the normal equations:

$$\begin{bmatrix} x'_1 \\ \vdots \\ x_N \end{bmatrix} = \begin{bmatrix} 1 & f_1(x_1, y_1) & \dots & f_M(x_1, y_1) \\ \vdots & \vdots & \dots & \vdots \\ 1 & f_1(x_N, y_N) & \dots & f_M(x_N, y_N) \end{bmatrix} \begin{bmatrix} \alpha_{x1} \\ \vdots \\ \alpha_{xM} \end{bmatrix} + \begin{bmatrix} \varepsilon_1 \\ \vdots \\ \varepsilon_N \end{bmatrix}$$

$$\begin{bmatrix} y'_1 \\ \vdots \\ y_N \end{bmatrix} = \begin{bmatrix} 1 & f_1(x_1, y_1) & \dots & f_M(x_1, y_1) \\ \vdots & \vdots & \dots & \vdots \\ 1 & f_1(x_N, y_N) & \dots & f_M(x_N, y_N) \end{bmatrix} \begin{bmatrix} \alpha_{y1} \\ \vdots \\ \alpha_{yM} \end{bmatrix} + \begin{bmatrix} \varepsilon_1 \\ \vdots \\ \varepsilon_N \end{bmatrix},$$

where M is the number of different functions e.g. x, y, $x^2$, $x^2$, xy, which are used for the estimation.

Use a least squares estimation to calculate the a parameters, resulting in the following transformation matrix for each image pixels:

$$\begin{bmatrix} x' \\ y' \end{bmatrix} = \begin{bmatrix} \alpha_{x1} & \cdots & \alpha_{xM} \\ \alpha_{y1} & \cdots & \alpha_{yM} \end{bmatrix} \begin{bmatrix} 1 \\ f_1(x,y) \\ \vdots \\ f_M(x,y) \end{bmatrix}$$

Paired Sampling

When a sampling position has been determined in the first section of the pair, combine the rigid and none-rigid transformation to calculate the corresponding sampling position in the second section of the pair.

Capture high resolution sample images of the imaged specimen at the two positions. Capture a larger area for sample 2, to ensure that the area found in sample 1 can also be found in sample 2.

Use the rotation calculated for the rigid warp to rotate sample image 2.

Example 7a

Diagnostic Method for Breast Cancer

A set of 30 known cell samples were analysed according to the methods according to the invention, wherein a second-order polynomial was used in the filtering step.

The cell samples were all stained with a DAKO staining for HER2.

Each cell sample were analysed 5 times, except one that was only analysed four times. An average value was obtained for each cell sample. In table 1 the results are shown.

Furthermore, FIG. 15a-15c shows the correlation between red colour (RC), blue colour (BC), and saturation and the grade of the cell sample. It is seen that it is possible by the present method to classify the cell samples correctly. Grade 1 is a tumour with a good prognosis whereas grade 3 is a tumour with a poor prognosis.

TABLE 1

| Study Unit | Score | Measurement | ABC | ARC | SAT |
|---|---|---|---|---|---|
| H 4650 06 O 40x | 3 | 1 | 0.140305755 | 0.567683507 | 0.585557968 |
| H 4650 06 O 40x | 3 | 2 | 0.151161811 | 0.557879074 | 0.551546411 |
| H 4650 06 O 40x | 3 | 3 | 0.14499109 | 0.562841496 | 0.573876017 |
| H 4650 06 O 40x | 3 | 4 | 0.165196836 | 0.52702309 | 0.506042989 |
| H 4650 06 O 40x | 3 | 5 | 0.182473728 | 0.503168463 | 0.455627413 |
| H 12664 06 B 40x | 2 | 1 | 0.289148943 | 0.377945721 | 0.133820485 |
| H 12664 06 B 40x | 2 | 2 | 0.292537673 | 0.372403482 | 0.125716553 |
| H 12664 06 B 40x | 2 | 3 | 0.289834383 | 0.375007031 | 0.131340791 |
| H 12664 06 B 40x | 2 | 4 | 0.311560659 | 0.358334072 | 0.091828803 |
| H 12664 06 B 40x | 2 | 5 | 0.298739788 | 0.367848544 | 0.104750276 |
| H 11190 06 J 40x | 2 | 1 | 0.329677877 | 0.34808864 | 0.099567094 |
| H 11190 06 J 40x | 2 | 2 | 0.310383156 | 0.364080081 | 0.105611368 |
| H 11190 06 J 40x | 2 | 3 | 0.31277959 | 0.362776616 | 0.12463138 |
| H 11190 06 J 40x | 2 | 4 | 0.331907797 | 0.349275874 | 0.100380346 |
| H 11190 06 J 40x | 2 | 5 | 0.303526615 | 0.367602203 | 0.118081774 |
| H 11814 05 A 40x | 2 | 1 | 0.30872503 | 0.356608078 | 0.07782692 |
| H 11814 05 A 40x | 2 | 2 | 0.302595063 | 0.363145623 | 0.094440839 |
| H 11814 05 A 40x | 2 | 3 | 0.294105232 | 0.369438379 | 0.11926553 |
| H 11814 05 A 40x | 2 | 4 | 0.308142969 | 0.356703075 | 0.079978472 |
| H 11814 05 A 40x | 2 | 5 | 0.299503106 | 0.366127353 | 0.103437418 |
| H 12907 05 B 40x | 2 | 1 | 0.318690677 | 0.348493395 | 0.063654083 |
| H 12907 05 B 40x | 2 | 2 | 0.29088741 | 0.373213779 | 0.128868198 |
| H 12907 05 B 40x | 2 | 3 | 0.371845488 | 0.31328339 | 0.102853527 |
| H 12907 05 B 40x | 2 | 4 | 0.318884914 | 0.347447997 | 0.057761714 |
| H 12907 05 B 40x | 2 | 5 | 0.331902285 | 0.338986559 | 0.05583704 |
| H 8212 06 A 40x | 2 | 1 | 0.269985264 | 0.391596274 | 0.190342601 |
| H 8212 06 A 40x | 2 | 2 | 0.2818506 | 0.381505677 | 0.155941809 |
| H 8212 06 A 40x | 2 | 3 | 0.291310272 | 0.373774788 | 0.129128588 |
| H 8212 06 A 40x | 2 | 4 | 0.284903417 | 0.381298241 | 0.147392346 |
| H 8212 06 A 40x | 2 | 5 | 0.284313574 | 0.378709552 | 0.149573478 |
| H 8430 05 D 40x | 3 | 1 | 0.220128593 | 0.449771768 | 0.341499255 |
| H 8430 05 D 40x | 3 | 2 | 0.21602808 | 0.455042192 | 0.354338333 |
| H 8430 05 D 40x | 3 | 3 | 0.207081254 | 0.461939725 | 0.380258942 |
| H 8430 05 D 40x | 3 | 4 | 0.202042296 | 0.466157139 | 0.395570719 |
| H 8430 05 D 40x | 3 | 5 | 0.186272044 | 0.485685944 | 0.442756881 |
| H 10222 05 B 40x | 3 | 1 | 0.20320171 | 0.469126019 | 0.39278817 |
| H 10222 05 B 40x | 3 | 2 | 0.203162365 | 0.47419604 | 0.394844649 |
| H 10222 05 B 40x | 3 | 3 | 0.196486159 | 0.480168642 | 0.413802753 |
| H 10222 05 B 40x | 3 | 4 | 0.189671544 | 0.489105956 | 0.434415171 |
| H 10222 05 B 40x | 3 | 5 | 0.191102904 | 0.488797499 | 0.431137095 |
| H 6358 06 B 40x | 3 | 1 | 0.150253965 | 0.558724867 | 0.557084024 |
| H 6358 06 B 40x | 3 | 2 | 0.178672411 | 0.523306517 | 0.474585608 |
| H 6358 06 B 40x | 3 | 3 | 0.157711048 | 0.537353875 | 0.53165111 |
| H 6358 06 B 40x | 3 | 4 | 0.16595881 | 0.52868736 | 0.509417395 |
| H 6358 06 B 40x | 3 | 5 | 0.175191638 | 0.512331875 | 0.481347277 |
| H 22475 05 H 40x | 3 | 1 | 0.195962869 | 0.474760526 | 0.416017729 |
| H 22475 05 H 40x | 3 | 2 | 0.199597174 | 0.471095892 | 0.405727144 |
| H 22475 05 H 40x | 3 | 3 | 0.198193245 | 0.467701857 | 0.407815319 |
| H 22475 05 H 40x | 3 | 4 | 0.213086998 | 0.457734082 | 0.365583598 |
| H 22475 05 H 40x | 3 | 5 | 0.211296966 | 0.454381596 | 0.36828678 |
| H 11829 05 A 40x | 3 | 1 | 0.159795697 | 0.507786892 | 0.521505738 |
| H 11829 05 A 40x | 3 | 2 | 0.172249822 | 0.500165834 | 0.485185894 |
| H 11829 05 A 40x | 3 | 3 | 0.173029912 | 0.491409823 | 0.481595337 |
| H 11829 05 A 40x | 3 | 4 | 0.189604103 | 0.483853618 | 0.434177908 |

TABLE 1-continued

| Study Unit | Score | Measurement | ABC | ARC | SAT |
|---|---|---|---|---|---|
| H 11829 05 A 40x | 3 | 5 | 0.168216371 | 0.502042579 | 0.496929264 |
| H 12382 05 C 40x | 3 | 1 | 0.205618079 | 0.473458353 | 0.391156709 |
| H 12382 05 C 40x | 3 | 2 | 0.199398618 | 0.478800795 | 0.408408108 |
| H 12382 05 C 40x | 3 | 3 | 0.21710658 | 0.463320369 | 0.356559746 |
| H 12382 05 C 40x | 3 | 4 | 0.20960678 | 0.475403866 | 0.38273506 |
| H 12382 05 C 40x | 3 | 5 | 0.183849643 | 0.500065892 | 0.453851936 |
| H 11806 05 J 40x | 3 | 1 | 0.203283314 | 0.45588912 | 0.391076567 |
| H 11806 05 J 40x | 3 | 2 | 0.196744194 | 0.466754742 | 0.411288292 |
| H 11806 05 J 40x | 3 | 3 | 0.205551198 | 0.462144208 | 0.385715167 |
| H 11806 05 J 40x | 3 | 4 | 0.213007946 | 0.452398271 | 0.362783818 |
| H 11806 05 J 40x | 3 | 5 | 0.217614791 | 0.445272342 | 0.349399744 |
| H 11722 05 A 40x | 3 | 1 | 0.219002716 | 0.449313366 | 0.347731229 |
| H 11722 05 A 40x | 3 | 2 | 0.222866305 | 0.438887275 | 0.333604573 |
| H 11722 05 A 40x | 3 | 3 | 0.230230346 | 0.432447089 | 0.312284847 |
| H 11722 05 A 40x | 3 | 4 | 0.248358799 | 0.412072496 | 0.255467957 |
| H 11722 05 A 40x | 3 | 5 | 0.250379981 | 0.41791637 | 0.253545763 |
| H 17844 06 C 40x | 3 | 1 | 0.222292084 | 0.451961026 | 0.335998944 |
| H 17844 06 C 40x | 3 | 2 | 0.202035146 | 0.47425487 | 0.397728822 |
| H 17844 06 C 40x | 3 | 3 | 0.201253726 | 0.47473401 | 0.40000563 |
| H 17844 06 C 40x | 3 | 4 | 0.216225279 | 0.458464477 | 0.353899458 |
| H 17844 06 C 40x | 3 | 5 | 0.205067037 | 0.473600552 | 0.388624495 |
| H 11726 05 B 40x | 2 | 1 | 0.298271537 | 0.36698968 | 0.110033235 |
| H 11726 05 B 40x | 2 | 2 | 0.2842417 | 0.379561738 | 0.14811903 |
| H 11726 05 B 40x | 2 | 3 | 0.277563962 | 0.384615481 | 0.168062631 |
| H 11726 05 B 40x | 2 | 4 | 0.287125621 | 0.377043449 | 0.146115718 |
| H 11726 05 B 40x | 2 | 5 | 0.265134431 | 0.399042203 | 0.20628677 |
| H 10952 03 A 40x | 3 | 1 | 0.184967411 | 0.48609024 | 0.446111995 |
| H 10952 03 A 40x | 3 | 2 | 0.192790187 | 0.478772553 | 0.424700299 |
| H 10952 03 A 40x | 3 | 3 | 0.19794829 | 0.473258649 | 0.4086401 |
| H 10952 03 A 40x | 3 | 4 | 0.200437046 | 0.467097778 | 0.399956788 |
| H 10952 03 A 40x | 3 | 5 | 0.216579815 | 0.450142341 | 0.352215743 |
| H 5817 04 G 40x | 2 | 1 | 0.301166424 | 0.367159426 | 0.106130239 |
| H 5817 04 G 40x | 2 | 2 | 0.301575034 | 0.364589156 | 0.10021868 |
| H 5817 04 G 40x | 2 | 3 | 0.297012722 | 0.369092713 | 0.119559203 |
| H 5817 04 G 40x | 2 | 4 | 0.29800526 | 0.368204571 | 0.116936954 |
| H 5817 04 G 40x | 2 | 5 | 0.292247953 | 0.373160534 | 0.128561639 |
| H 8865 05 F 40x | 2 | 1 | 0.241927844 | 0.426840153 | 0.27883397 |
| H 8865 05 F 40x | 2 | 2 | 0.25824932 | 0.408350334 | 0.227945106 |
| H 8865 05 F 40x | 2 | 3 | 0.265280237 | 0.402178978 | 0.208689023 |
| H 8865 05 F 40x | 2 | 4 | 0.273876257 | 0.393193859 | 0.182303245 |
| H 8865 05 F 40x | 2 | 5 | 0.257352951 | 0.412421194 | 0.233259023 |
| H 9119 05 D 40x | 3 | 1 | 0.174901586 | 0.507571944 | 0.477875706 |
| H 9119 05 D 40x | 3 | 2 | 0.202752305 | 0.477618456 | 0.397791971 |
| H 9119 05 D 40x | 3 | 3 | 0.204345495 | 0.477318959 | 0.392699298 |
| H 9119 05 D 40x | 3 | 4 | 0.230819421 | 0.450055886 | 0.314668869 |
| H 9119 05 D 40x | 3 | 5 | 0.217002712 | 0.469372404 | 0.36163233 |
| H 10715 05 A 40x | 2 | 1 | 0.291148963 | 0.383435477 | 0.154143582 |
| H 10715 05 A 40x | 2 | 2 | 0.282437044 | 0.391072691 | 0.168642801 |
| H 10715 05 A 40x | 2 | 3 | 0.291924397 | 0.381190819 | 0.148297478 |
| H 10715 05 A 40x | 2 | 4 | 0.268868179 | 0.403949119 | 0.206289316 |
| H 10715 05 A 40x | 2 | 5 | 0.265657964 | 0.408430692 | 0.217770538 |
| H 14945 05 D 40x | 3 | 1 | 0.228908859 | 0.436912465 | 0.317034812 |
| H 14945 05 D 40x | 3 | 2 | 0.213792659 | 0.450036951 | 0.362187072 |
| H 14945 05 D 40x | 3 | 3 | 0.230156375 | 0.43062817 | 0.312041316 |
| H 14945 05 D 40x | 3 | 4 | 0.224409264 | 0.440552743 | 0.331385199 |
| H 14945 05 D 40x | 3 | 5 | 0.227695279 | 0.433836016 | 0.31996661 |
| H 15042 05 G 40x | 2 | 1 | 0.29583216 | 0.36725936 | 0.113896356 |
| H 15042 05 G 40x | 2 | 2 | 0.289672819 | 0.371765773 | 0.132547283 |
| H 15042 05 G 40x | 2 | 3 | 0.287081425 | 0.374626163 | 0.140283254 |
| H 15042 05 G 40x | 2 | 4 | 0.28865984 | 0.372701995 | 0.134652433 |
| H 15042 05 G 40x | 2 | 5 | 0.271806219 | 0.392465418 | 0.185780876 |
| H 7098 06 A 40x | 3 | 1 | 0.195878937 | 0.47618724 | 0.416877152 |
| H 7098 06 A 40x | 3 | 2 | 0.206356238 | 0.458938076 | 0.382339894 |
| H 7098 06 A 40x | 3 | 3 | 0.192499047 | 0.474694197 | 0.424720389 |
| H 7098 06 A 40x | 3 | 4 | 0.199909078 | 0.472256051 | 0.403440807 |
| H 7098 06 A 40x | 3 | 5 | 0.192738081 | 0.481664712 | 0.42483259 |
| H 6527 06 B 40x | 2 | 1 | 0.273418075 | 0.393712517 | 0.184539227 |
| H 6527 06 B 40x | 2 | 2 | 0.263329595 | 0.400435293 | 0.211960765 |
| H 6527 06 B 40x | 2 | 3 | 0.265325694 | 0.401007473 | 0.205918351 |
| H 6527 06 B 40x | 2 | 4 | 0.264939522 | 0.401250768 | 0.208643966 |
| H 6527 06 B 40x | 2 | 5 | 0.270099081 | 0.393861554 | 0.193270683 |
| H 7317 06 A 40x | 3 | 1 | 0.256799814 | 0.417619823 | 0.239548511 |
| H 7317 06 A 40x | 3 | 2 | 0.244048238 | 0.433914524 | 0.278686443 |
| H 7317 06 A 40x | 3 | 3 | 0.248967165 | 0.430928969 | 0.263236241 |
| H 7317 06 A 40x | 3 | 4 | 0.283980602 | 0.393214075 | 0.169838338 |
| H 11352 06 D 40x | 2 | 1 | 0.303330724 | 0.363630697 | 0.092935256 |
| H 11352 06 D 40x | 2 | 2 | 0.306055868 | 0.36126552 | 0.092599157 |
| H 11352 06 D 40x | 2 | 3 | 0.296844913 | 0.369617522 | 0.118739232 |

TABLE 1-continued

| Study Unit | Score | Measurement | ABC | ARC | SAT |
|---|---|---|---|---|---|
| H 11352 06 D 40x | 2 | 4 | 0.291740809 | 0.374387005 | 0.125719177 |
| H 11352 06 D 40x | 2 | 5 | 0.290331189 | 0.373914984 | 0.133529355 |
| H 11090 06 C 40x | 2 | 1 | 0.26144462 | 0.406075197 | 0.218903503 |
| H 11090 06 C 40x | 2 | 2 | 0.274180245 | 0.390271194 | 0.180417925 |
| H 11090 06 C 40x | 2 | 3 | 0.272621456 | 0.391533093 | 0.18335394 |
| H 11090 06 C 40x | 2 | 4 | 0.266492356 | 0.401398527 | 0.202728217 |
| H 11090 06 C 40x | 2 | 5 | 0.282473493 | 0.384371374 | 0.154620693 |
| H 13035 06 C 40x | 2 | 1 | 0.275450451 | 0.390620895 | 0.175340271 |
| H 13035 06 C 40x | 2 | 2 | 0.284588958 | 0.382158062 | 0.150547389 |
| H 13035 06 C 40x | 2 | 3 | 0.283183158 | 0.384694148 | 0.161380194 |
| H 13035 06 C 40x | 2 | 4 | 0.304996164 | 0.362969751 | 0.099189372 |
| H 13035 06 C 40x | 2 | 5 | 0.294567178 | 0.372374012 | 0.124176044 |
| H 18862 06 A 40x | 2 | 1 | 0.260942008 | 0.408383572 | 0.221704201 |
| H 18862 06 A 40x | 2 | 2 | 0.269218561 | 0.398061776 | 0.195438986 |
| H 18862 06 A 40x | 2 | 3 | 0.266538675 | 0.405296572 | 0.205340154 |
| H 18862 06 A 40x | 2 | 4 | 0.265228482 | 0.400978097 | 0.206900393 |
| H 18862 06 A 40x | 2 | 5 | 0.264317323 | 0.400954955 | 0.208827032 |

Example 7b

Diagnostic Method for Breast Cancer

A set of 12 known cell samples were analysed according to the methods of the invention, wherein a second-order polynomial was used in the filtering step.

The cell samples were all stained with a cocktail of commercially available staining reagents for HER2.

Table 2 shows the results for the cell samples, and FIG. 16 shows the correlation between the clinical score and the quantitative score.

FIGS. 17a-b show the digital representations and the segmented representation, respectively, for clinical grad 0, 1+ and 3+. The digital representations are the left-hand representations.

TABLE 2

| Grade | ABC | AGC | ARC | Avg. Staining |
|---|---|---|---|---|
| 2 | 0.161488678 | 0.328537166 | 0.51562247 | 0.920557142 |
| 2 | 0.09887526 | 0.304347813 | 0.619136841 | 0.985191677 |
| 0 | 0.260744115 | 0.331384003 | 0.410530051 | 0.753248397 |
| 0 | 0.259839211 | 0.335294127 | 0.406137975 | 0.756244349 |
| 2 | 0.13852593 | 0.326704532 | 0.541695068 | 0.939668418 |
| 3 | 0.079267684 | 0.290178567 | 0.653341306 | 0.989884713 |
| 3 | 0.070623882 | 0.259615391 | 0.697310056 | 0.989889103 |
| 2 | 0.128698236 | 0.321285129 | 0.56101454 | 0.953971443 |
| 3 | 0.076289411 | 0.270370364 | 0.673424598 | 0.985081878 |
| 1 | 0.191981334 | 0.340292275 | 0.472722819 | 0.859086392 |
| 2 | 0.140973882 | 0.33502537 | 0.531151861 | 0.947177976 |
| 3 | 0.067544966 | 0.269360274 | 0.690039906 | 0.985041225 |

Example 8

Identification of Blob-Shaped Targets

Figure 18A:
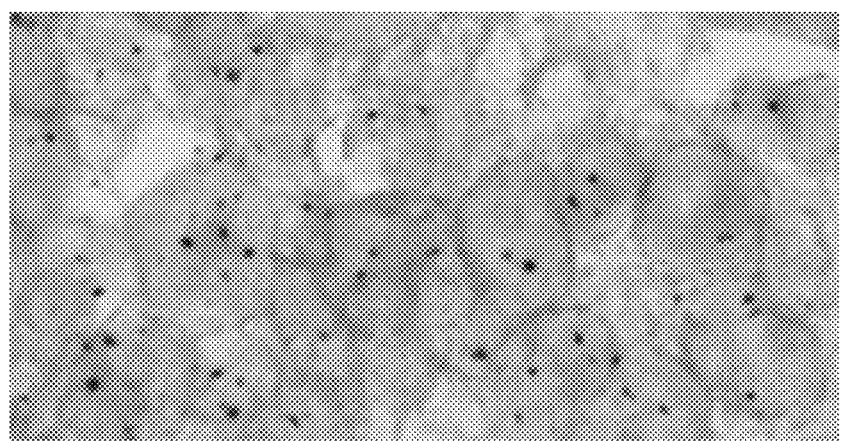

FIG. 18a shows the digital representation of a cell sample wherein blob-shaped targets are stained. The digital representation is subjected to the filtering step of the present invention using a second-order polynomial.

Figure 18B:
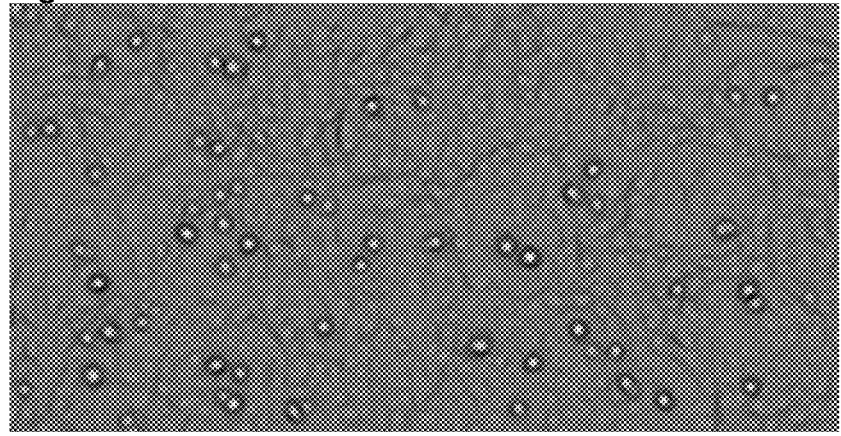

FIG. 18b shows the filtered representation wherein the second Eigen-value of Hessian Matrix is extracted from Green colour band.

Figure 18C:
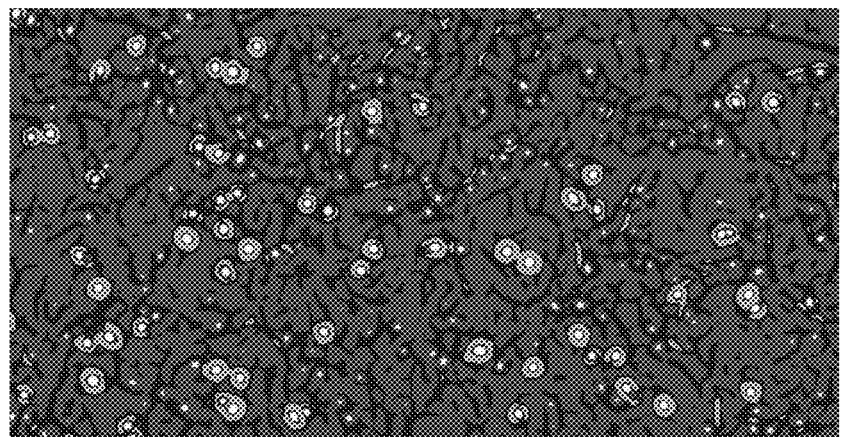

Then the segmentation step is initiated. FIG. 18c shows the responses, wherein Green is lowest response, Blue second lowest, Red, Second highest, Yellow Highest response.

Figure 18D:
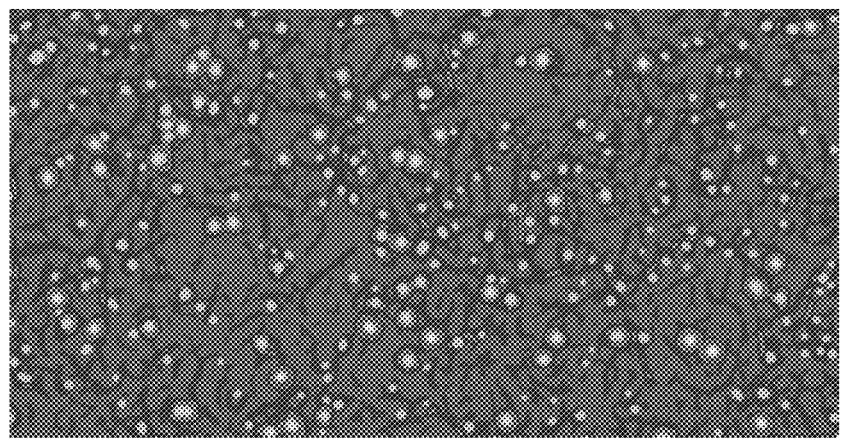

In FIG. 18d the highest response (yellow) is dilated to make sure it touches the Green halo (a sign that it is an admissible signal).

Figure 18E:
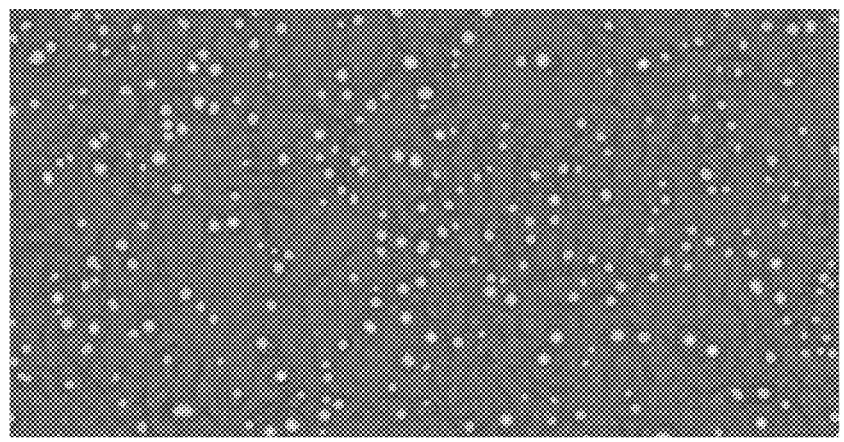

Background is removed in FIG. 18e, only signals with and without halos are preserved.

Figure 18F:
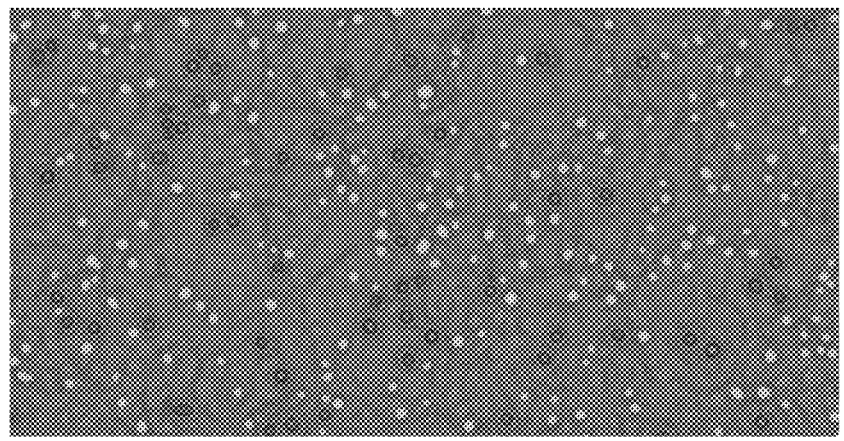
Figure 18G:
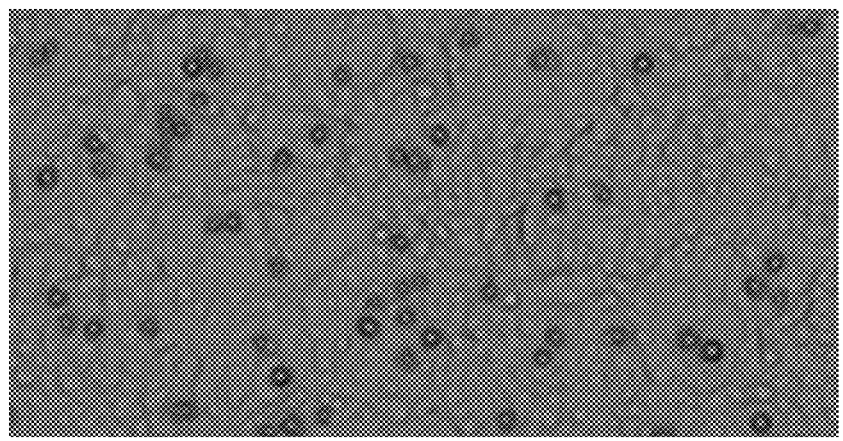

In FIG. 18f all cellular targets with a green halo is identified, and in FIG. 18g only the cellular targets with a halo are kept.

Figure 18H:
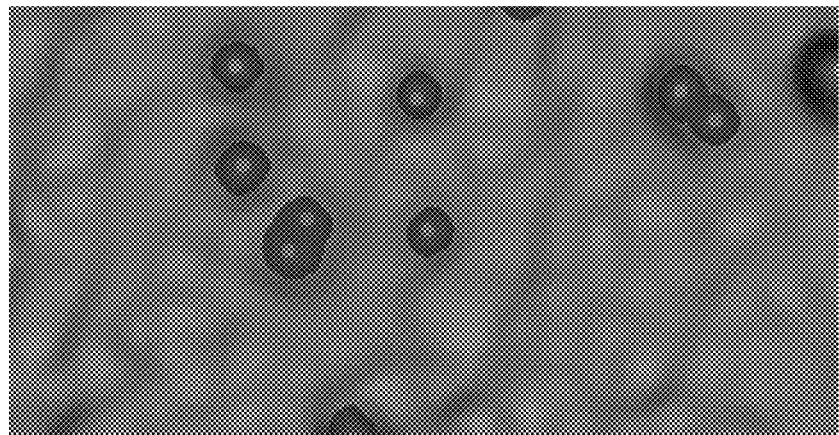

In FIG. 18h the filtered Eigen-value response is used to separate merged cellular targets, by identifying local extrema (maxima) in the response within an identified "object".

Figure 18I:
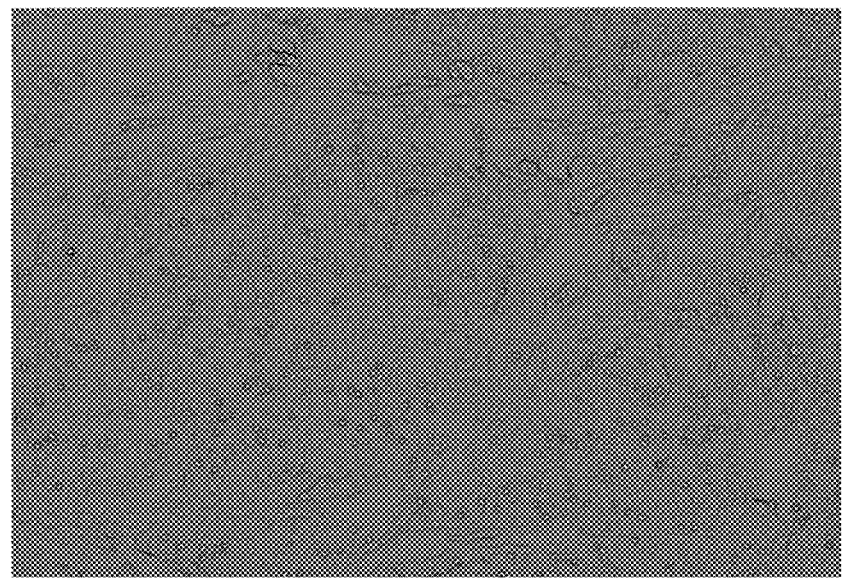

FIG. 18i shows all the identified stained targets.

Figure 18J:
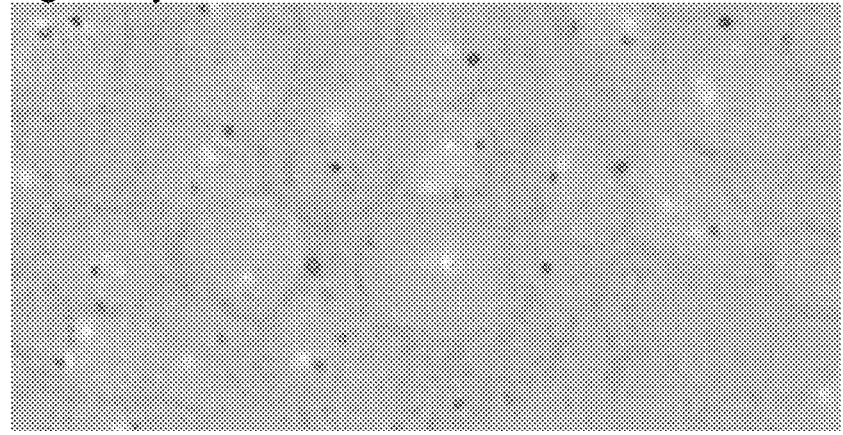

In FIG. 18j the red chromaticity is used to determine the type of a given cellular target. This is done by thresholding.

Figure 18K:
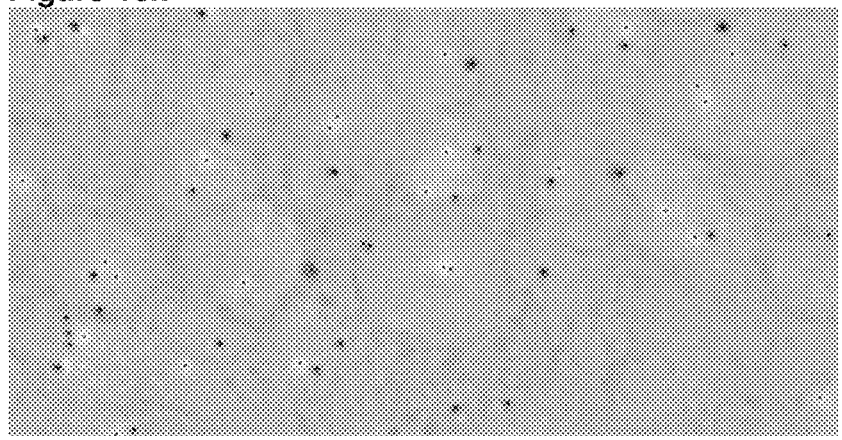

The result of the identification process is shown in FIG. 18k, wherein red stained targets and blue stained targets are shown. The result is then ready for quantification, such as counting of different types of cellular targets.

Example 9

Diagnosing Breast Cancer Using a Measure for Connectivity

On a set of known breast cancer samples analysed according to the methods of the invention a measure for connectivity was calculated. The breast cancer samples were stained with Herceptest and Pathway, respectively The measure for connectivity was calculated as the (log) average size of connected membrane objects, ie as the area of detected cell membranes divided with the number of connected cell membrane objects in the image, computed as log(1+AMEM/NMEM). Adding 1 under the log operator is performed to safeguard computations for in case the area and number of objects may become zero. In such cases, the connectivity is defined as zero.

The purpose of the connectivity measure is to discriminate between Negative cases (0, and +1) and Positive cases (+3 and possibly +2).

In FIG. 19a and FIG. 19b connectivity is plotted versus (manual) clinical score for each threshold level (T=1, 2, 3, and 4) for both Herceptest and Pathway.

The Membrane identification threshold that seems to work uniformly best for both reagents, in terms of connectivity, is the T=2 threshold.

A connectivity index around 5.6-5.7 seems ideal for separating 0 and +1 cases from the rest.

There are two obvious outliers for score=1 in the Pathway test. One appears to be an error in the manual scoring (should have been a +2), which is consistent with the fact that the same tumor specimen was scored 2 for the Herceptest, and the FISH amplification is ~1.5. The other outlier may be due to inclusion of in-situ areas in the analysis.

In FIG. 19c a comparison of the results for Herceptest and Pathway is seen. With the current measure of connectivity, the ideal cut-offs for both Herceptest and Pathway seems to be:
Negative (0 or +1) if Connectivity ≤5.7
Positive (+2 or +3) otherwise.

Accordingly, by adding a measure of connectivity to the analysis the samples may be divided into groups corresponding to the manual grading.

Example 10

Diagnosing Breast Cancer Using a Determination of Red Chromaticity.

On the same samples as used in Example 9, the Median Red Chromaticity (MRC) is plotted for the Herceptest and the Pathway data. This measure appears to be more robust than Average Red Chromaticity (ARC).

Figure 20A:
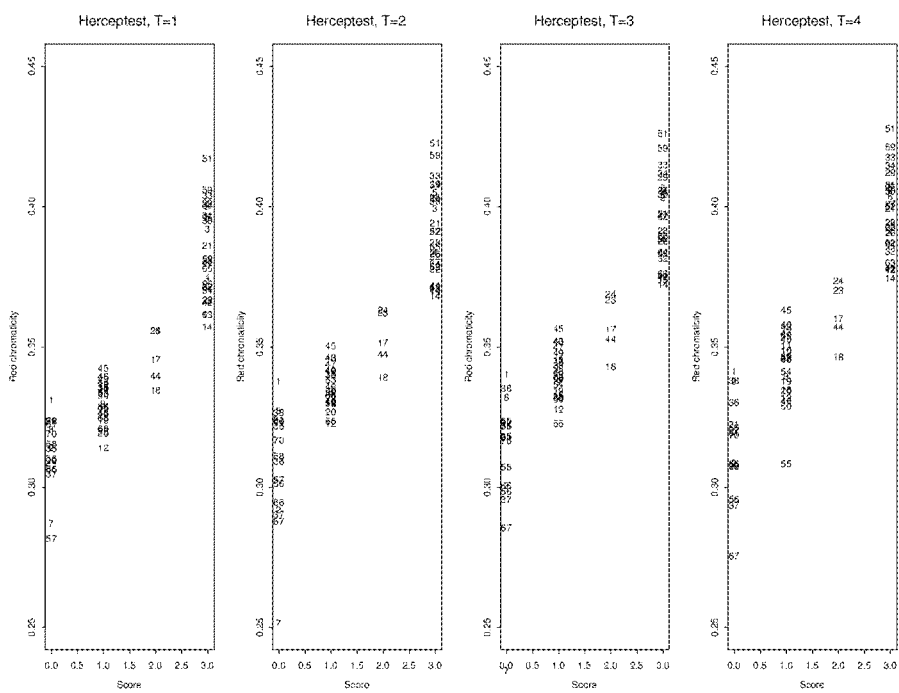
Figure 20B:
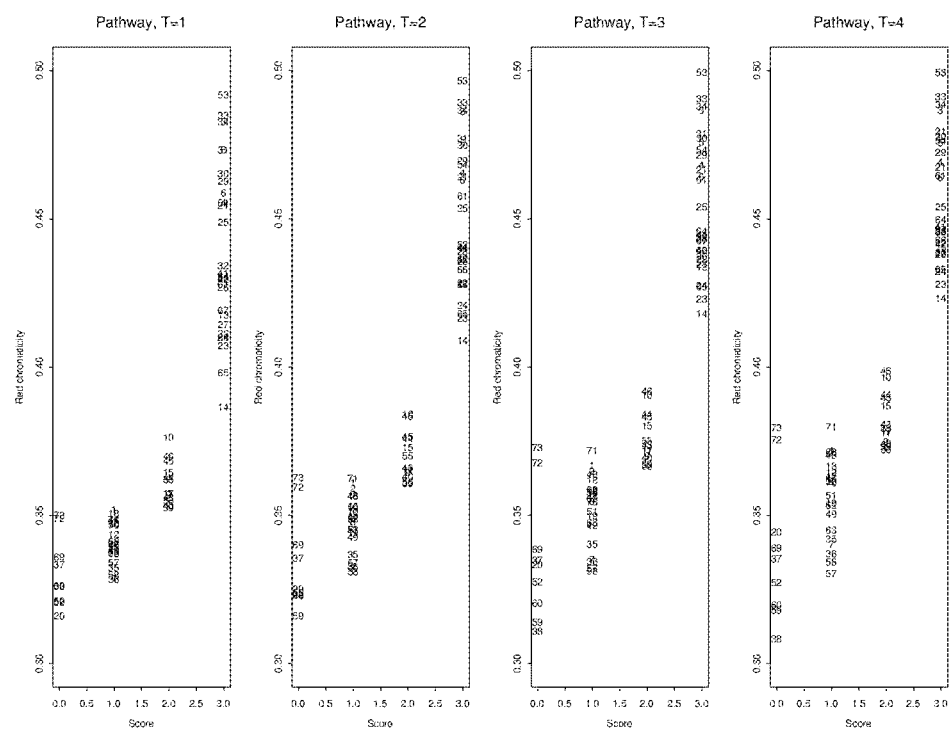

FIGS. 20a and 20b shows MRC is plotted versus (manual) clinical score for each threshold level (T=1, 2, 3, and 4) for both Herceptest and Pathway. It is noticed that chromaticity values for Pathway are generally higher than those observed for Herceptest, which is consistent with the empirical observation that Pathway specimens are generally darker than Herceptest specimens.

It is also noticed that the overall ability for MRC to separate the different classes is better for Pathway than it is for Herceptest.

For Herceptest, the ability to discriminate between +1 and +2 is not particularly good. If however, the connectivity measure has been used for separating (0 and +1) from (+2 and +3), MRC appears well suited for discriminating within these two groups. For Pathway, it is not obvious that Connectivity contributes independent statistical information of use for discriminating between the diagnostic categories—for this dataset. There is, however, reason to suspect that the variability between different labs and batches would make the combination more robust in general.

Figure 20C:
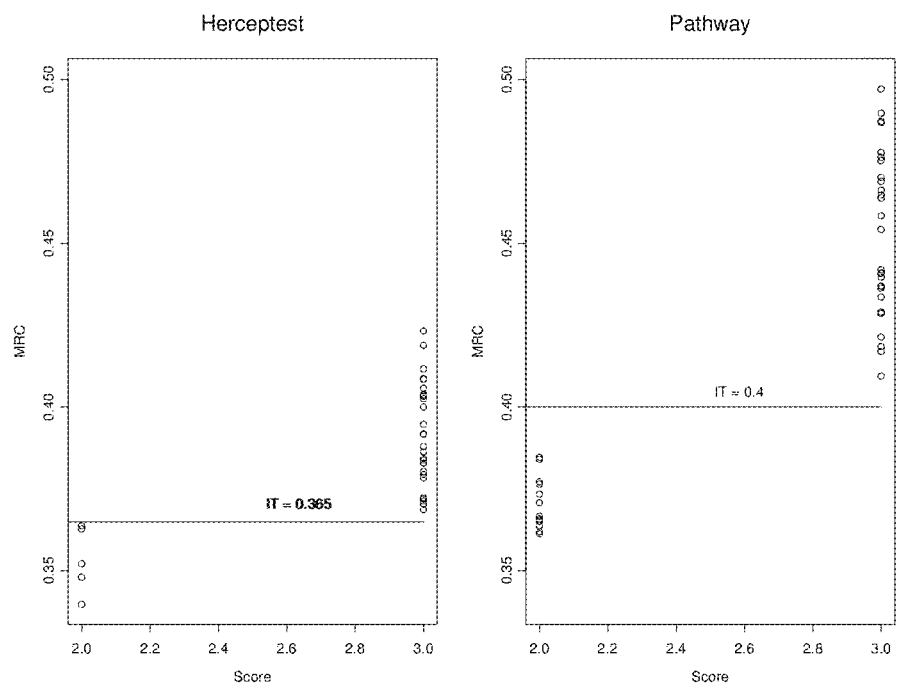
Figure 20D:
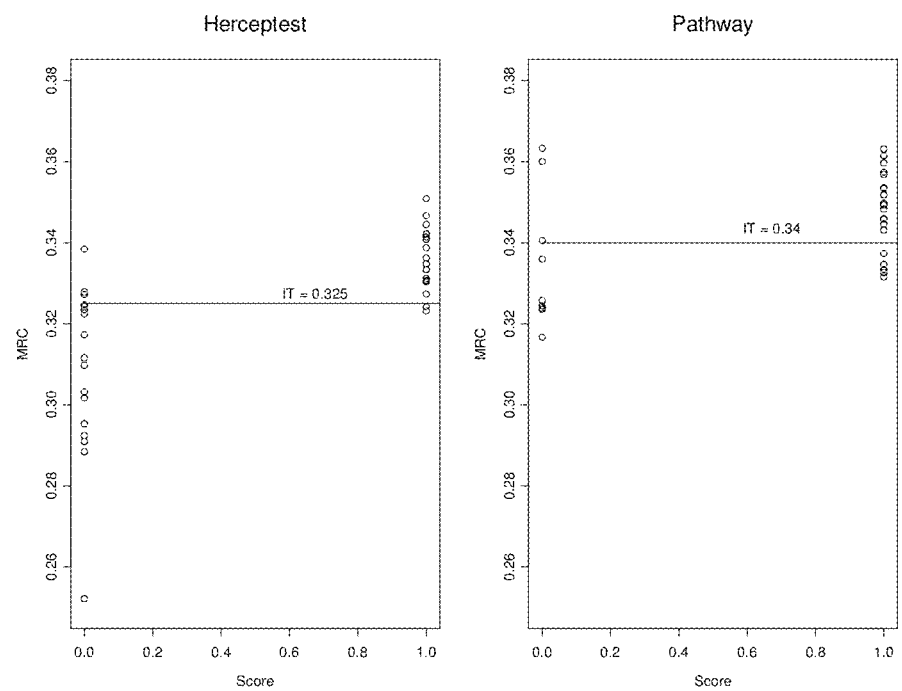

FIGS. 20c and 20d shows two separate cases: POSITIVE (+2, +3) or NEGATIVE (0, +1) which was previously determined by the connectivity index—both for Herceptest and Pathway.

FIG. 20c shows the POSITIVE cases. For Pathway the separation is very significant, based on the intensity feature (MRC). This is not the case for Herceptest, where the distinction becomes more "blurry". Again, this may be due to the fact that "irrelevant" objects are included in the analysis, which may ultimately be dealt with in a number of different ways.

Threshold for Herceptest and Pathway for POSITIVE cases, respectively:
HERCEPTEST
+2 if MRC ≤0.365
+3 otherwise.
PATHWAY
+2 if MRC ≤0.4
+3 otherwise.

FIG. 20d shows the NEGATIVE cases. The distinction between 0 and +1 is somewhat blurry for both Herceptest and Pathway, although the difference in mean is significant. Again, this may be due to the fact that "irrelevant" objects are included in the analysis, which may ultimately be dealt with in a number of different ways.

Threshold for Herceptest and Pathway for NEGATIVE cases, respectively:
HERCEPTEST
0 if MRC ≤0.325
+1 otherwise.
PATHWAY
0 if MRC ≤0.34
+1 otherwise.

Example 11

Diagnosing Breast Cancer Using Normalized Brown.

On the samples as used in Example 9, the Median Normalized Brown (MBrown) is plotted for the Herceptest and the Pathway data. This measure appears to be more robust than Average Normalized Brown (ABrown).

FIGS. 21a and 21b shows MBrown plotted versus (manual) clinical score for each threshold level (T=1, 2, 3, and 4) for both Herceptest and Pathway. It is clear that the MBrown feature is a better discriminator for diagnostic categories for the Herceptest than it is for the Pathway—i.e. the exact opposite situation as is seen for the MRC in Example 10.

Again, this feature appears to work uniformly best for the Membrane identification threshold corresponding to T=2.

The invention claimed is:
1. A method for assessing at least two adjacent sections A and B of a specimen, said method comprising the steps of:
   a) staining section A for one marker specific for one object type in the specimen, and staining section B for another marker specific for another object type in the specimen,
   b) obtaining an image of at least part of section A and an image of at least part of section B,
   c) carrying out an image registration process on the two images by establishing correspondence between features of the two related images obtaining a representation of a corresponding image pair,
   d) assessing marker events for at least two object types on said representation, and
   e) assessing the at least two adjacent sections A and B with respect to the two object types.

2. The method according to claim 1, further comprising the steps of:
   a) obtaining a superimage of at least part of section A and a superimage of at least part of section B,
   b) carrying out the image registration process on the two superimages by establishing correspondence between features of the two related superimages, in order to obtain a mathematical transformation rule,
   c) identifying an image field within section A,
   d) using said mathematical transformation rule to identify an area within section B, said area comprising an image field within section B corresponding to said image field within section A,
   e) obtaining an image of said image field within section A identified in step c) and obtaining an image of said image field within section B identified in step d) to obtain a corresponding image pair,
   f) optionally repeating steps c)-e) one or more times to obtain one or more different corresponding image pair(s) of one or more different image fields in the two sections A and B.

3. The method according to claim 2, wherein the superimages are obtained using a lower resolution than the resolution used to obtain the images of step e).

4. The method according to claim 2, wherein the super-images are obtained using a magnification of ×2.5, ×5 or ×10.

5. The method according to claim 2, wherein a minimum guard zone is added to each border of said area in step d).

6. The method according to claim 2, comprising the additional step of carrying out a second registration process on the two images obtained in step e) to obtain a registered corresponding image pair.

7. The method according to claim 5, comprising the additional step of carrying out a second registration process on the two corresponding image fields and guard zones obtained in step d) to obtain a registered corresponding image pair.

8. The method according to claim 1, wherein said specimen is a biological specimen.

9. The method according to claim 2, wherein said mathematical transformation rule includes a rotation rule and/or a translation rule and/or a warp rule, which is carried out on at least part of the section.

10. The method according to claim 1, comprising the additional step of automatically determining a conclusion from the results of the method.

11. The method according to claim 1, comprising the additional step of automatically determining a pharmacological conclusion from the results of the method.

12. The method according to claim 1, comprising the additional step of automatically determining a conclusion relating to a proliferative index of a cell sample.

13. The method according to claim 1, comprising the additional step of automatically presenting a report, and optionally one or more digital image(s), on a graphical user interface.

14. The method according to claim 1, wherein the considered image field(s) represent a random sample of the adjacent sections, such as a systemic uniform random sample.

15. The method according to claim 1, wherein said image field is a semi-random sample of the specimen.

16. The method according to claim 1, wherein the first image field is identified at random and the subsequent image fields are identified using a pre-defined function.

17. The method according to claim 1, wherein said image field is selected in the specimen by a human operator.

18. The method according to claim 1, wherein said method is carried out for at least three different object types.

19. The method according to claim 1, wherein said specimen is a tissue sample.

20. The method according to claim 1, wherein the specimen includes a plurality of human cells.

21. The method according to claim 20, wherein the plurality of human cells potentially includes one or more human cancer cells.

22. The method of claim 21, wherein the one or more human cancer cells are breast cancer cells.

23. The method according to claim 1, wherein said two object types are two different receptors.

24. The method according to claim 1, wherein said marker events are cells comprising both object types.

25. The method according to claim 1, wherein assessing in step d) is a step for counting said marker events.

26. The method according to claim 1, wherein assessing in step d) is a step for determining the intensity of said marker events.

27. The method according to claim 1, wherein said feature is an anatomical structure.

28. The method according to claim 27, wherein said anatomical structure is one selected from the group consisting of: the outer shape of the section, vascular structure(s), nerve structure(s), muscle structure(s), cell membrane(s), space(s) in the section, cell(s), an alveolus, particle(s) or a nucleus.

29. The method according to claim 1, comprising the additional step of:
   quantifying the amount or number of said counting events on the images of said image field(s) within section A and said image field(s) within section B.

30. A computer readable medium comprising instructions for carrying out the method according to claim 1.

31. An automated system suitable for carrying out the method according to claim 1, comprising, in combination:
   a database capable of including a plurality of digital images of a plurality of biological specimens;
   a software module for analyzing a plurality of pixels from a digital image of a biological specimen;
   a control module comprising instructions for carrying out the method of claim 1.

32. The automated system according to claim 31, wherein said system comprises a slide loader, a barcode reader, a microscope and a stage.

33. A software program comprising instructions for carrying out the method according to claim 1.

* * * * *